(12) United States Patent
George

(10) Patent No.: US 8,600,683 B2
(45) Date of Patent: Dec. 3, 2013

(54) SYSTEMS AND METHODS FOR OBTAINING AND MANAGING SEQUENCING DATA

(75) Inventor: Sean E. George, San Francisco, CA (US)

(73) Assignee: Invitae Corporation, San Francisco, CA (US)

( * ) Notice: Subject to any disclaimer, the term of this patent is extended or adjusted under 35 U.S.C. 154(b) by 0 days.

(21) Appl. No.: 13/348,626

(22) Filed: Jan. 11, 2012

(65) Prior Publication Data

US 2012/0214159 A1    Aug. 23, 2012

Related U.S. Application Data

(60) Provisional application No. 61/431,668, filed on Jan. 11, 2011, provisional application No. 61/546,820, filed on Oct. 13, 2011.

(51) Int. Cl.
*G01N 33/48* (2006.01)
*G06G 7/58* (2006.01)

(52) U.S. Cl.
USPC ............................................. 702/19; 703/11

(58) Field of Classification Search
None
See application file for complete search history.

(56) References Cited

U.S. PATENT DOCUMENTS

| | | |
|---|---|---|
| 6,807,490 B1 | 10/2004 | Perlin |
| 2004/0126767 A1 | 7/2004 | Anderberg |
| 2005/0009078 A1 | 1/2005 | Craford et al. |
| 2007/0269804 A1 | 11/2007 | Liew et al. |
| 2008/0131887 A1 | 6/2008 | Stephan et al. |
| 2008/0195326 A1 | 8/2008 | Munzer et al. |

OTHER PUBLICATIONS

Patent Cooperation Treaty, International Search Report for PCT/US2012/020998, Jul. 27, 2012, pp. 1-4.

*Primary Examiner* — Eric S DeJong
(74) *Attorney, Agent, or Firm* — Pillsbury Winthrop Shaw Pittman LLP

(57) ABSTRACT

Systems and methods for biological sample processing are described. A production line extracts genomic DNA from a biological sample, amplifies target components of the sample and produces sequence data for markers from the amplified components. The markers are associated with tests identified in a requisition received with the sample and some markers may be associated with unrequisitioned tests. A sample information management system (SIMS) controls and monitors the production line and subsequent analysis of the results using information in a quality control (QC) database to validate the results. A repository comprising the QC database and a research database receives and aggregates the results without identifying the source of the sample. A portal may be provided to provide access to the research database to a plurality of external contributors. Contributors can selectively provide additional research data and data can be processed using data mining and curation tools.

5 Claims, 12 Drawing Sheets

Figure 6

SYSTEMS AND METHODS FOR OBTAINING AND MANAGING SEQUENCING DATA

RELATED APPLICATION

The present application claims priority from U.S. Provisional Patent Application No. 61/431,668, filed Jan. 11, 2011, and from U.S. Provisional Patent Application No. 61/546,820 filed Oct. 13, 2011, and both of these applications are expressly incorporated by reference herein for all purposes.

BACKGROUND OF THE INVENTION

1. Field of the Invention

The present invention relates generally to processes for analyzing DNA sequence data.

2. Description of Related Art

Conventional systems for processing samples generally perform tests described or requested in a requisition. Additional testing on the sample requires that a portion of the sample be stored and processed if a subsequent request for additional tests is received.

BRIEF SUMMARY OF THE INVENTION

Certain embodiments of the invention comprise a sample processing production line that may include a genomic DNA extractor configured to extract DNA from a biological sample. The production line typically includes a target amplifier configured to amplify components of the extracted DNA and a sequencer that produces sequence data for a plurality of markers from the amplified components. The plurality of markers may include markers associated with one or more tests identified in a requisition received with the sample. The plurality of markers may also include markers that are not associated with the one or more tests that were requisitioned, but may instead be associated with other tests which were not requisitioned or no test at all.

Certain of these embodiments comprise a sample information management system (SIMS) that controls processing of the sample by the processing production line and analysis of the results of the processing of the sample and a quality control (QC) database that provides the SIMS with QC information. The SIMS may use the QC information to validate processing of samples and analysis of the results. A repository comprising one or more databases receives and aggregates the results generated by processing a plurality of samples. The repository may include the quality control database and a research database. An analyzer may be used to generate test results using information in the repository as well as information obtained from sequencing and analysis of sequencing.

Typically, information identifying the source (patient, test subject and/or healthcare provider) of the sample is removed from the sample, the requisition and the results. The SIMS monitors and controls the processing and analysis of the system using a unique identifier assigned to the sample, the requisition and the results. A subset of the results corresponding to requisitioned tests is generated for delivery to the requisitioner. The subset of results corresponds to a set of tests identified in the requisition and the subset of the results, together with any unrequisitioned results, may be maintained in the repository and may be aggregated in the research database.

Certain embodiments comprise a portal that selectively provides access to data in the research database to a plurality of contributors. The portal communicates with the plurality of contributors via a private and/or public network, such as the Internet, a cellular telephone network, a satellite communications network, an ad hoc network, a WiFi network, a WiMax network or other network. Contributors can selectively provide additional research data to the research database and may use external data mining and curation tools and/or data curation and/or mining tools provided in certain embodiments of the invention to process information provided to the research database.

BRIEF DESCRIPTION OF THE DRAWINGS

FIG. 6 depicts an example in which a client or customer can assign genetic status and condition and/or disease information for individuals in the family history.

DETAILED DESCRIPTION OF THE INVENTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration.

Certain embodiments of the invention provide systems and methods that may be used to perform requisitioned tests and analyses of genetic information in a biological sample and that can perform other tests and analyses on the sample in order to collect additional information. Moreover, certain aspects of the invention enable rapid response to supplemental requisitions and for research purposes. Samples are typically received with a requisition from a client, who is typically a health care provider.

In certain embodiments of the invention, the genetic material to be analyzed is genomic DNA, however, persons of skill in the art will recognize that the invention can be practiced with respect to the sequencing and analysis of other forms of genetic material including mitochondrial DNA, cancer cell DNA such as may be extracted from biopsied materials, germ-line DNA, cDNA, mRNA, and cell-free DNA fragments. Certain embodiments of the invention, references herein to DNA should be understood to embrace various forms of genetic material amenable to sequencing including somatic cell DNA, genomic DNA, germ line DNA, mitochondrial DNA, cancer cell DNA, cDNA, mRNA.

Figure 1:
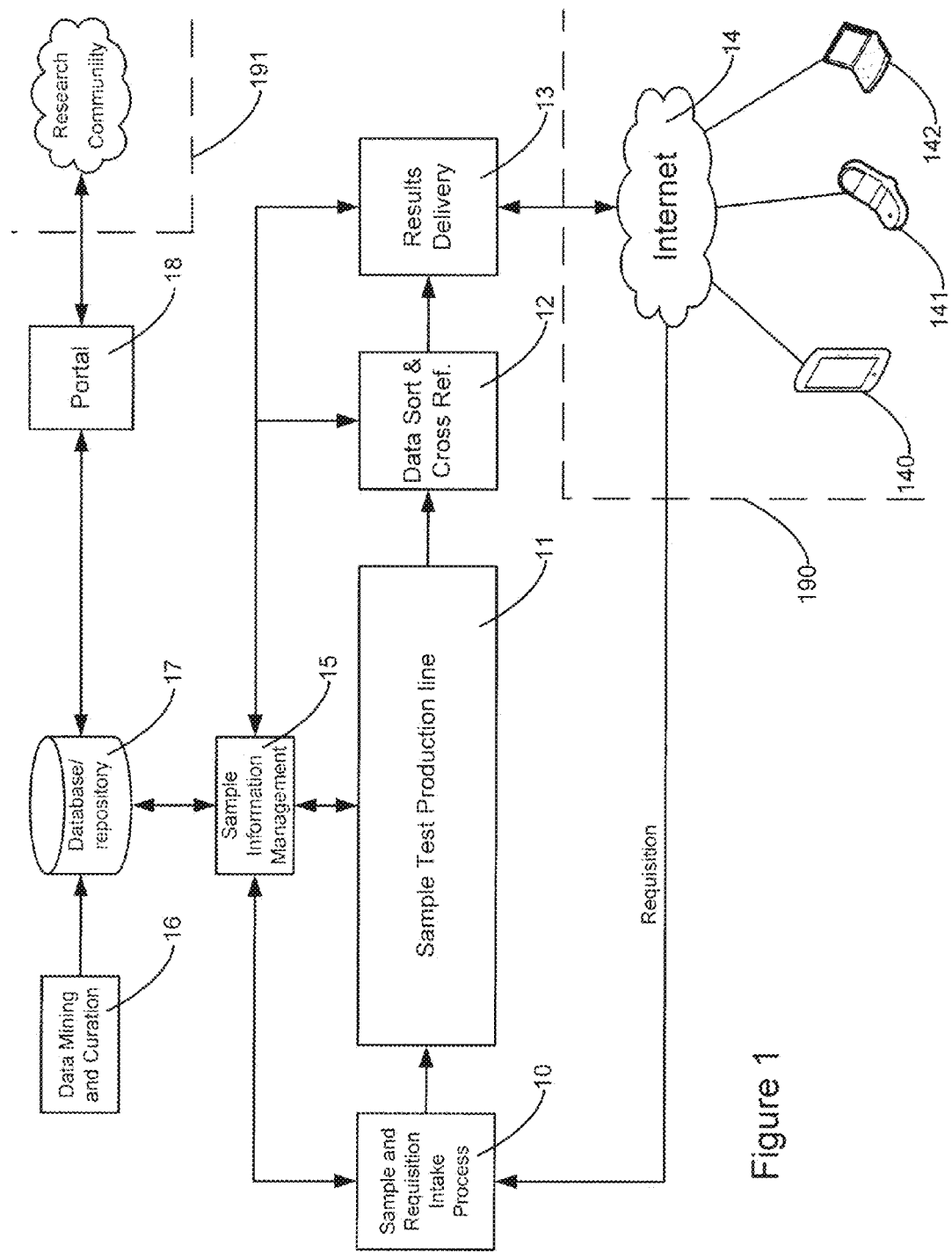
FIG. 1 is a block schematic illustrating an example of a system according to certain aspects of the invention.

With reference to the block schematic drawing of FIG. 1, a sample analysis production line 11 receives samples, amplifies and purifies DNA extracted from the samples and analyzes the purified DNA according to certain predefined protocols. Sample and requisition intake subsystem 10 processes requisitions provided with samples, which are typically submitted by a clinician or other healthcare provider. Requisitions may explicitly identify a set of tests to be performed on the sample, although, in some embodiments, the healthcare provider may establish, in advance, a catalogue of "standard" tests to be performed on samples provided by that provider. In certain embodiments, the submitter of the requisition may request tests associated with one or more medical conditions or diseases and such requested tests may be categorical, e.g., tests related to cancer risk, or specific, e.g., tests related to a single specific disease. In certain embodiments, an interactive intake subsystem 10 can maintain an analysis of prior submissions by the healthcare provider and may select a set of tests based on predefined preferences of the healthcare provider, frequency of occurrence of prior requested tests, identification of a subject from which the sample was obtained, time of year, and/or high volumes of recent test requests driven, for example, by an epidemic.

In certain embodiments, intake subsystem 10 prepares a workflow for each sample, the workflow identifying the requisitioned test sets. Intake subsystem 10 may validate the requisition requirements and may submit identifying, biographic and other information in the requisition for further processing. The workflow specifies one or more tests to be performed on materials included in the sample and the analyses of the test results to be provided in a report to the requestor. The requisitioned tests typically comprise a subset of the available tests that can be performed on materials extracted from the sample. According to certain aspects of the invention, the full set of available tests is performed on the sample, yielding a number of results related to markers, sequence data and tests in excess of those necessary for the tests which were requisitioned. For a variety of reasons, including government regulation, potential liability issues and commercial reasons, it can be desirable to limit the analysis of the assay results to those tests determined to be relevant to the requisition and/or to limit the analyzed results which are provided to the client to those responsive to the requisition. In certain embodiments, such other assay results data will be retained and available for analysis in connection with subsequent requisitions for additional tests without requiring further or additional processing of the original sample or a new sample from the subject.

Certain embodiments of the invention comprise a repository 17, which typically comprises a database, and which receives and maintains information associated with each sample and requisition. The repository 17 maintains test results and associates the test results with an original requisition and sample. Information that can identify a patient who is the source of the sample is typically removed from the sample and from the stored copies of the requisition. Each sample can be assigned a unique identifier that is also associated with the corresponding requisition. Identifying information that directly identifies a patient, client and/or source of the sample is removed from information to be stored in the repository 17 and can be stored in a separate database that can indexed using the unique identifier. In one embodiment, the identifying information may be encrypted using the unique identifier to generate an encryption key and the encrypted identifying information may be maintained in the repository 17 together with the information related to the sample and tests. In some embodiments, a key management system can be used to store and retrieve keys to enable samples and results to be accessed in order to satisfy supplemental requisitions and for other purposes. The results of the full set of tests, analysis of each test can also be indexed using the unique identifier.

In certain embodiments, the sample is entered into the production line 11. Production line 11 performs a sequence of processing steps on the sample. An accessioning step is performed whereby the sample can be registered and identified using a barcode, electronic tag such as an RFID, etc. The accessioning step may use the unique identifier discussed above as a means of tagging and identifying the sample and its components as they progress through the production line 11. Separation of the accessioning process from the intake subsystem allows use of other, third party production line elements without compromising anonymity of the presently described processes. In certain embodiments, the invention provides for receipt of sequence information from a third party source as opposed to the performance of the sequencing activities. Such third party sources of sequence information could provide some or all of the sequence information used in the analysis of results in response to a requisition. Additionally, such third party sequence data could be independently generated or generated in response to directions to perform certain tests based upon the requisition.

Additional processes performed in the production line 5 include a sample preparation step. DNA may then be extracted and purified and provided on an assay plate used for amplification and sequencing.

In certain embodiments, certain production line operations are monitored and controlled by a sample information management system (herein referred to as "SIMS") 15. SIMS 11 typically comprises one or more processors configured to communicate with instrumentation, database management systems ("DBMS") and may be configured to control processing of the sample through the production line 11. Portions of SIMS 11 may be embodied in a controller or instrument of the production line. SIMS 11 operates to control flow of information from intake through publication of results. SIMS 11

In certain embodiments, a repository 17 receives and maintains information associated with each received sample and requisition. In certain embodiments, the repository may additionally comprise information from other sources. Repository 17 typically comprises a database and repository 17 can be used as a source of research data and for quality control purposes. For example, results of tests that have a propensity to fail or to produce inaccurate results may be analyzed using identifiers and quality metrics. Identifiers and quality metrics may be derived from a spectrum of different test results for a population of samples and/or from research based on aggregated results. Quality metrics are typically employed by SIMS 15 to enable monitoring and tracking of results during processing of a sample. In one example, a result of a first test falling outside a predetermined range of acceptable results may be indicative of failure of a second test, the failure of which is otherwise difficult to detect.

Data in repository 17 may be directly accessed for research purposes. However, certain research activities may require aggregation and/or redacting of data in repository 17. In one example, research data may be accessed through a portal system 18 which operates as an intermediate between third party researchers and the repository 17. Portal may execute queries against the repository 17, extracting identifying information before making the results available to a third party or public research entity. Portal 18 may permit a third party researcher to identify data in the repository 17 that fits demographic and biographic profiles. Portal 18 can determine such relationships using the unique identifiers assigned during sample intake. In one example, repository 17 can be queried by a third party for test results obtained from samples contributed by persons matching a certain demographic profile. The portal 18 may process the query, for example, by locating unique identifiers associated with demographic records matching the demographic profile. The located identifiers may then be used to identify complete test results for a study population of subjects matching the demographic profile and relevant portions of the results for each identifier can be returned to the researcher.

In certain embodiments, portal 18 may receive research data from third party researchers for inclusion in the repository 17. Accordingly, repository 17 may include baseline, diagnostic, statistical and other information used to process test results and for quality control purposes. Repository 17 may comprise a plurality of databases and a DBMS that executes queries and performs searching and mapping functions. In certain embodiments, one or more databases of repository 17 can be populated and maintained using data mining and curation tool 16. External and internal databases may be mined using tool 16 and tool 16 may automate various curation functions on the repository 17, including collection, organization and validation functions.

Figure 2:
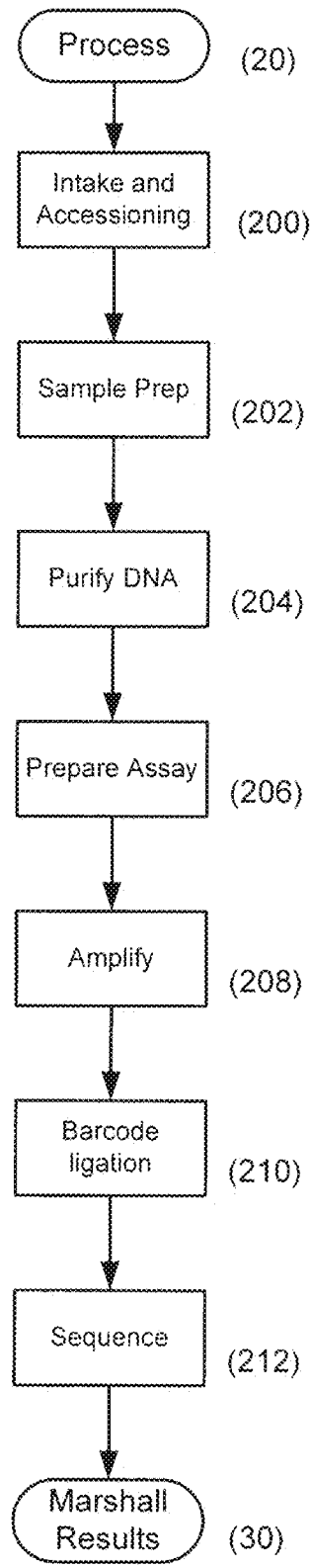
FIG. 2 is a flowchart that illustrates a process flow according to certain aspects of the invention.

FIG. 2 is a flow chart that describes a process flow employed in the example shown in FIG. 1. At step 200, a user provides a sample with a requisition. Information in the requisition is analyzed and validated. The requisition defines one or more tests to be performed on the sample and provides identifying information related to the user and a subject who is the source of the sample. The user may have defined a standard or minimum set of tests to be performed on the sample. In certain embodiments, the intake system may be configured to recognize codes corresponding to a plurality of standard test sets associated with a user or available globally. A requisition may include a combination of individual tests and/or test sets. Having validated the requisition, the sample is typically provided with a unique system identifier, which can be used to track the sample testing process and to disassociate the sample and requisition from information that identifies the subject. Such disassociation enables data extracted from tests performed on the sample to be used for a wide variety of research activities while maintaining an indirect link to biographic, demographic, medical history and other personal information.

At step 202, the sample is prepared for testing and the sample may be divided into portions. One or more portion may be retained for retest and/or further testing. In certain embodiments of the invention, an identical, complete set of tests is performed on all samples and preparation and testing for all samples is consequently identical. At step 204, DNA is extracted from the sample and purified. Assays are prepared at step 206 and an amplification step 208 is performed. Ligation step 210 and sequencing step 212 produce raw data for analysis and reporting using a process 30 described with respect to FIG. 3.

According to certain aspects of the invention, portions of the sample are processed to generate sequence data for all markers then available for analysis or more markers than are directly associated with the requisitioned test, which is then selectively analyzed and interpreted according to requirements set out in the requisition. Reported results are typically limited to the results of tests requested in the requisition. Additional results may be delivered in response to a second requisition provided by the user, where the second requisition directly references the first requisition. Genetic condition/marker information may be delivered to the ordering clinician in a variety of ways. In some embodiments, markers are simultaneously sequenced for many conditions, often measurable by the hundreds or thousands (100s or 1,000s), regardless of the tests requisitioned by the clinician. Sequences generated are targeted from the whole genome, thereby requiring a fairly arduous curation, informatics and assay development process. The analyzed sequence is determined by the clinician requisition, supported by a requisition engine that keeps track of clients and the markers ordered for each client. In accordance with the current regulatory environment, and to limit creation of liability issues for clinicians, only the requisitioned markers will be analyzed for genetic information. The remaining markers can be stored as raw data, and may be disassociated with identifying information (made anonymous), aggregated and stored for research and development and other purposes and/or as data for internal use and for use with collaborators.

A re-requisition process may be implemented that allows the delivery of the entirety of the data or a portion of data other than the requisitioned test data to the client. This re-requisition process may be provided through the requisition engine, by which further data on a specific condition or data from other conditions can be automatically requested and the data integrated into the client solution automatically.

In certain embodiments, the invention provides a method for analyzing diagnostic information, comprising: (i) extracting genomic DNA from a sample; (ii) obtaining sequence data for a plurality of markers, the plurality of markers including a first set of markers which are associated with one or more tests identified in a first requisition corresponding to the sample and a second set of markers which are not associated with the one or more tests identified in the requisition; (iii) generating a response to the requisition, the response being based upon an analysis of sequence data corresponding to the first set of markers and the one or more tests with the generation of the response excluding analysis of the second set of markers with respect to tests other than the one or more tests; (iv) assigning an identifier to the sequence data, the identifier identifying the sample, the requisition and information related to the analysis; (v) storing the sequence data in a repository of data, the repository providing data for analysis; and (vi) reporting additional results of an analysis of the sequence data associated with one or markers of the second set of markers in response to a second requisition, the second requisition identifying a test different from the one or more tests.

In certain such embodiments, the invention provides the step of assigning an identifier which includes rendering the source of the sample and the requisition anonymous. In certain embodiments, the second requisition includes the identifier. In certain embodiments, the information related to the analysis identifies the date of the analysis. In certain embodiments, the step of generating a response to the requisition includes performing quality control on the results of an analysis of the sequence data. In certain embodiments, the step of performing quality control includes performing a comparison using quality information derived from the repository. In certain embodiments, the step of performing quality control includes updating the quality information using the results of the analysis of the sequence data. In certain embodiments, the repository is accessible to contributors through a portal. In certain embodiments, the invention provides the additional step of updating the repository based on contributions made by the contributors. In certain embodiments, the second requisition is made after receiving the results of the first requisition. In certain embodiments, the test identified in the second requisition is not available for identification at the time the first requisition was made. In certain embodiments, the second requisition is made at the time of the first requisition and comprises a request for additional results associated with one or more tests not then available for requisition with such results to be delivered after the occurrence of the availability for requisition of at least one of such one or more tests which were not available at the time the first requisition was made.

In certain embodiments, the invention provides a method for analyzing diagnostic information, comprising the steps of (i) extracting genomic DNA from a sample; (ii) obtaining sequence data for a plurality of markers, the plurality of markers including a first set of markers which are associated with one or more tests identified in a first requisition corresponding to the sample and a second set of markers which are not associated with the one or more tests identified in the requisition, wherein the first requisition includes a request to receive future notifications of health information associated with the sequence data; (iii) generating a response to the requisition, the response being based upon an analysis of sequence data corresponding to the first set of markers and the one or more tests with the generation of the response excluding analysis of the second set of markers with respect to tests other than the one or more tests; (iv) assigning an identifier to the sequence data, the identifier identifying the sample, the requisition and information related to the analysis; (v) storing the sequence data in a repository of data, the repository providing data for analysis; (vi) after generating the response, generating a notification of health information based upon an analysis of some of the sequence data wherein the health information which is the subject of the notification comprises health information which is different from the health information in the response; (vii) and generating such health information after consent for its generation is received.

In certain such embodiments, the health information which is the subject of the notification concerns a change to a prediction in the response to the first requisition where such change arises due to a change in the content of the repository such as the availability of new computational models, or the new availability of prediction methods for new conditions, change in the clinical interpretation of the original requisitioned conditions, update to the background information of the original requisitioned conditions, or new information about a condition that was not yet available at the time of the requisition. In certain such embodiments, the health information which is the subject of the notification concerns one or more tests which were not available for requisition at the time of the first requisition. In certain such embodiments, the health information which is the subject of the notification is generated with reference to sequence data corresponding to at least one marker of the second set of markers. In certain such embodiments, the consent for generating such health information is provided with the first requisition.

Requisition and Sample

In certain embodiments of the invention, requisitioning users comprise clinicians, healthcare providers and intermediaries such as diagnostic companies, insurance companies, pharmacy benefits managers, or some other healthcare provider. An available test menu may be provided to a user interactively, although users may prepare requisitions independently, using agreed codes to define the tests to be performed. In one example, the system may comprise a database maintaining a menu having 50 or more tests. In another example, the database may maintain a menu comprising substantially all available or practical germline genetic tests. The requisition may be submitted through a client portal, an integrated electronic medical record system ("EMR system"), or in a conventional order form. The requisition may also provide instructions that specify levels of background analysis and threshold notification to be performed for any conditions not specifically requested in the requisition.

The tests and/or analysis to be performed may be defined by the client using criteria to define a marker(s), set of genome coordinates, variant(s), gene(s), condition(s), or group(s) of conditions and the client requisition may be entered manually, electronically, or pulled automatically from an EMR or other means of electronic requisition. In certain embodiments, a client may request a threshold scan, in the background or otherwise and the threshold may be quantitative in nature (e.g., testing whether the threshold is above/below or equal to a population percentile, absolute risk, relative risk, odds-ratio etc) or qualitative (at risk, not at risk, unknown, etc). The client threshold request may be entered manually, electronically, or pulled automatically from an EMR or other means of electronic requisition.

The user may order one or more of the available tests, and may request full analysis. The user may identify an order by which examination of specific markers should be prioritized and which, if any, background analysis or specific genes should be checked responsive to the results of the prioritized tests.

A sample submitted for analysis may comprise blood, saliva, tissue, and the like. The sample is typically associated with an identifier that links the sample with its corresponding requisition. The identifier may comprise a barcode, an RFID, or other optically or electronically detectable identifier. A requisition engine can be used to track the patient/barcode relationship and to ultimately re-associate the barcode with patient results while maintaining anonymity throughout the entire processing of the sample. Information in the requisition, including instructions identifying markers to be tested, follow the sample through the lab workflow and analysis and informs both the SIMS and an Analysis Engine. The sample is accessioned and submitted to the lab workflow. A sample submitted may comprise blood, saliva, tissue, cells, and/or genetic material in the form of genomic DNA, prepared DNA, synthesized DNA, RNA or other genetic material.

Lab Workflow

Referring again to FIG. 1, the production line 11 typically performs a variety of functions under the control of, or according to instructions provided by SIMS 15. In one example, genomic DNA is purified from each sample and regions of interest are amplified with primer sets developed using an assay development component that is informed by the repository 17. The primer sets are typically designed using proprietary enhancements to Primer3. Amplification reactions are performed at a very high multiplex, thousands of amplicons at anywhere from 20-300 per well. The amplified regions of interest for each subject are then 'molecularly barcoded' using a ligation reaction. The resulting product of thousands of amplicons for each patient across all regions of interest is then prepared for sequencing and loaded onto the sequencing platform. Sequence preparation may be customized using a manufacturer protocol. Sequencing is then performed and all samples and work product can be stored for future reference. Storage of samples and work product is typically subject to government regulations, such as the Clinical Laboratory Improvement Amendments promulgated by the U.S. Center for Disease Control and Infection. Throughout the entire process, each sample is tracked by the SIMS. In particular, quality metrics, lab inputs, operator, equipment information and all associated data are stored for immediate analysis and reporting or for future reference.

Analysis

In certain embodiments, raw sequences are first analyzed for general quality control metrics using key data provided by the SIMS and based on information maintained in the repository 17. Quality control metrics may be derived from research, statistical analysis of prior test results, controls and other information. Quality metrics may include expected allele frequencies, sequence comparison to reference genome, genetic fingerprint checks, routine sequencing coverage and quality metrics, and so on. Quality metrics may be reviewed to ensure the quality of the run and to detect trends and issues with the production line 11. Some quality metrics may be specific and unique to the combination of production line 11 and workflow employed. In particular, wild-type signal patterns of each locus based on several hundred individuals can be compared to the signal pattern observed in a requisitioned sample. Statistical modeling may be used to assess the probability of a different genotype at a locus of interest. The statistical model typically allows genotype determination of specific mutation types such as insertions/deletions of varying sizes, single nucleotide changes, trinucleotide repeat changes, and copy number differences. Requisition intake engine 10 can be queried to determine which sequence should be interpreted for each subject sample. Subject sequence can be sorted by "molecular barcode," and can be analyzed by referencing the repository 17 and condition/marker data for each requisitioned test is ported to a data handling component 12. The data handling component may comprise a data menu that maintains condition/risk data available for client integration as well as access to the raw data should a re-requisition come from the requisition intake engine 10. Re-requisitions typically are received in response to a background notification or threshold notification indicating availability or potential availability of significant and/or relevant results of unrequisitioned tests. For each test requisitioned, the sequence can be analyzed to provide the genotype at the relevant loci, haploytype sequence, diplotype sequence, qualitative risk score, and quantitative risk score if appropriate for the requisitioned condition. All of the data, as well as any data coming back from the client or collaborators, is stored in an anonymized fashion in the repository database 17.

In certain embodiments, per base quality metrics may be provided for clinical interpretation. Examples and features of quality metrics include: (1) for clinical interpretation a base or set of bases (defined by the curated variant database) may be required to be equal to or higher than a pre-defined quality threshold; (2) use of a pre-defined quality threshold to predict a particular sensitivity, specificity, false negative rate, false positive, negative predictive value, positive predictive value and accuracy; (3) bases or sets of bases (as defined by the curated variant database) that do not meet a pre-defined quality threshold may be considered no-calls and consequently no clinical interpretation may be provided; and (4) the quality threshold may be platform specific with respect to sequencing technology employed and may be determined, partially or wholly, by coverage, base quality values, or other parameters.

Client Integration

Based on the requisition received with a sample, appropriate data is pushed from data handling component 12 to a delivery subsystem or module 13. Delivery subsystem can comprise any combination of software and hardware necessary to format, prepare and transmit results data to a requisitioning user ("client"). The method and content of data delivery is typically configured by client and based on level of service contracted by the client. Portions of delivery subsystem 13 can be integrated with a client computing system such as an EMR system. For example, an agent can be delivered to the client EMR system that includes computer instructions and data that cause the EMR system to receive and record results and to produce a report of results that can be printed and/or transmitted as an Email, SMS text message or other electronic message. Agent can provide and/or utilize various APIs that either port directly to a client's EMR system, to a client's physician/patient portal, generate a fax/email to be delivered to a client, etc. (the report'). Results delivery system 13 can be adapted and configured to provide background or threshold notification according to client preferences, client requests provided in the requisition and in compliance with applicable regulations. If background or threshold notifications are enabled, the client can be informed of such notices and an automatic 're-requisition' can be generated and, when authorized by the client, can cause delivery of remaining information through the results delivery system 13.

In certain embodiments, the clinical interpretation of test results may be augmented by information or samples provided by the client beyond the submitted proband's sample. Such additional information may include pedigree structure and affection status, symptoms, and results of other diagnostic tests. Moreover, additional samples or sequence results from sources related to the patient or proband (such as parents, siblings, and/or offspring) may be submitted to facilitate clinical interpretation.

In certain embodiments, the invention provides a method for updating and delivering additional or supplemental sample analyses, in which a client indicates on a clinical requisition for the performance of certain tests according to the invention her desire to receive future notifications of health information beyond the initial results related to the requested tests, including but not limited to (i) updates to predictions or assessments relevant to the original requisition based on new computational methods; (ii) results related to a specific or general list of conditions maintained by service provider for which prediction methods are not available at the time of the original requisition but which may subsequently become available. In certain such embodiments patient data is derived from data archived from the processing of a sample in association with the original requisition (such as blood, plasma, stool, or other sample) where such data may be archived by service provider or a third party. In certain of such embodiments, the requisitioning institution or physician is notified of the availability of updated clinical information beyond that reported initially in response to the original requisition. Such notification may include one or more of the following: (i) Patient identifier, (ii) Patient date of birth, (iii) Patient gender, (iv) Original sample type(s) and date(s), (v) Original requisitioned condition(s), (vi) A description of the updated information, (vii) An indication of the relevance of the updated information, including: (x) possible changes in the clinical interpretation of the original requisitioned conditions, (y) update to the background information of the original requisitioned conditions, (z) new information about a condition that was not yet available at the time of the original requisition. In certain embodiments, the delivery of this information to the institution or physician is made upon agreement to receive the updated information, or may be made without such agreement if previously waived.

For example, in certain embodiments, a client can select to either immediately receive clinical results for all conditions where notification thresholds are met, or alternatively can select to receive "push notifications" about conditions where notification thresholds are met following the original report in response to the requisition. Following receipt of such a push notification, the client can chose to re-requisition information on some or all of the conditions identified in the push notification through any of the supported requisitioning means and is then presented with the full clinical report by any of the delivery methods of the invention.

For example, in certain embodiments, a client can select to either immediately receive clinical results for all conditions where notification thresholds are met, or alternatively can select to receive "push notifications" about conditions where notification thresholds are met following the original report in response to the requisition. Following receipt of such a push notification, the client can chose to re-requisition information on some or all of the conditions identified in the push notification through any of the supported requisitioning means and is then presented with the full clinical report by any of the delivery methods of the invention.

Clinical Report Generation. In certain embodiments, a clinical report may be represented as data comprising an internal representation of all clinically relevant information or a rendering of that data in a human or machine readable form. In certain embodiments, the analysis pipeline (pipe) produces a clinical report by applying requisitioned (or selected in view of the requisition) risk models and auxiliary analysis (including, but not limited to variant of unknown significance (VUS) analysis). The internal representation of a clinical report contains all the information needed in order to deliver the clinical report to the client or requisitioning organization by one or more of the delivery means including (1) A human readable document (in a format such as PDF, HTML, etc.) that is delivered to the client physically, electronically over the Internet, or by fax, (2) A human-readable presentation on the client portal, and/or (3) A data integration (over the internet or otherwise) with client computer systems (such as electronic medical records, internal client portals, etc). In certain embodiments, generation of a clinical report may be triggered by many different events, including but not limited to (1) the completion of the analysis pipeline (pipe) that triggers clinical report delivery to client or requisitioning party, (2) the re-requisition of additional information from client or requisitioning party, (3) a request for display on the client portal, in real time or in batch mode, or (4) manually, as needed. Clinical reports can be generated from the underlying report data in multiple forms for a single patient, such as sending a human-readable report in parallel with pushing the report data into a client EMR system.

Requisition Engine

In certain embodiments, a portion of the requisition intake element 10 can be provided as a requisition engine that is portable and can be integrated in a computer system operated independently by a client, particularly where the client is a business entity. The requisition engine can also be provided as a standalone component that may be embodied in a mobile device. The mobile device can include notebook computers, cellular telephones, including smart phones, tablet computers and customized device. Requisition engine may include or be coupled to an imaging device such as a scanner, a barcode reader, a camera or other device capable of capturing images that include coded information associated with a patient, a sample, a location an order form or other tangible component. The requisition engine may include an input device such as a keyboard, touch screen, pen interface, mouse, voice recognition system and other input devices through which a client can create and complete a requisition electronically. The client can operate a requisition engine as an order management tool that interacts with sales and marketing channels to interact with end-users.

In certain embodiments, the client may define in a requisition one or more of a marker(s), set of genome coordinates, variant(s), gene(s), condition(s), and/or group(s) of conditions to determine in part the tests to be run or additionally or alternatively the Requisition Engine software may suggest one or more of a marker(s), set of genome coordinates, variant(s), gene(s), condition(s), and/or group(s) of conditions to be specified in the requisition so as to determine in part the tests to be run based on the input of marker(s), set of genome coordinates, variant(s), gene(s), condition(s), group(s) of conditions, symptoms, phenotypes, family history or other client specific information. Such client specific information may be entered manually, electronically, or pulled automatically from an EMR or other means of electronic requisition The requisition and sample intake 10 receives test requisitions from the client and relays the set of tests ordered by the client to the SIMS and identifying information associated with the inbound sample. Upon completion of the analysis and transmission of the results to the client, the requisition engine may be activated to notify the client of a background or threshold notification where configured by the client. When a background or threshold notification is activated and the client is informed, and automatic or manual "re-requisition" can be created to enable delivery of the remaining information. The requisition engine can also be configured to track patients and version information of the production line 11 or elements of the production line 11 platform used to perform tests on submitted samples. After development of new or updated test procedures and processes, it is often preferable to retest samples to obtain higher quality results and, where a new test is indicated, certain benefits accrue from using a new sample for testing. Consequently, process version information may indicate whether the requisitioning physician should submit a new sample in preference to generating a re-requisition for data that already created during prior tests.

Figure 4:
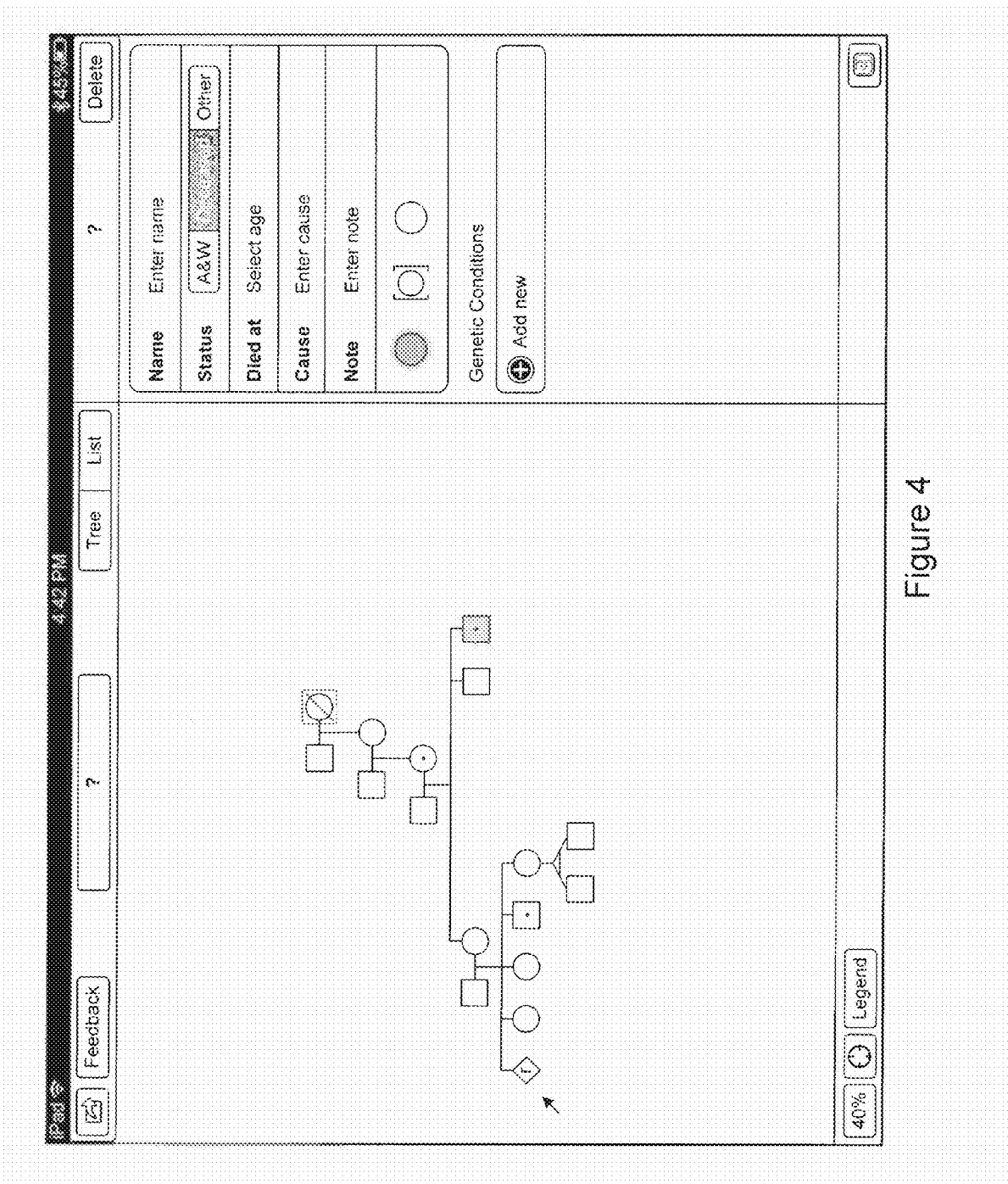
FIG. 4 is received from a touch-enabled family history application that can be executed on a tablet computer or other mobile device.

In certain embodiments, a portion of the requisition intake element 10 can be provided as a requisition engine that is portable and can be integrated in a computer system operated independently by a client. The client can be an individual, a group of individuals and/or a business entity. The requisition engine can be provided as a stand-alone component that may be embodied in a mobile device. Suitable mobile devices can include notebook computers, cellular telephones, including smart phones, tablet computers and customized device. In one example, input to the requisition engine depicted in FIG. 4 is received from a touch-enabled family history application that can be executed on a tablet computer or other mobile device.

Figure 5:
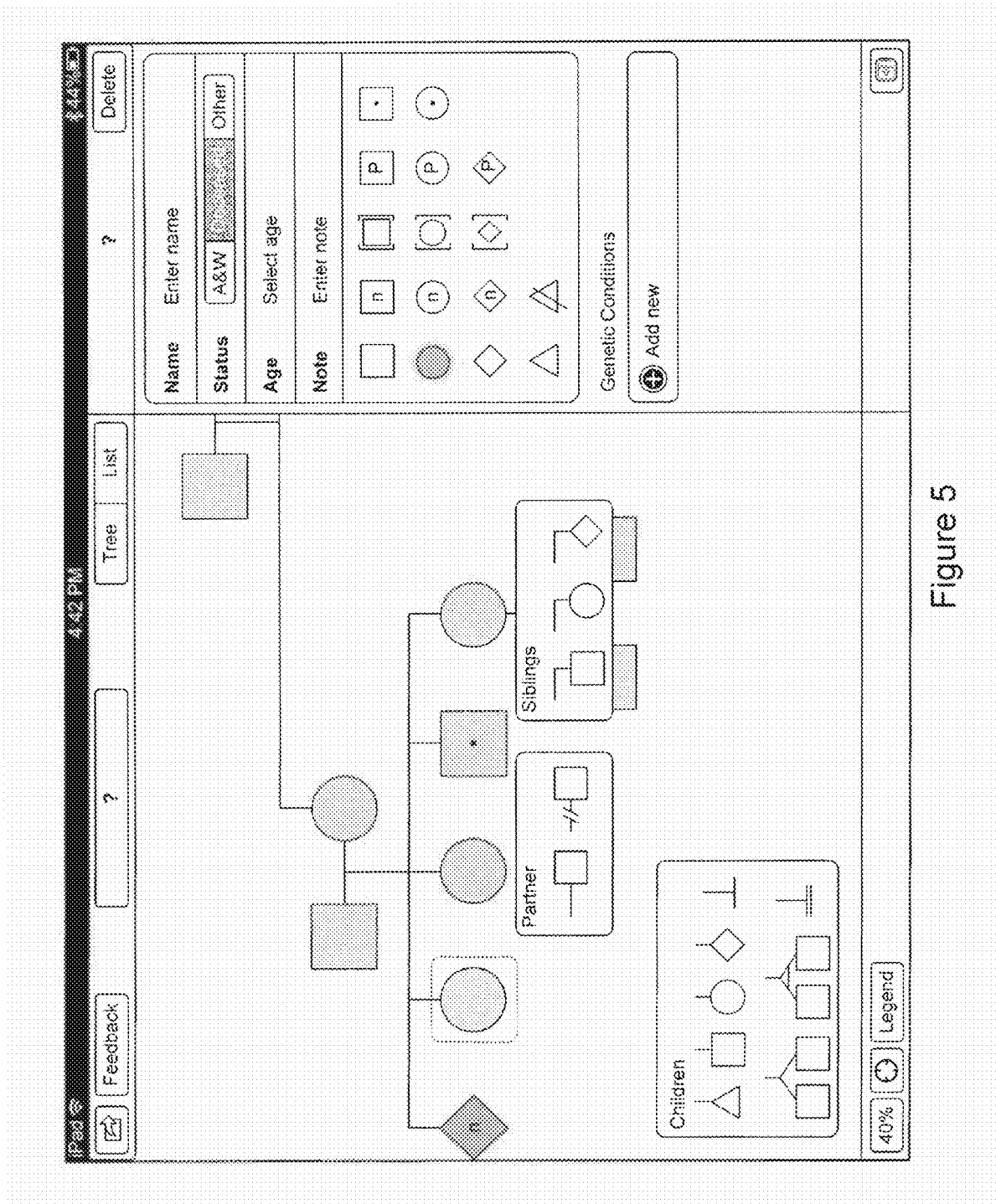
FIG. 5 depicts an example in which a client or customer uses a requisition engine to record family health history for an individual by drawing on the application with a finger or stylus, and/or by using icons provided by a client application on the touch-screen enabled device.
Figure 6:
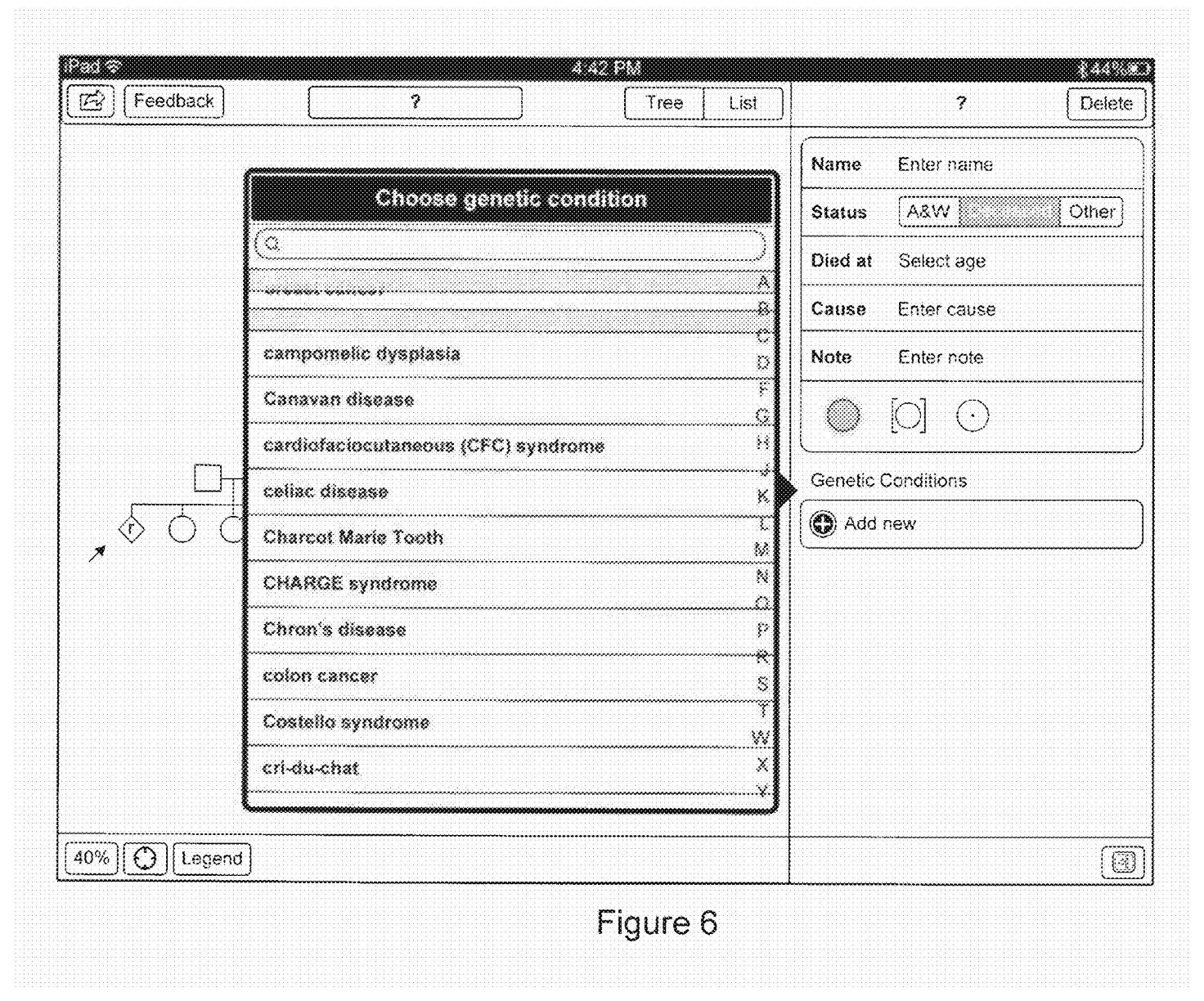
Figure 7:
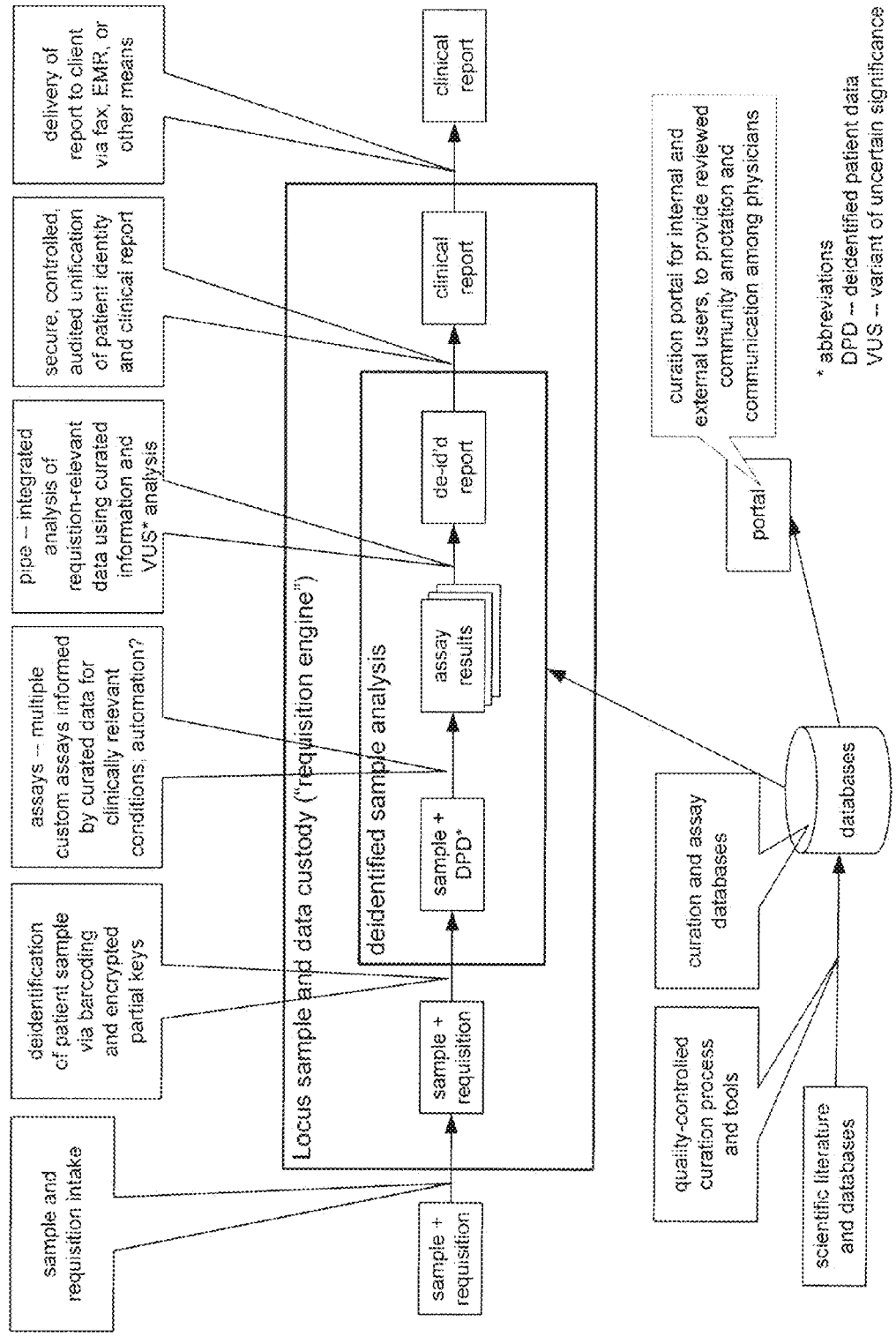
FIG. 7 is a block schematic illustrating an example of a system according to certain aspects of the invention.

FIG. 5 depicts an example in which a client or customer uses a requisition engine to record family health history for an individual by drawing on the application with a finger or stylus, and/or by using icons provided by a client application on the touch-screen enabled device. FIG. 6 depicts an example in which a client or customer can assign genetic status and condition and/or disease information for individuals in the family history. The genetic and disease/condition information collected by a requisition engine according to certain aspects of the invention can be associated with the patient and either directly submitted as a part of the requisition. The information can also be routed to the client's EMR and be included with the requisition generated from the EMR. The information can be printed out and attached to paper/fax requisitions, as desired.

In practical use, the family history tool can be used to port disease data for all members of the family and can be directly transmitted to the patients' EMR or PHR. Probabilities for carrier status, likelihood of the disease state, and mode of inheritance can be calculated real time as the clinician is entering the information. Genetic test data can also be ported back to the family history tool, further enabling the direct calculation of risk to an individual represented in the tool. As well as the calculation for inheritance of complex and/or multigenic traits. Sets of information, including those described herein, can also flow through to the EMR/PHR of other persons in the family history, i.e. other members of the family's medical records can be updated with information collected in other family members' medical history intake. The family history tool can inform the clinician on the full list of diseases and/or genes that can be ordered and can automatically include that information in a requisition generated from within the tool. The family history tool can also combine other data available to the clinician such as weight, cholesterol levels, blood chemistry, biomarkers, environmental factors, etc. to further refine disease risk estimates in the tool for specific diseases (i.e. the Gail model for breast cancer, or other factors for Warfarin dosing).

Figure 8:
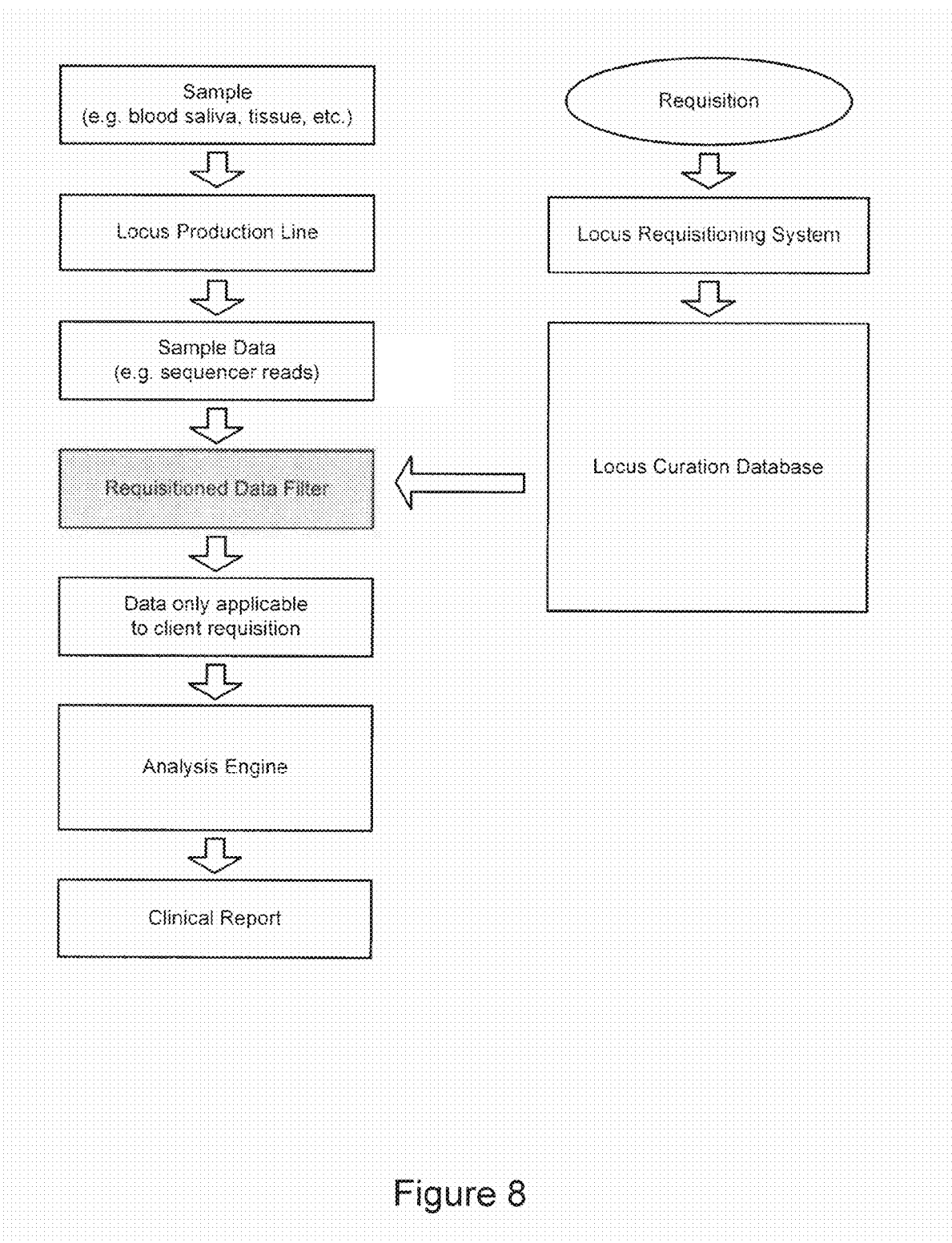
FIG. 8 is a flowchart that illustrates a process flow according to certain aspects of the invention as they relate to filtering of sample data based upon the specific requests made in the requisition in order to limit the analysis of the sample data to those markers applicable to the client requisition.

In certain embodiments, the invention provides software and/or processes to limit analysis to variants, genes, markers and/or conditions that have been requisitioned by the client or are determined to be applicable to the requisition. In certain of such embodiments the determination of the applicable variants, genes, markers and/or conditions to be analyzed may be accomplished by requisitioning and analysis software which works together with the curation database to filter the data generated with respect to the sample and limit the analysis to those aspects of patient data (e.g., genetic sequence) which are relevant to the requisition as illustrated in one example in the flow-chart of FIG. 8. Data that is generated from a patient sample may include data which does not apply to the particular requisition. This un-requisitioned data can be filtered out upstream of the risk engine which performs the analysis of the data and remains un-analyzed as can be attributed to a patient.

Curation

The repository 17 and its constituent databases can be populated using data that is obtained from external sources. Certain information used to populate the repository 17 may be found in one of thousands of publicly available databases, test registries, private databases, academic journals, and so on. Accordingly, certain embodiments comprise various curation tools that manage intake and maintenance of such information and which can automate curation and annotation of information. The process is typically supervised and reviewed by geneticists and epidemiologists. The curation tools may include database scraping tools, natural language processing tools, automated literature search tools, file maintenance tools, activity loggers, group editing tools, etc.

The process of curating clinical variants, their associated markers, and their relevance to various conditions and risk factors may, in certain embodiments, entail one or more of the following steps, which may be performed in any order suitable to the process: (a) determining relevant genes for a condition using a variety of sources, (b) determining relevant papers in the scientific literature, (c) reading the papers to assess outcome relevance, (d) mapping published variants to genome coordinates, (e) determining if variant is pathogenic or questionable significance, (f) collecting all information needed to assess significance of a variant, (g) determining risk model of condition, (h) documenting and communication of primary curation, (i) quality check of primary curation, (j) condition loading. These steps may be performed in different orders from the above. The development of a curation database comprising a collection of pathogenic variants may be initiated and or augmented by exploring conditions, genes, chromosome regions, or symptoms and their associations with certain markers.

In certain embodiments, the invention provides for a method of performing the curation process with respect to a sample where such method incorporates one or more of the following steps: (a) collecting all relevant pathogenic alleles in all relevant genes which will be tested and analyzed such that they are determined before the sample is tested, (b) determining the risk model for such novel pathogenic alleles in all relevant genes before the applicable samples are tested, (c) determining the standards for such novel pathogenic alleles in all relevant genes before the applicable samples are tested, and (d) determining the haplotypes for such pathogenic alleles in all relevant genes is determined before samples are tested. The order of steps (a)-(d) may be varied and or certain steps may be conducted concurrently or aspects of such steps may be performed in different orders with respect to different pathogenic alleles. In certain embodiments, criteria which may be used for inclusion or exclusion of information in a curation database may be applied consistent with one or more of the following principals. A pathogenic variant for a condition with a qualitative risk model is an allele that is observed in an affected individual and results in an alteration (deletion, insertion, base change) of a consensus splice acceptor or donor site, alters the initiation codon, introduces a stop codon, results in a frameshift of the protein, results in a missing exon and can be mapped unambiguously to the human genome OR is an allele that is observed in an affected individual and has been demonstrated to have a functional effect in an experimental assay. A questionable variant for a condition with a qualitative risk model is an allele that is observed in an affected individual and results in a missense protein change, silent protein change, an inframe deletion or insertion, removal of a stop codon, promoter change, intronic change outside of the consensus splice sites and can be mapped unambiguously to the human genome and has not been demonstrated to have a functional effect in an experimental assay. A variant can be mapped unambiguously to the human genome when two pieces of independent mapping evidence are available. Two of the following types of evidence are required amino acid change, nucleotide position and change, sequence trace, another identifier (like an rsID or HGVS annotation), alignment or other piece of information. A pathogenic variant for a condition with a quantitative risk model is an allele that has been shown to meet genome-wide statistical significance in one study and has been replicated (at statistical evidence) in another independent study and can be mapped unambiguously to the human genome.

In certain embodiments, the invention provides for a curation database comprising risk models assigned to a marker, variant, location, gene or condition. Features of risk models may include some of the following characteristics. A risk model describes the phenotype produced for a particular genotype at a locus or set of loci. Risk models may be quantitative or qualitative. A condition may have more than one risk model. Risk models may incorporate alleles, genotypes, haplotypes, or diplotypes at one loci or a set of loci in any combination. Qualitative risk models may use non-descript words such as "risk or not at risk" or may be specific to the outcome "at risk for lower lung function". Quantitative risk models may use odds-ratios, hazard-ratios, relative-risks or other quantitative measurements of an analyte.

In certain embodiments the invention provides for various tools to facilitate the curation process including the development of content in the curation database. Such tools which may be used in the process of performing the curation process or aspects thereof include the following tools: (a) a curation tool that allows the user to enter the amino acid change in one letter or three letter code and position and returns the nucleotide position (relative to the coding or RNA sequence) of a GenBank accession number, (b) a curation tool that allows a user to entire the HGVS-formatted position of a NBCI reference sequence with or without the nucleotide changes and returns the genomic coordinates (chromosome and chromosome start and stop positions), (c) a curation tool that allows a user to entire the HGVS-formatted position of a NBCI reference sequence with or without the nucleotide changes and returns the reference allele present in a reference genome, (d) a curation tool that allows a user to visualize different coordinate systems (RNA, DNA, protein) at different zoom levels, (e) a curation tool that allows a user to track relevant publications (identifiers, publication, supplements) by condition, (f) a curation tool that reverse complements nucleotide changes when the user enters the strand information for a gene and the variant alleles, (g) a curation tool that generates database entry forms from curator excel worksheets, (h) a curation tool that checks for consistency between different curated values, (i) a curation tool that predicts functional protein changes from nucleotide changes and an accession number (RNA or DNA), (j) a set of templates for entry into a form, software program, database, or other electronic media (see template examples).

Use of curation tools may be accomplished by any means of accessing the curation database and information that may be entered into the database may be done manually, through curation tools or through portal 18. Such information that may be included in the curation database may include any or all of the following set of values for each variant that may be needed to go from sequence to report such as (a) mutation type, (b) position information (including specification of any or all of (i) chromosome, chromosomal position relative to genome build, (ii) position relative to DNA accession, (iii) position relative to RNA accession), (c) observed alleles, (d) observed haplotypes, (e) haplotype phenotypes, (f) reference source for haplotype phenotypes, (g) variant aliases, (h) condition name, (i) risk model(s) appropriate for condition, (j) clinical subtypes included with condition, (k) relevant gender for condition, (l) epidemiological data which may be relevant for condition (including any or all of the following as applicable: (i) ancestry, (ii) age, (iii) lifetime risk, (iv) prevalence, and/or (v) incidence); (m) for each quantitative allele/genotype/haplotype/diplotype, as applicable, the odds-ratio (or other quantitative metric), relevant ancestry, reference, and or frequency, (n) for each qualitative allele/genotype/haplotype/diplotype, as applicable, the risk allele, the nonrisk allele, the unknown allele, the reduced penetrance allele, the full penetrance allele, and or the mutable allele, (o) the applicable risk model type, i.e. whether it is quantitative, qualitative, or multi-locus quantitative, or multi-locus qualitative.

In certain embodiments, the curation process may include steps of determining condition groups. A condition group is a set of related conditions that should be tested and reported together. For example, a condition group could be the CFTR condition group comprising the following conditions: Cystic fibrosis, Congenital bilateral absence of the vas deferens, Cystic fibrosis (modifier MBL2), Cystic fibrosis (modifier TGFB1), modifier of CFTR related conditions.

In certain embodiments, a collaborator portal 18 can serve up data from external researchers and experts. For example, experts in a specific disease can upload relevant curation data and/or can perform curation using the curation tools available to them through the portal, although it will be appreciated that the experts can use their own tools, which may be configured to automatically deposit relevant information into the repository. Such curation tools can include curation tools as described herein as well other tools suitable for curation processes.

Locus Database

In certain embodiments, repository 17 comprises a database which maintains information that enables assay design for sequencing of loci of interest (the "Locus Database"). The Locus Database may additionally maintain clinical information that can be accessed by an analysis engine used for interpretation of test results. Typically, the Locus Database is continually updated and updates are tracked using version numbers. Each requisitioned sample processed and tracked by the SIMS can be marked or "stamped" with information indicating the version of the Locus Database (and other system components) in use when the test was performed. The Locus Database may inform the SIMS for quality control of sequencing data by checking against reference, allele frequencies, molecular fingerprinting, etc. In addition, the Locus Database can maintain any relevant information for submission to state and federal regulatory authorities in validation packets or other correspondence. The Locus Database can be populated using the curation tools, manual entry and from information entered through portal 18.

The fields for the Locus Database may include any or all of the following set of values for each variant that may be needed to go from sequence to report such as (a) mutation type, (b) position information (including specification of any or all of (i) chromosome, chromosomal position relative to genome build, (ii) position relative to DNA accession, (iii) position relative to RNA accession), (c) observed alleles, (d) observed haplotypes, (e) haplotype phenotypes, (f) reference source for haplotype phenotypes, (g) variant aliases, (h) condition name, (i) risk model(s) appropriate for condition, (j) clinical subtypes included with condition, (k) relevant gender for condition, (l) epidemiological data which may be relevant for condition (including any or all of the following as applicable: (i) ancestry, (ii) age, (iii) lifetime risk, (iv) prevalence, and/or (v) incidence), (m) for each quantitative allele/genotype/haplotype/diplotype, as applicable, the odds-ratio (or other quantitative metric), relevant ancestry, reference, and or frequency, (n) for each qualitative allele/genotype/haplotype/diplotype, as applicable, the risk allele, the nonrisk allele, the unknown allele, the reduced penetrance allele, the full penetrance allele, and or the mutable allele, (o) the applicable risk model type, i.e. whether it is quantitative, qualitative, or multi-locus quantitative, or multi-locus qualitative.

The Locus Database may additionally identify condition groups as sets of related conditions that should be tested and reported together. For example, a condition group could be the CFTR condition group comprising the following conditions: Cystic fibrosis, Congenital bilateral absence of the vas deferens, Cystic fibrosis (modifier MBL2), Cystic fibrosis (modifier TGFB1), modifier of CFTR related conditions.

In certain embodiments, the information may be stored in the database so as to combine odds ratios for certain variants, markers, genes and/or conditions. In certain such embodiments, information in the database related to individualized combined odds ratios may demonstrate some or all of the following features: (a) method of combining published odds ratios for independent variants into one risk score, (b) incorporation of the age of patient (and how the associated risk changes over time), (c) incorporation of ancestry of patient, (d) incorporation measures of uncertainty (confidence intervals), (e) use of logistic regression models, (f) easy extendablity to non-genetic factors, (g) calculation of where an individual stands in relation to a reference population by generating simulation for all possible risk combinations, based on hapmap allele frequencies if available, and if not, based on published frequencies.

The database representation of genomic features permits, in certain embodiments of the invention, the computational manipulation, comparison, and conveyance of instances of variation as a single class of objects rather than as disjoint classes. In the course of abstracting types of biological variation into a single variation type, biological variation types may include, but are not limited to: (a) single nucleotide variants, (b) multi-nucleotide variants, (c) haplotypes, (d) insertions and conversions, (e) deletions and fusions, (f) duplications, (g) copy number variations, (h) inversions, and or (i) translocations. Associated data may be linked to one or more abstract variant types. Such associated data may include, but is not limited to: (i) references, (ii) provenance, (iii) comments, (iv) risk models, (v) phenotypes (i.b.n.l.t), (vi) drug response, and or (vii) morphology.

Assay Development

In certain embodiments, the sequencing step 214 (see FIG. 2) includes a step of amplifying 208 loci of interest upstream of the sequencing platform. The Locus Database may be used to inform the amplification stage of the positional information of each marker and a series of primer sets can be designed using automated tooling. These primer sets can optimize coverage of all regions at highest multiplexy possible. In one example, multiplexy levels can be in the range of between 10-10,000 amplicons per well. Redundant coverage may be designed for any given locus of interest so that natural, and largely unknown, variations in the genome typically will not disrupt the targeted amplification to a degree that sequences are not read for any of the target regions. After targeted amplification, the amplicons for each patient are barcoded with a sequence such as delineated post-sequencing. The barcoded sequence can be used to assign the "sequence species" to each patient by the analysis engine.

In certain embodiments, the invention provides an assays database which is a data repository for managing information regarding molecular assays. Molecular assays are molecular reagents or designs for producing molecular reagents which are designed to assay molecular attributes, such as genetic variation, which are associated with phenotypic state, such as the presence of inherited disease. Examples of molecular assays for genetic variation include oligo pairs for PCR amplification, oligo sequences for hybridization-based DNA capture, and reagents for whole-genome shotgun sequencing. The information which is tracked with molecular assays for genetic variation can include any or all of the following: (a) the identity of any nucleic acid sequences involved in the reagent, (b) the type of reagent (PCR, hybridization capture bait, etc. . . . ), (c) the region of the genome which is assayed by the reagent, (d) the known genomic variants which are assayed by this reagent, (e) the type of variants which are assayable with this reagent, (f) the genetic conditions which are associated with these variants, (g) quality assurance information (e.g., the pass/fail state of the assay for use in a molecular diagnostic process and or metrics regarding the expected quality (coverage, expected sensitivity, specificity) of the assay), (h) information associated with the genomic region which informs the relative success of the assay such as the G+C % content, the presence of low-complexity repeats, and the presence of similar regions in the reference sequence.

Sample Information Management System

After intake and accessioning, a sample and its associated information associated can be tracked through the testing process and until reported to the requisitioning client. The sample information management system or SIMS is informed by the requisition engine 10 regarding identity of the patient and/or client from whom the sample is obtained and the set of requisitioned tests for the sample. The SIMS can perform in-test analysis and quality checks as well as raw sequence quality checks before the data is sent to the Analysis Engine. In addition, the SIMS can perform functions that a conventional laboratory information management system ("LIMS") would typically perform. The SIMS may also maintain operator data and can perform statistical analyses to continually improve the in-process testing and quality control. In certain embodiments, the sample information management system is a software system for the management of the entire sample life-cycle along with associated primary data (e.g., dna sequence reads, instrument data files, lab personnel observations), secondary data (e.g., quality control ("QC") metrics, statistical data, etc.), and process data (e.g., workflow QC, sample quality metrics, automation consistency).

In certain embodiments, the sample information management system has the following primary functions: (a) integration with the upstream requisitioning system to allow for eventual de-anonymization when sample reports are ready to be reported to a client, (b) tracking of all states and events associated with the processing of patient sample(s) as well as providing instructions and protocols to laboratory personnel in a manner compliant with state and federal regulations, including as they relate to normal operations, generation of deviation reports, and related information, (c) controlling the processing work-flow, including QC controls, failure modes, and failure recovery, (d) tracking all data generated during sample processing, including both primary and secondary processing as produced by lab personnel, external sources, lab equipment, and related sources, (e) tracking all reagents used in work-flow, the batches/lots they belong to, the vendors that they were procured from, vendor QC metrics, and related information, (f) tracking all physical machines, personnel, data access, involved in the work-flow, such as QC engineers, lab technicians, genetic sequencers, thermal cyclers, and related equipment, (g) integration with report generation system and Requisition Engine, and/or (h) allowing retrospective QC.

In certain embodiments the SIMS is configurable and can accommodate multiple sample-processing work-flows, sample transformation such as split/pool/merge/transfer aliquots, sample multiplexing, etc., along with all associated data (primary, secondary & process) generated at every step of each work-flow. The SIMS can act as a repository for all generated data, primary, secondary, and process data. This data may be stored directly in the SIMS (database, file system, or any mixture of thereof) or may be stored externally (in databases, file systems, specialized data stores, or any mixture thereof). Data is entered into the SIMS through automatically or manually sending and receiving data to and from individual machines involved in work-flow by multiple means such as over the local computer network, over the Internet, via handheld devices, as well as data entry through the SIMS user interface, with or without assistance from external devices such as bar-code scanners, etc.

In certain embodiments, the SIMS can provide the application of continuous and statistical process monitoring to improve the quality and robustness of molecular genetics testing. Some of the process elements which can be monitored include: (i) switched samples, (ii) sample contamination, (iii) reagent lot quality, and (iv) analytical instrument quality. To detect the presence of switched samples (e.g., mis-identified laboratory samples) one or more of the following method steps may be performed. A gender check process may be performed for a sample by performing molecular assays which assay the presence or absence and copy number of the sex chromosomes (X and Y). The molecular gender (XX, XY, XXY, etc. . . . ) is compared with the reported gender for that sample. If a discordance in gender is detected, such event suggests a possible indicator that the samples were misidentified and optionally the sample is further checked or the analysis is repeated with a fresh sample. A genetic "fingerprint" step can be performed to check for the possibility of a switched sample by (i) reserving a portion of a sample (the reserved sample) for generating a genotypic fingerprint associated with the sample, (ii) running molecular assays for the sample which are designed to detect genomic variants which are present at a high frequency in multiple human sub-populations (in certain embodiments approximately 20 or more such loci are assayed) such collection of results providing a genetic fingerprint for such sample, (iii) verifying the correct labeling of the sample by generating the applicable genetic fingerprint for the reserved sample, preferably using an orthologous method for assaying genotype such as real-time PCR, high-throughput genotyping arrays, or capillary electrophoresis sequencing, and (iv) comparing the genetic fingerprint for the sample and the reserved sample such that a discordance in the two genetic fingerprints suggests the occurrence of a misidentified sample and optionally a fresh sample is obtained to replace or confirm the analysis of the original sample.

In certain embodiments, the invention provides methods for detection of sample contamination (e.g., assay results resulting from non-pure samples), which methods may include one or more of the following approaches. In certain embodiments, a genetic fingerprint as described herein is measured with respect to a certain number of high-frequency variants) can be used to detect cross-sample contamination. For germline DNA testing alleles can be expected to be present in 2:0, 1:1, or 0:2 ratios. The presence of variants at non-standard ratios (esp. low-frequency ratios) can indicate a possibly non-pure sample. In certain embodiments, the invention provides methods of detecting possible sample contamination comprising the steps of generating a genetic fingerprint for a sample, checking for the presence of non-standard allele ratios (i.e. ratios other than approximately 2:0, 1:1, or 0:2) and determining that sample contamination may have occurred if a non-standard ratio is detected.

In certain embodiments, the invention provides for a method of detecting sample contamination comprising the steps of (i) ligating DNA barcodes to both ends of the starting DNA fragments derived from a sample, and (ii) reading the DNA barcodes in the sequencing process, and (iii) checking for incorrect barcodes as an indicator of possible sample misidentification.

In certain embodiments, the invention provides methods for the assessment of total process quality comprising one or more of the following steps. Control samples may be used to test overall process quality. To verify the proper functioning of the reagents, processes, and instruments involved in the diagnostic workflow, periodically assaying control samples from well-characterized molecular sources (for example, a well-characterized molecular source for genomic DNA is DNA from the Coriell cell repository) to verify process consistency and noting possible defects in process quality in the event that an assay of a control source yields a result different from its reference value. Continuous monitoring-process metrics may be tracked, continuously or episodically, and observed to verify operational consistency. Examples of such metrics include the following: (i) the amount of DNA after the fragmentation step, (ii) the distribution of DNA fragment lengths, (iii) the number of aligned sequencing reads per sample, (iv) the average readlength of sequencing reads, (v) average sequencing quality (Phred score, observed error), (vi) the total number of aligned bases, (vii) the number of variants called, and or (viii) the ratio of transversion vs. transition in variants. In certain embodiments, the invention provides the use of one or more of these quality monitoring steps and the comparison of the results of such quality monitoring step(s) with the applicable reference standard or expected range of values for such quality metrics. Observations of quality metrics may be collected, analyzed, presented and or observed using any of (i) tables of the mean, variance, median, mode, or other statistical characterizations vs time so as to show changes in such values over time, (ii) box plots, (iii) control charts, (iv) correlations of variations in metrics with changes in other elements of the process such as changes in reagent lots, instrument maintenance, lab personnel changes, environmental effects, etc.

Analysis Engine

Certain embodiments comprise an Analysis Engine that combines hardware and software components that read and interact with sequence information resulting form sample testing. Analysis Engine can comprise instruments, processors and interfaces. Analysis Engine typically receives raw sequences and sorts and identifies "sequence species" for the patient based on the barcode sequence. Next loci of interest can be queried against a locus database according to instructions provided by requisition engine 10. Clinical results can be processed and ported to the data sort and cross-reference component 12. Data may be transmitted to the repository 17 for storage in one or more databases. The data is typically rendered anonymous prior to transmission to the repository 17. Other clinical/patient information may be transmitted to the repository, as indicated by requisition engine 10 or based on requests from the collaborator portal 18.

In certain embodiments, the Analysis Engine may be used to analyze information so as to combine odds ratios for certain variants, markers, genes and/or conditions. In certain such embodiments, information related to the analysis of individualized combined odds ratios may demonstrate some or all of the following features: (a) method of combining published odds ratios for independent variants into one risk score, (b) incorporation of the age of patient (and how the associated risk changes over time), (c) incorporation of ancestry of patient, (d) incorporation measures of uncertainty (confidence intervals), (e) use of logistic regression models, (f) easy extendablity to non-genetic factors, (g) calculation of where an individual stands in relation to a reference population by generating simulation for all possible risk combinations, based on hapmap allele frequencies if available, and if not, based on published frequencies.

Figure 9:
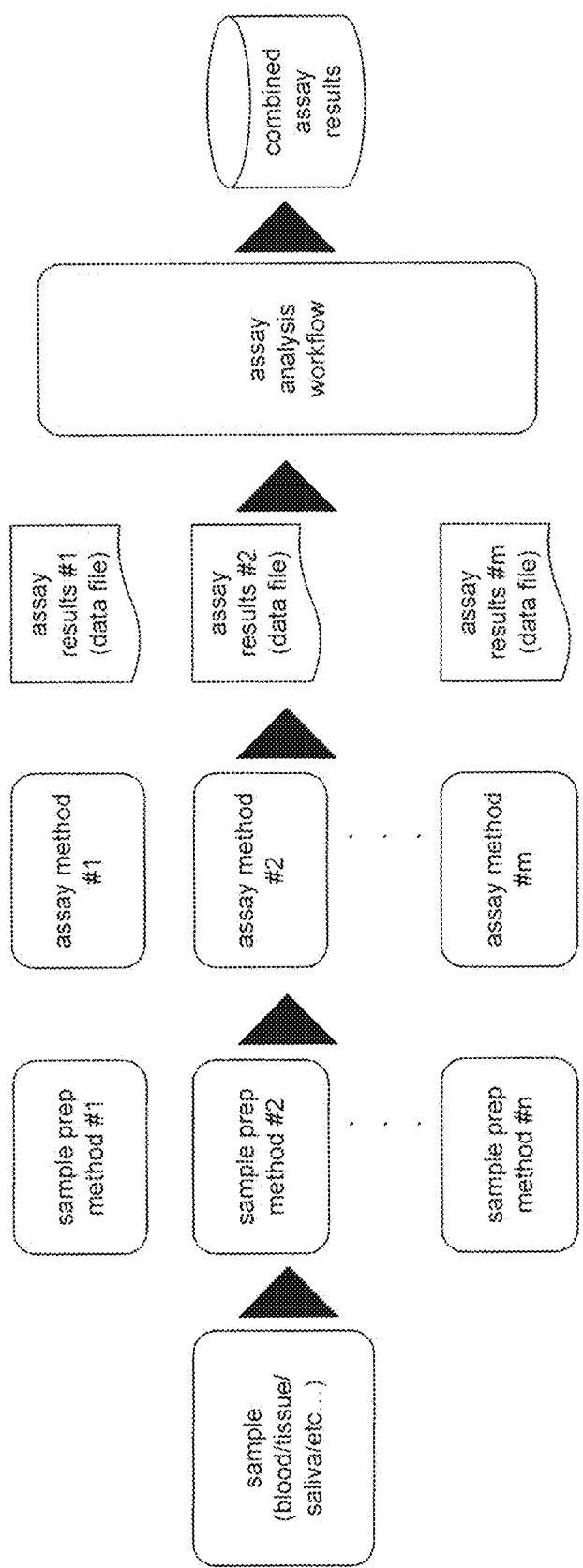
FIG. 9 is a flowchart that illustrates a process flow according to certain aspects of the invention as they relate to the derivation of attributes which are associated with phenotypic state through the combination of data from one or more laboratory workflows.
Figure 10:
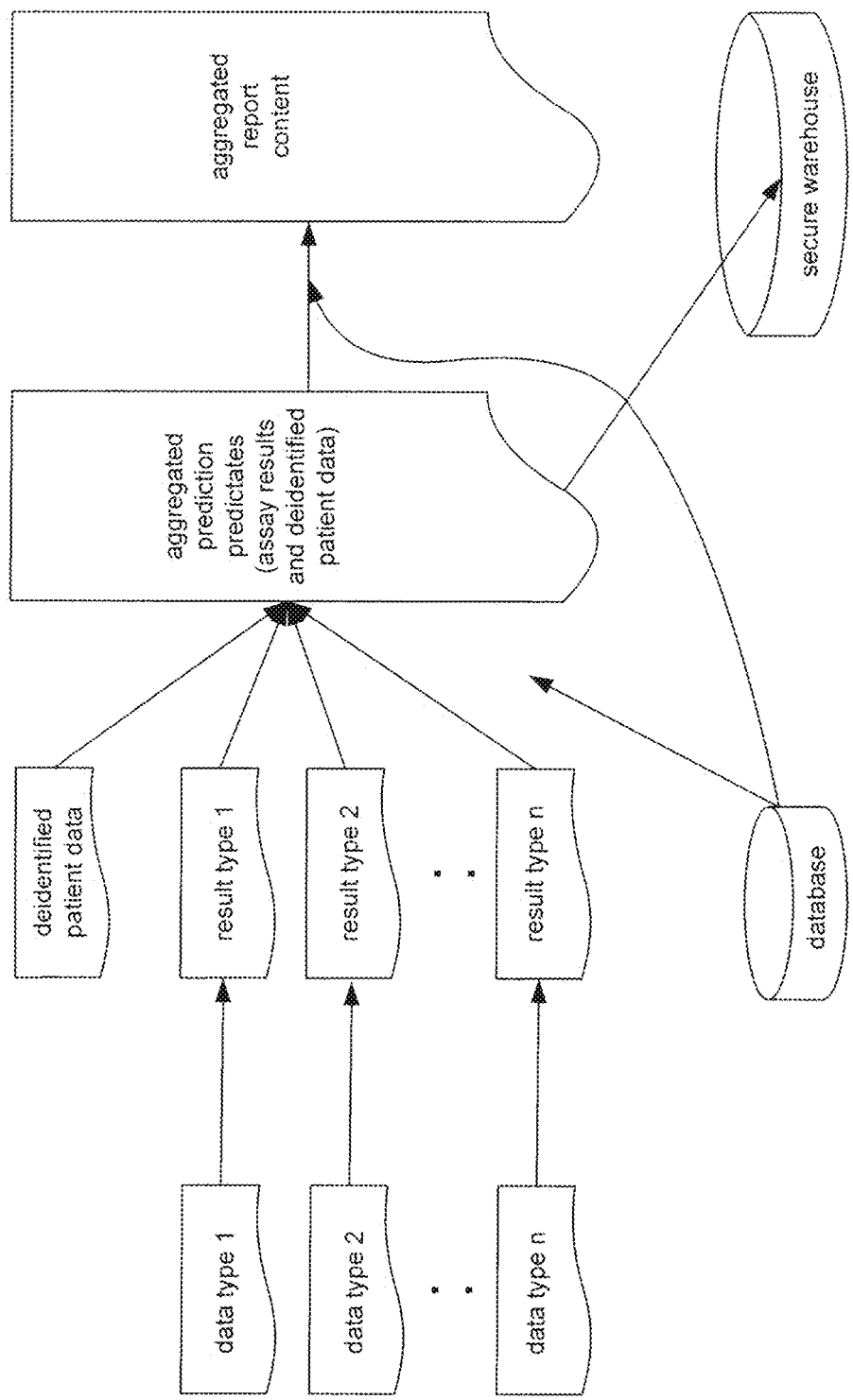
FIG. 10 is a flowchart illustrating an example of a system according to certain aspects of the invention as it relates to selective aggregation of results of laboratory analysis relevant to a requisition and generation of the applicable clinical report in response to such requisition.

In certain embodiments of the invention, analysis is conducted from a combination of data sources such as data from one or more laboratory workflows to derive attributes which are associated with phenotypic state, for example as illustrated in FIG. 9. Such analysis form multiple workflows may involve analysis from a combination of tissue/sample types such as one or more of the following: (i) germline genetic variants derived from analyzing genomic and/or mitochondrial DNA derived from one or more of normal tissue, blood samples, saliva samples, other sources, or genetic variants obtained from various other platforms (e.g., real-time PCR, array hybridization, fragment analysis methods, mass spec, DNA sequencing), (ii) somatic genetic variants derived from analyzing genomic and/or mitochondrial DNA derived from one or more of normal tissue, neoplastic (tumor) cells, or genetic variants obtained from various other platforms (e.g., real-time PCR, array hybridization, fragment analysis methods, mass spec, DNA sequencing), or (iii) germline genetic variants derived from analyzing coding DNA (cDNA) derived from one or more of normal tissue, blood samples, saliva samples, other sources, or genetic variants obtained from various other platforms (e.g., real-time PCR, array hybridization, fragment analysis methods, mass spec, DNA sequencing), (iv) somatic genetic variants derived from analyzing coding DNA (cDNA) derived from one or more of normal tissue, neoplastic (tumor) cells, or genetic variants obtained from various other platforms (e.g., real-time PCR, array hybridization, fragment analysis methods, mass spec, DNA sequencing), (v) gene expression levels derived from analyzing mRNA or cDNA derived from one or more of normal tissue, neoplastic (tumor) cells, or gene expression levels obtained from various other platforms (e.g., real-time PCR, array hybridization, fragment analysis methods, mass spec, DNA sequencing).

Data Marshalling

Certain elements comprise a data management element 12 that receives test results and that sorts and cross-references the tests results. Data element 12 can maintain clinically relevant information associated with requisitioned conditions/markers that are then served up to the results delivery element 13. Data element 12 can also hold "keys" to uninterpreted data that can be called on by the requisition engine 10. Responsive to a subsequent request forwarded by requisition engine 10, data element 12 can cause the Analysis Engine to interpret the appropriate sequence, thereby producing additional results that can be provided to the client.

Repository

In certain embodiments, repository 17 comprises one or more databases that store the raw data obtained from the test and analysis processes, as well as clinical data from the Data Menu. Clinical data is typically rendered anonymous. Repository database can typically be accessed by outside collaborators, according to their distinct access rights, through portal 18. In some embodiments, portions of the information in the Repository databases may be visible to the general public through a module in the portal 18. In certain embodiments of the invention, the repository may contain some or all of the following: (i) Sample-derived data including (x) attribute data (such as variant calls and expression levels) produced using the methods of the invention described herein and or produced by a third party and (y) genomic variants and sequence data not limited to known loci associated with genetic conditions; (ii) sample metadata including ethnicity, age, gender, geographical origin, risk behaviors, and or environmental influences; (iii) sample-associated phenotype information such as disease status, qualitative trait assessments (e.g., description of symptoms), quantitative trait assessments (e.g., blood pressure, lung capacity, blood marker levels), and or current Rx prescriptions; (iv) study metadata such as information associated with the client or collaborator producing the samples, and or study name, purpose, and experimental design.

In certain embodiments, the repository permits mining of one or more of its databases for novel associations between genetic variation or other attributes and phenotypes. Algorithms suitable for data-mining the repository may include, but are not limited to the following: linear regression, logistic regression, classification trees, hierarchical clustering, k-means clustering, Bayesian networks, neural networks, and support vector machines.

In certain embodiments, the repository permits the ability to associate multiple attributes, across attribute types, with a phenotypic likelihood score. In certain embodiments, the repository permits the ability to condition this score based on sample metadata such as age or ethnicity and the repository may provide for the graphical description of this score using methods such as box-and-whisker plots or histograms. The lack of an association between a phenotype and certain attributes can be used as information that a given phenotype might be more complex or less directly linked to molecular signatures of the associated attributes.

In certain embodiments, the repository permits the ability to mine the database for quality control purposes such as quality control in connection with the clinical diagnostic process. Associations present in the repository database can be tested against known associations from the curation database to check the veracity or either the curation database or the results presenting such associations. In certain embodiments, statistical measures of the data are compared with comparable studies and cohorts to verify the integrity of the data generation process.

In certain embodiments the repository is configured to permit access by third party researchers where access to the repository is limited to samples and information which has been approved for research use. Access to the repository and its contents may possess different levels of access and control for different users. In certain embodiments, levels of access and control can be restricted for certain populations of users of the repository to one or more of the following categories: (i) genomic locations only, (ii) genomic locations and alleles only, (iii) genomic locations, alleles and associated risk models, (iv) data restricted by conditions (for example, CF only), (v) data restricted by category of conditions (for example, rare Mendelian disorders only), (vi) data restricted by legal constraints (for example, non-patented gene tests only), and or (vii) data restricted by arbitrary sets as defined by Locus or third parties.

Data in the repository may be restricted to authorized clients as defined by contractual agreements. For example, some clients may be permitted to view all data which has been made "available for research purposes". The repository can be configured so that authorized individuals can have access to all of the data. The data repository can be configured to not store any identifying information for samples (e.g. patient names or dates of birth), as needed by regulations and the desired or required level of privacy. Access and control with respect to the repository or parts thereof may also be configured to enable different levels of access and control depending upon the identity of the client and the role of persons within the client (e.g. principal investigators, technicians, etc.). Role-based access to the repository may include controlled access to any or all of functions such as (i) searching the repository, (ii) types of information returned (loci only, assays and loci, condition information only), (iii) adding items to the data repository, and or (iv) deleting items from the data repository, (v) modifying items in the data repository. Users of the repository may have their level of access or control determined by their designated role and the level of access and control associated with such role. A user may be associated with an account profile (e.g., comprising user name, password, institution, contact information, access levels, etc.) which may be stored with the repository and define the levels of access permitted for that user. Levels of access and control with respect to databases of the invention including the repository may also be designated with respect to automated access performed by software agents.

Delivery

In certain embodiments, delivery module 13 processes clinical data for each condition/marker received from the data module 12. Clinical data and results can be formatted according to client preferences, indicated by the Requisition Engine 10. For example, different clients may want to utilize different markers for the same condition, or test more or fewer genes for a condition of interest. While the information in the data element 12 is comprehensive, the information served in the delivery module 13 is typically tailored to client specifications.

Client Data Integration

In certain embodiments, a Lab Report is delivered in a manner pre-determined for each client. Software and hardware combinations are provided that enable the information from the delivery element 13 to be transferred to the client's EMR system, to a physician/patient portal, to a company portal, and/or to a fax processing system. Certain elements of the system may be directly integrated into client systems. Included in the integration may be background or threshold notification handlers and a module for supporting client re-requisitions.

In certain embodiments of the invention, the invention permits a client who wishes to contact an expert in the field related to a test result or analysis they have received from the delivery element 13 and/or are accessing through the Collaborator Portal element 18. Through the Collaborator Portal and/or any other software or information service the client may be connected with an expert based on the marker(s), set of genome coordinates, variant(s), gene(s), condition(s), and/or group(s) of conditions of interest Collaborator Portal As noted above, certain embodiments provide collaborators with access to data in the repository 17. Collaborators can access data from the Locus Database or other databases, including repository databases controlled by certain specific permissions and privileges. Certain collaborators can be provided access to upload curation information into the Locus Database supplemental to curation tools embodied in the system. In some embodiments, certain specific condition/marker information can be made available for public viewing, typically in support of ongoing research. In certain embodiments selective access to the curation database may be granted to experts in the field, collaborators or clients to participate in the curation process by uploading, entering, suggesting or commenting on variants, genes, markers and/or conditions through software tools or a 'wiki' in the portal or otherwise made available. Additionally, access to aspects of certain curation databases may be granted to experts in the field, collaborators or clients to comment, rank, prioritize or otherwise give input on information in the database through software tools or a 'wiki' in the portal or otherwise made available.

System Description

Figure 3:
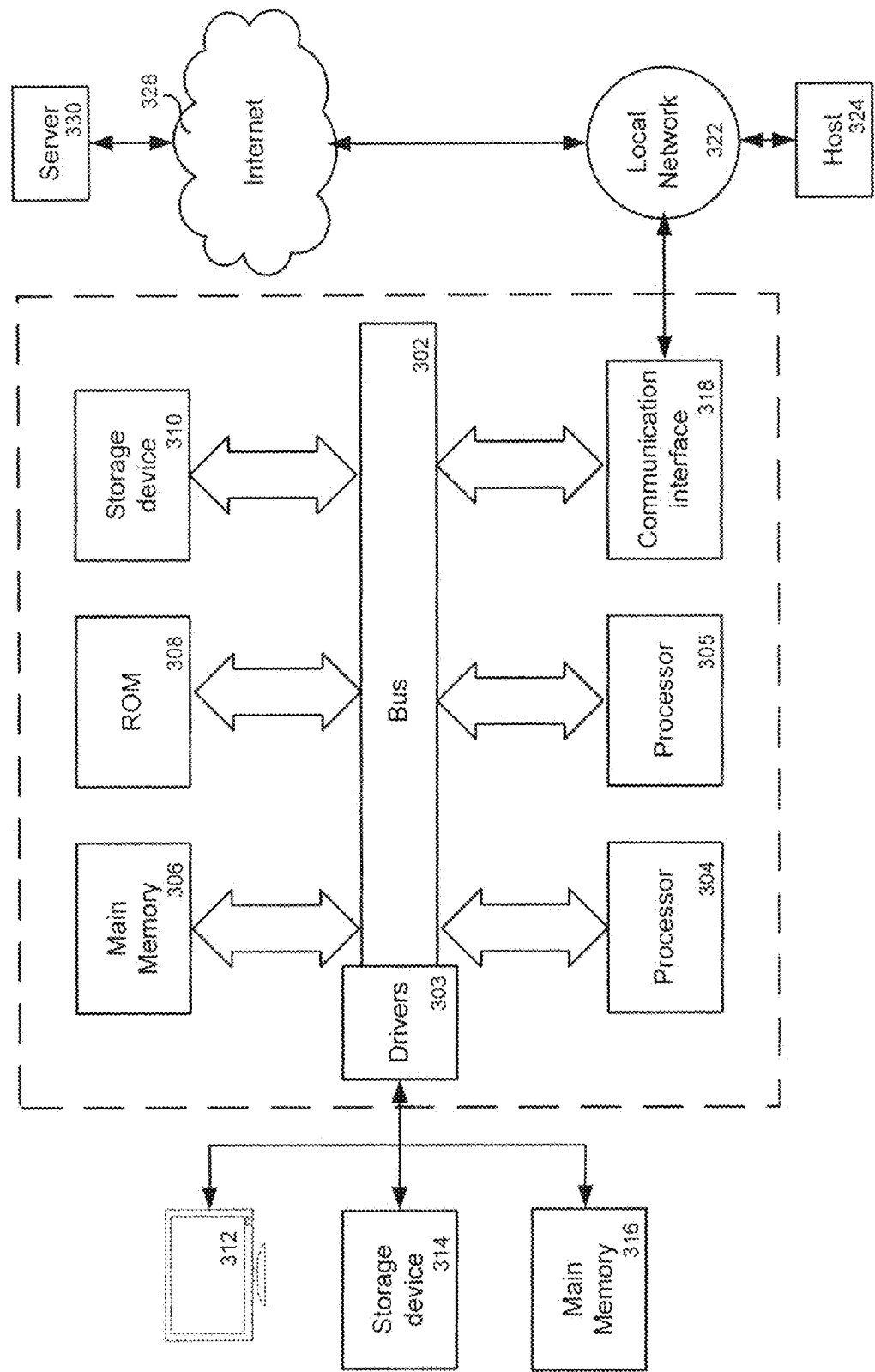
FIG. 3 is a block schematic of a simplified example of a computer system employed in certain embodiments of the invention.

Turning now to FIG. 3, certain embodiments of the invention employ a processing system that includes at least one computing system 300 deployed to perform certain of the steps described above. Computing systems may be a commercially available system that executes commercially available operating systems such as Microsoft Windows®, UNIX or a variant thereof, Linux, a real time operating system and or a proprietary operating system. The architecture of the computing system may be adapted, configured and/or designed for integration in the processing system, for embedding in one or more of an image capture system, a manufacturing/machining system and/or a graphics processing workstation. In one example, computing system 300 comprises a bus 302 and/or other mechanisms for communicating between processors, whether those processors are integral to the computing system 30 (e.g. 304, 305) or located in different, perhaps physically separated computing systems 300. Device drivers 303 may provide output signals used to control internal and external components Computing system 300 also typically comprises memory 306 that may include one or more of random access memory ("RAM"), static memory, cache, flash memory and any other suitable type of storage device that can be coupled to bus 302. Memory 306 can be used for storing instructions and data that can cause one or more of processors 304 and 305 to perform a desired process. Main memory 306 may be used for storing transient and/or temporary data such as variables and intermediate information generated and/or used during execution of the instructions by processor 304 or 305. Computing system 300 also typically comprises non-volatile storage such as read only memory ("ROM") 308, flash memory, memory cards or the like; non-volatile storage may be connected to the bus 302, but may equally be connected using a high-speed universal serial bus (USB), Firewire or other such bus that is coupled to bus 302. Non-volatile storage can be used for storing configuration, and other information, including instructions executed by processors 304 and/or 305. Non-volatile storage may also include mass storage device 310, such as a magnetic disk, optical disk, flash disk that may be directly or indirectly coupled to bus 302 and used for storing instructions to be executed by processors 304 and/or 305, as well as other information.

Computing system 300 may provide an output for a display system 312, such as an LCD flat panel display, including touch panel displays, electroluminescent display, plasma display, cathode ray tube or other display device that can be configured and adapted to receive and display information to a user of computing system 300. Typically, device drivers 303 can include a display driver, graphics adapter and/or other modules that maintain a digital representation of a display and convert the digital representation to a signal for driving a display system 312. Display system 312 may also include logic and software to generate a display from a signal provided by system 300. In that regard, display 312 may be provided as a remote terminal or in a session on a different computing system 300. An input device 314 is generally provided locally or through a remote system and typically provides for alphanumeric input as well as cursor control 316 input, such as a mouse, a trackball, etc. It will be appreciated that input and output can be provided to a wireless device such as a PDA, a tablet computer or other system suitable equipped to display the images and provide user input.

According to one embodiment of the invention, Processor 304 executes one or more sequences of instructions. For example, such instructions may be stored in main memory 306, having been received from a computer-readable medium such as storage device 310. Execution of the sequences of instructions contained in main memory 306 causes processor 304 to perform process steps according to certain aspects of the invention. In certain embodiments, functionality may be provided by embedded computing systems that perform specific functions wherein the embedded systems employ a customized combination of hardware and software to perform a set of predefined tasks. Thus, embodiments of the invention are not limited to any specific combination of hardware circuitry and software.

The term "computer-readable medium" is used to define any medium that can store and provide instructions and other data to processor 304 and/or 305, particularly where the instructions are to be executed by processor 304 and/or 305 and/or other peripheral of the processing system. Such medium can include non-volatile storage, volatile storage and transmission media. Non-volatile storage may be embodied on media such as optical or magnetic disks, including DVD, CD-ROM and BluRay. Storage may be provided locally and in physical proximity to processors 304 and 305 or remotely, typically by use of network connection. Non-volatile storage may be removable from computing system 304, as in the example of BluRay, DVD or CD storage or memory-cards or sticks that can be easily connected or disconnected from a computer using a standard interface, including USB, etc. Thus, computer-readable media can include floppy disks, flexible disks, hard disks, magnetic tape, any other magnetic medium, CD-ROMs, DVDs, BluRay, any other optical medium, punch cards, paper tape, any other physical medium with patterns of holes, RAM, PROM, EPROM, FLASH/EEPROM, any other memory chip or cartridge, or any other medium from which a computer can read.

Transmission media can be used to connect elements of the processing system and/or components of computing system 300. Such media can include twisted pair wiring, coaxial cables, copper wire and fiber optics. Transmission media can also include wireless media such as radio, acoustic and light waves. In particular radio frequency (RF), fiber optic and infrared (IR) data communications may be used.

Various forms of computer readable media may participate in providing instructions and data for execution by processor 304 and/or 305. For example, the instructions may initially be retrieved from a magnetic disk of a remote computer and transmitted over a network or modem to computing system 300. The instructions may optionally be stored in a different storage or a different part of storage prior to or during execution.

Computing system 300 may include a communication interface 318 that provides two-way data communication over a network 320 that can include a local network 322, a wide area network or some combination of the two. For example, an integrated services digital network (ISDN) may used in combination with a local area network (LAN). In another example, a LAN may include a wireless link. Network link 320 typically provides data communication through one or more networks to other data devices. For example, network link 320 may provide a connection through local network 322 to a host computer 324 or to a wide are network such as the Internet 328. Local network 322 and Internet 328 may both use electrical, electromagnetic or optical signals that carry digital data streams.

Computing system 300 can use one or more networks to send messages and data, including program code and other information. In the Internet example, a server 330 might transmit a requested code for an application program through Internet 328 and may receive in response a downloaded application that provides for the anatomical delineation described in the examples above. The received code may be executed by processor 304 and/or 305.

Additional Descriptions of Certain Aspects of the Invention

The foregoing descriptions of the invention are intended to be illustrative and not limiting. For example, those skilled in the art will appreciate that the invention can be practiced with various combinations of the functionalities and capabilities described above, and can include fewer or additional components than described above. Certain additional aspects and features of the invention are further set forth below, and can be obtained using the functionalities and components described in more detail above, as will be appreciated by those skilled in the art after being taught by the present disclosure.

Certain embodiments of the invention provide systems and methods for analyzing diagnostic information. Certain of these embodiments extract genomic DNA from a sample. Certain of these embodiments obtain sequence data for a plurality of markers. In certain embodiments, the plurality of markers include markers associated with one or more tests identified in a requisition corresponding to the sample. Certain of these embodiments generate a response to the requisition. In certain embodiments, the response is limited to an analysis of sequence data corresponding to the one or more tests. Certain of these embodiments assign an identifier to the sequence data. In certain embodiments, the identifier identifies the sample, the requisition and information related to the analysis. Certain of these embodiments store the sequence data in a repository of data. In certain embodiments, the repository provides data for analysis. Certain of these embodiments report additional results of an analysis of the sequence data in response to a second requisition. In certain embodiments, the second requisition identifies a test different from the one or more tests.

In certain embodiments, assigning an identifier includes rendering the source of the sample and the requisition anonymous. In certain embodiments, the second requisition includes the identifier. In certain embodiments, the information related to the analysis identifies the date of the analysis. In certain embodiments, generating a response to the requisition includes performing quality control on the results of an analysis of the sequence data. In certain embodiments, performing quality control includes performing a comparison using quality information derived from the repository. In certain embodiments, performing quality control includes updating the quality information using the results of the analysis of the sequence data. In certain embodiments, the repository is accessible to contributors through a portal. Certain of these embodiments update the repository based on contributions made by the contributors.

In certain embodiments of the invention, systems comprise a sample processing production line. In certain embodiments, the production line includes a genomic DNA extractor configured to extract DNA from a biological sample. In certain embodiments, the production line includes a target amplifier configured to amplify components of the extracted DNA. In certain embodiments, the production line includes a sequencer that produces sequence data for a plurality of markers from the amplified components. In certain embodiments, the plurality of markers includes markers associated with one or more tests identified in a requisition received with the sample. Certain of these embodiments comprise a sample information management system (SIMS) that controls processing of the sample by processing production line and analysis of the results of the processing of the sample. Certain of these embodiments comprise a quality control (QC) database that provides the SIMS with QC information. In certain embodiments, the SIMS uses the QC information to validate the processing of the sample and the analysis of the results. Certain of these embodiments comprise a repository comprising one or more databases. In certain embodiments, the repository aggregates the results generated by processing a plurality of samples. In certain embodiments, the repository includes the quality control database and a research database. Certain of these embodiments comprise an analyzer that generates the results using information in the repository.

In certain embodiments, information identifying a source of the sample is removed from the sample, the requisition and the results. In certain embodiments, the SIMS controls the processing and analysis of the system using a unique identifier assigned to the sample, the requisition and the results. In certain embodiments, a subset of the results are delivered to the source of the sample. In certain embodiments, the subset of results corresponds to a set of tests identified in the requisition. In certain embodiments, the subset of the results and additional results are maintained in the repository. In certain embodiments, the additional results are aggregated in the research database.

Certain of these embodiments comprise a portal that selectively provides access to data in the research database to a plurality of contributors. In certain embodiments, the portal communicates with the plurality of contributors via a public network. In certain embodiments, certain of the contributors provide additional research data to the research database. Certain of these embodiments comprise a data curator configured for use by the plurality of contributors. Certain of these embodiments comprise a data curator configured to process information provided to the research database. In certain embodiments, the information provided to the research database is obtained from public sources.

Certain embodiments of the invention include methods performed on a computer system that controls production line operations, analyzes physical results of the process, manages databases and/or gateways and portals or that controls intake of physical samples.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

Certain aspects of the invention are further illustrated by the following examples which simulate application of the invention to several hypothetical requisitions.

EXAMPLE 1

Cystic Fibrosis and Modifiers Variant Requisition

In one example, a requisition is submitted for Cystic Fibrosis. The requisition originates from any of a clinician, company, partner, or individual. The requisition is submitted electronically, on paper, via web service, from an EMR/PHR, or other means. The sample [any of blood, saliva, or cells, etc.] is de-identified and an encrypted ID is assigned. DNA from the sample associated with the requisition is purified and quality assessed for downstream processing. The sample is prepared for sequencing with respect to the regions of interest as defined by the Curation Database. All sequences relevant to any curated loci of interest and/or genes relevant for conditions of interest is targeted for downstream sequencing by a combination of targeting methodologies, in this case by targeted hybridization and 'pull down' of selected regions in addition to targeted amplification of selected regions. The sequencing is performed with one or more sequencing/analysis platforms and quality monitored for per base, per locus, coordinate, and condition quality statistics, ultimately enabling sensitivity, specificity and accuracy statistics to be resolved on a per base, locus, coordinate or condition basis. The Requisition Engine performs the secondary analysis on the regions of interest as indicated by the client in the sample requisition, in this case variants that are known, novel and variants of unknown significance in the CFTR, MBL2 and TGFB1 genes which allows reporting on Cystic Fibrosis and known modifiers of Cystic Fibrosis as determined by the Locus Database. The client/patient ID informs the regions for the Analysis Engine to interpret and per-condition results are determined. The data for the results are made available to be delivered as any of a PDF, API for integration into electronic records, or fax, etc.] as per client's instruction. In this case, the client's preferences are to receive results for known pathogenic variants, as well as novel variants and variants of unknown significance. The data may be used by the client directly, or reformatted into a clinical report summarizing the key information for a patient.

TABLE 1

| Requisition | | | | | |
|---|---|---|---|---|---|
| | PATIENT | | SPECIMEN | | CONFIDENTIAL [UPC Code] PHYSICIAN |
| Name: | Patient 0 | Lab #: | LocDev000001 | | Dr. Feelgood |
| DOB: | Sept. 30, 1973 | Specimen type: | DNA | | 123 University Dr. |
| MRN: | JK69503 | Sample received: | 02/03/2012 | | Room 301 |

TABLE 1-continued

| Requisition | | | | |
|---|---|---|---|---|
| Gender: | Female | Report date: | 02/04/2012 | Los Angeles, CA 90025 |
| Race: | Asian | | | |

| Order Details | | | | |
|---|---|---|---|---|
| Ordered Condition | Reported Conditions | Genes | Qualitative Report (Select all that apply for each ordered condition) | Quantitative Report (Threshold for reporting summary findings) |
| ☒ Cystic fibrosis  *Note: submission of parental samples may facilitate interpretation | Congenital bilateral absence of the vas deferens Cystic fibrosis Cystic fibrosis, modifier MBL2 Cystic fibrosis, modifier TGFB1 Modifier of CFTR related conditions* | CFTR MBL2 TGFB1 | ☒ Pathogenic variants (known) ☒ Pathogenic variants (novel) ☒ Variants of unknown significance ☐ Sequence data | Not applicable |

TABLE 2

Summary Results

Summary Results

| Congenital bilateral absence of the vas deferens | NOT AT RISK: 0 pathogenic variants |
|---|---|

| Cystic fibrosis | | | AT RISK 2 pathogenic variants (Risk Model Autosomal Recessive) | | |
|---|---|---|---|---|---|
| Variant Name | Alias | Known (PMID) or Novel | Ref Allele | Patient Genotype | Findings |
| NM_000492.3: c.11C > A | S4X | Known (*) | C | A\|A | 2 pathogenic alleles |

(*) URL and Access Date: www.genet.sickkids.on.ca/Home.html 20101209

| Cystic fibrosis, modifier MBL2 | | At risk of reduced survival | |
|---|---|---|---|
| Variant Name | Known (PMID/URL) or Novel | Patient Diplotype | Findings |
| HapO_a HapO_b | Known (17158822) Known (17158822) | HapO_a\|HapO_b | 2 risk haplotypes |

| Cystic fibrosis, modifier TGFB1 | | Higher lung function | |
|---|---|---|---|
| Variant Name | Known (PMID/URL) or Novel | Patient Diplotype | Findings |
| Hap2 Hap4 | Known (16896927) Known (16896927) | Hap2\|Hap4 | 2 risk haplotypes |

| Modifier of CFTR related conditions* | | | Genotype Report | | |
|---|---|---|---|---|---|
| Variant Name | Alias | Known (PMID) or Novel | Ref Allele | Patient Genotype | Findings |
| NM_000492.3: c.1210-12T(5_9) | polyT tract | Known (7739684) | T(7) | T(5)\|T(5) | 2 non-ref alleles |
| NM_000492.3: c.1210-34_33TG(8_13) | polyTG tract | Known (16020494) | TG(11) | TG(9)\|TG(9) | 2 non-ref alleles |
| NM_000492.3: c.350G > A | R117H | Known (15371902) | A | A\|A | 0 non-ref alleles |

Note: This test is best interpreted when phase is known. Consider submitting parental samples.
Kaiser Comprehensive-Screen    NOT AT RISK
Negative for pathogenic variants
Negative for >40% residual lifetime risk

TABLE 3

Detailed Findings

Detailed Findings
Assay Methodology

Figure 11:
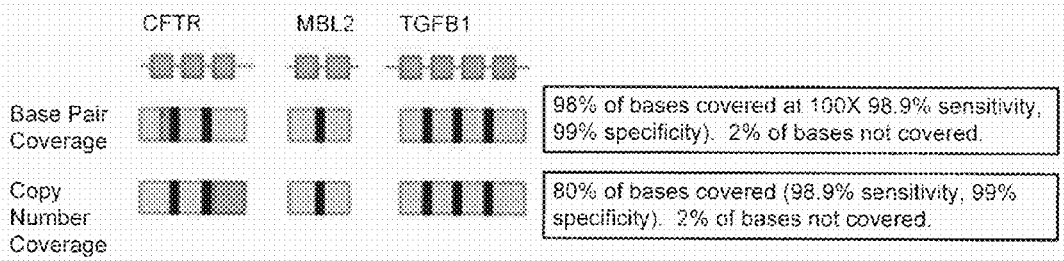
FIG. 11 is a diagram depicting assay performance with respect to genes CFTR, MBL2 and TGFB1 in Example 1.

PCR amplicons were designed to all coding exons + 2bp intron/exon boundary
and any previously observed pathogenic locus. Amplicons were amplified in patient
DNA using PCR and sequenced using the 454 Jr. Sequencer and copy number variants
relative to the reference genome GRCh37 (alias HG19) were determined using GATK.
Assay Performance FIG. 11 depicts the assay performance for CFTR, MBL2, and TGFB1 genes.

|  | GRCh37 Bases Covered (Green) | GRCh37 Bases Not Covered (Red) |
|---|---|---|
| Sequence Coverage | 7:400_440, 7:800_803, 7:810_900, 7:1000_1200 10:100_140, 10:160_210, 10:220_240 19:150_300, 19:325_500 | 7:804_809 |
| Copy Number Coverage | 7:400_440, 7:800_803, 7:810_900, 7:1000_1200 10:100_140, 10:160_210, 10:220_240 19:150_300, 19:325_500 | 7:1000_1200 |

Sequence Results
Congenital bilateral absence of the vas deferens
Variants of Unknown Significance

| Variant Name | Effect | Ref Allele | Patient Genotype | Number of Non-Reference Alleles | Observed in Affected Individuals (PMID) | Frequency of Patient Genotype in 1000 Genomes | Evolutionary Conservation Score | Splice Prediction Score |
|---|---|---|---|---|---|---|---|---|
| NM_000492.3: c.4046G > A | Missense | G | A\|G | 1 | Known (*) | 0.01% | Probably damaging | Detrimental |
| NM_000492.3: c.3915T > A | Missense | T | A\|T | 1 | Known (*) | 0.01% | Probably damaging | Detrimental |

(*) URL and Access Date: www.genet.sickkids.on.ca/Home.html 20101209

Cystic fibrosis
Known Pathogenic Variants - Positive or No Data

| Variant Name | Alias or Protein Change | Effect | Reference Allele | Patient Genotype | Findings | Reference (URL or PMID) |
|---|---|---|---|---|---|---|
| NM_000492.3: c.11C > A | S4X | nonsense | C | A\|A | 2 pathogenic alleles | * |

Variants of Unknown Significance

| Variant Name | Effect | Ref Allele | Patient Genotype | Number of Non-Reference Alleles | Observed in Affected Individuals (PMID) | Frequency of Patient Genotype in 1000 Genomes | Evolutionary Conservation Score | Splice Prediction Score |
|---|---|---|---|---|---|---|---|---|
| NM_000492.3: c.2249C > T | Missense | C | T\|C | 1 | Known (*) | 0.01% | Probably damaging | Detrimental |
| NM_000492.3: c.2251C > G | Missense | C | C\|G | 1 | Unknown | 10% | Benign | No effect |

(*) URL and Access Date: www.genet.sickkids.on.ca/Home.html 20101209

Cystic fibrosis, modifier MBL2
Known Pathogenic Variants

| Variant Name | Alias or Protein Change | Effect | Ref Allele | Patient Genotype | Findings | Reference (URL or PMID) |
|---|---|---|---|---|---|---|
| Alleles | | | | | | |
| NM_000242.2: c.154C > T | MBL2*D | Part of a haplotype | G | G\|A | 1 non-ref allele | 17158822 |
| NM_000242.2: c.161G > A | MBL2*B | Part of a haplotype | C | C\|T | 1 non-ref allele | 17158822 |
| NM_000242.2: c.170G > A | MBL2*C | Part of a haplotype | C | C\|C | 0 non-ref alleles | 17158822 |
| Haplotypes | | | | | | |
| MBL2 Haplotype O_a | | Low MBL2 protein level | ACC | ACC | 1 risk haplotype | 17158822 |
| MBL2 Haplotype O_b | | Low MBL2 protein level | GTC | GTC | 1 risk haplotype | 17158822 |
| MBL2 Haplotype O_c | | Low MBL2 protein level | GCT | | 0 risk haplotypes | 17158822 |
| MBL2 Haplotype A | | Normal activity | GCC | | 0 nonrisk haplotypes | 17158822 |
| Patient Diplotype | | | | HapO_a\|HapO_b | Reduced survival | |

TABLE 3-continued

Cystic fibrosis, modifier TGFB1
Known Pathogenic Variants

| Variant Name | Alias or Protein Change | Effect | Ref Allele | Patient Genotype | Findings | Reference (URL or PMID) |
|---|---|---|---|---|---|---|
| Alleles | | | | | | |
| NC_000019.9: g.41860296G > A | TGFB1-509 promoter | Part of a haplotype | G | G\|A | 1 non-ref allele | 16896927 |
| NM_000660.4: c.29C > T | TGFB1-codon10 | Part of a haplotype | A | A\|G | 1 non-ref allele | 16896927 |
| | TGFB1-intron5 | Part of a haplotype | G | G\|G | 0 non-ref alleles | 16896927 |
| Haplotypes | | | | | | |
| TGFB1 Haplotype Hap2 | | Normal TGFB1 levels | GAG | GAG | 1 risk haplotype | 16896927 |
| TGFB1 Haplotype Hap4 | | Increased plasma TGFB1 levels | AGG | AGG | 1 risk haplotype | 16896927 |
| TGFB1 Haplotype Hap1 | | Normal TGFB1 levels | GGG | | 0 unknown* haplotypes | 16896927 |
| TGFB1 Haplotype Hap3 | | Normal TGFB1 levels | GAA | | 0 unknown* haplotypes | 16896927 |
| TGFB1 Haplotype Hap5 | | Increased plasma TGFB1 levels | AGA | | 0 unknown* haplotypes | 16896927 |
| Patient Diplotype | | | | Hap2\|Hap4 | Higher lung function | |

*Unknown = no published information on genotype:phenotype relationship

Cystic fibrosis
Known Pathogenic Variants - Negative Results

| Variant Name | Alias or Protein Change | Effect | Reference Allele | Patient Genotype | Findings | Reference (URL or PMID) |
|---|---|---|---|---|---|---|
| NM_000492.3: c.1086T > A | NP_000483.3: p.Tyr362* | nonsense | T | T\|T | 0 pathogenic alleles | * |
| NM_000492.3: c.1116 + 1G > A | 1248 + 1G->A | consensus splice | G | G\|G | 0 pathogenic alleles | * |
| NM_000492.3: c.1117 − 1G > A | | consensus splice | G | G\|G | 0 pathogenic alleles | * |
| NM_000492.3: c.1202G > A | W401X(TAG) | nonsense | G | G\|G | 0 pathogenic alleles | * |
| NM_000492.3: c.1203G > A | W401X(TGA) | nonsense | G | G\|G | 0 pathogenic alleles | * |
| NM_000492.3: c.1392 + 1G > A | 1524 + 1G->A | consensus splice | G | G\|G | 0 pathogenic alleles | * |
| NM_000492.3: c.1393 − 1G > A | 1525 − 1G->A | consensus splice | G | G\|G | 0 pathogenic alleles | * |
| NM_000492.3: c.1397C > A | S466X(TAA) | nonsense | C | C\|C | 0 pathogenic alleles | * |
| NM_000492.3: c.1466C > A | S489X | nonsense | C | C\|C | 0 pathogenic alleles | * |
| NM_000492.3: c.1487G > A | W496X | nonsense | G | G\|G | 0 pathogenic alleles | * |
| NM_000492.3: c.1572C > A | C524X | nonsense | C | C\|C | 0 pathogenic alleles | * |
| NM_000492.3: c.1584 + 1G > A | 1716 + 1G->A | consensus splice | G | G\|G | 0 pathogenic alleles | * |
| NM_000492.3: c.1585 − 1G > A | 1717 − 1G->A | consensus splice | G | G\|G | 0 pathogenic alleles | * |
| NM_000492.3: c.164 + 1G > A | 296 + 1G->A | consensus splice | G | G\|G | 0 pathogenic alleles | * |
| NM_000492.3: c.164 + 2T > A | 296 + 2T->A | consensus splice | T | T\|T | 0 pathogenic alleles | * |
| NM_000492.3: c.1680 − 1G > A | 1812 − 1G->A | consensus splice | G | G\|G | 0 pathogenic alleles | * |
| NM_000492.3: c.1707T > A | Y569X | nonsense | T | T\|T | 0 pathogenic alleles | * |
| NM_000492.3: c.170G > A | W57X(TAG) | nonsense | G | G\|G | 0 pathogenic alleles | * |
| NM_000492.3: c.171G > A | W57X(TGA) | nonsense | G | G\|G | 0 pathogenic alleles | * |
| NM_000492.3: c.1766 + 1G > A | 1898 + 1G->A | consensus splice | G | G\|G | 0 pathogenic alleles | * |
| NM_000492.3: c.2036G > A | W679X | nonsense | G | G\|G | 0 pathogenic alleles | * |
| NM_000492.3: c.2156T > A | L719X | nonsense | T | T\|T | 0 pathogenic alleles | * |
| NM_000492.3: c.236G > A | W79X | nonsense | G | G\|G | 0 pathogenic alleles | * |
| NM_000492.3: c.2490 + 1G > A | 2622 + 1G->A | consensus splice | G | G\|G | 0 pathogenic alleles | * |
| NM_000492.3: c.2537G > A | W846X | nonsense | G | G\|G | 0 pathogenic alleles | * |
| NM_000492.3: c.2538G > A | W846X(2670TGG > TGA) | nonsense | G | G\|G | 0 pathogenic alleles | * |
| NM_000492.3: c.2547C > A | Y849X | nonsense | C | C\|C | 0 pathogenic alleles | * |
| NM_000492.3: c.2600T > A | L867X | nonsense | T | T\|T | 0 pathogenic alleles | * |
| NM_000492.3: c.2619 + 2T > A | 2751 + 2T->A | consensus splice | T | T\|T | 0 pathogenic alleles | * |
| NM_000492.3: c.263T > A | L88X(T->A) | nonsense | T | T\|T | 0 pathogenic alleles | * |
| NM_000492.3: c.2645G > A | W882X | nonsense | G | G\|G | 0 pathogenic alleles | * |
| NM_000492.3: c.273 + 1G > A | 405 + 1G->A | consensus splice | G | G\|G | 0 pathogenic alleles | * |
| NM_000492.3: c.2735C > A | S912X | nonsense | C | C\|C | 0 pathogenic alleles | * |
| NM_000492.3: c.2739T > A | Y913X | nonsense | T | T\|T | 0 pathogenic alleles | * |
| NM_000492.3: c.274 − 1G > A | 406 − 1G->A | consensus splice | G | G\|G | 0 pathogenic alleles | * |
| NM_000492.3: c.2909 − 1G > A | 3041 − 1G->A | consensus splice | G | G\|G | 0 pathogenic alleles | * |
| NM_000492.3: c.2988 + 1G > A | 3120 + 1G->A | consensus splice | G | G\|G | 0 pathogenic alleles | * |
| NM_000492.3: c.2989 − 1G > A | 3121 − 1G->A | consensus splice | G | G\|G | 0 pathogenic alleles | * |
| NM_000492.3: c.2T > A | M1K | initiator | T | T\|T | 0 pathogenic alleles | * |
| NM_000492.3: c.3139 + 1G > A | 3271 + 1G->A | consensus splice | G | G\|G | 0 pathogenic alleles | * |
| NM_000492.3: c.3140 − 1G > A | 3272 − 1G->A | consensus splice | G | G\|G | 0 pathogenic alleles | * |
| NM_000492.3: c.3189G > A | W1063X | nonsense | G | G\|G | 0 pathogenic alleles | * |
| NM_000492.3: c.3266G > A | W1089X | nonsense | G | G\|G | 0 pathogenic alleles | * |
| NM_000492.3: c.3276C > A | Y1092X(C->A) | nonsense | C | C\|C | 0 pathogenic alleles | * |

TABLE 3-continued

| | | | | | | |
|---|---|---|---|---|---|---|
| NM_000492.3: c.327T > A | Y109X | nonsense | T | T\|T | 0 pathogenic alleles | * |
| NM_000492.3: c.3293G > A | W1098X(TAG) | nonsense | G | G\|G | 0 pathogenic alleles | * |
| NM_000492.3: c.3368 − 1G > A | 3500 − 1GtoA | consensus splice | G | G\|G | 0 pathogenic alleles | * |
| NM_000492.3: c.3435G > A | W1145X | nonsense | G | G\|G | 0 pathogenic alleles | * |
| NM_000492.3: c.3611G > A | W1204X(3743G->A) | nonsense | G | G\|G | 0 pathogenic alleles | * |
| NM_000492.3: c.3612G > A | W1204X(3744G->A) | nonsense | G | G\|G | 0 pathogenic alleles | * |
| NM_000492.3: c.3617C > A | S1206X(C > A) | nonsense | C | C\|C | 0 pathogenic alleles | * |
| NM_000492.3: c.366T > A | Y122X | nonsense | T | T\|T | 0 pathogenic alleles | * |
| NM_000492.3: c.3717 + 1G > A | 3849 + 1G->A | consensus splice | G | G\|G | 0 pathogenic alleles | * |
| NM_000492.3: c.3718 − 1G > A | 3850 − 1G->A | consensus splice | G | G\|G | 0 pathogenic alleles | * |
| NM_000492.3: c.3764C > A | S1255X | nonsense | C | C\|C | 0 pathogenic alleles | * |
| NM_000492.3: c.3822G > A | W1274X | nonsense | G | G\|G | 0 pathogenic alleles | * |
| NM_000492.3: c.3846G > A | W1282X | nonsense | G | G\|G | 0 pathogenic alleles | * |
| NM_000492.3: c.3873 + 1G > A | 4005 + 1G->A | consensus splice | G | G\|G | 0 pathogenic alleles | * |
| NM_000492.3: c.3921T > A | Y1307X | nonsense | T | T\|T | 0 pathogenic alleles | * |
| NM_000492.3: c.3929G > A | W1310X | nonsense | G | G\|G | 0 pathogenic alleles | * |
| NM_000492.3: c.3947G > A | W1316X | nonsense | G | G\|G | 0 pathogenic alleles | * |
| NM_000492.3: c.3963 + 2T > A | 4095 + 2T->A | consensus splice | T | T\|T | 0 pathogenic alleles | * |
| NM_000492.3: c.3964 − 1G > A | 4096 − 1G->A | consensus splice | G | G\|G | 0 pathogenic alleles | * |
| NM_000492.3: c.3G > A | M1I(ATA) | initiator | G | G\|G | 0 pathogenic alleles | * |
| NM_000492.3: c.4143C > A | Y1381X | nonsense | C | C\|C | 0 pathogenic alleles | * |
| NM_000492.3: c.4242 + 1G > A | 4374 + 1G->A | consensus splice | G | G\|G | 0 pathogenic alleles | * |
| NM_000492.3: c.4272C > A | NP_000483.3: p.Tyr1424* | nonsense | C | C\|C | 0 pathogenic alleles | * |
| NM_000492.3: c.476T > A | L159X | nonsense | T | T\|T | 0 pathogenic alleles | * |
| NM_000492.3: c.490 − 1G > A | 622 − 1G->A | consensus splice | G | G\|G | 0 pathogenic alleles | * |
| NM_000492.3: c.57G > A | W19X | nonsense | G | G\|G | 0 pathogenic alleles | * |
| NM_000492.3: c.606G > A | W202X | nonsense | G | G\|G | 0 pathogenic alleles | * |
| NM_000492.3: c.647G > A | W216X | nonsense | G | G\|G | 0 pathogenic alleles | * |
| NM_000492.3: c.653T > A | L218X | nonsense | T | T\|T | 0 pathogenic alleles | * |
| NM_000492.3: c.675T > A | C225X | nonsense | T | T\|T | 0 pathogenic alleles | * |
| NM_000492.3: c.743 + 1G > A | 875 + 1G->A | consensus splice | G | G\|G | 0 pathogenic alleles | * |
| NM_000492.3: c.828C > A | C276X | nonsense | C | C\|C | 0 pathogenic alleles | * |
| NM_000492.3: c.938C > A | S313X | nonsense | C | C\|C | 0 pathogenic alleles | * |
| NM_000492.3: c.959T > A | L320X | nonsense | T | T\|T | 0 pathogenic alleles | * |
| NM_000492.3: c.1703T > A | L568X | nonsense | T | T\|T | 0 pathogenic alleles | * |
| NM_000492.3: c.3294G > A | W1098X(TGA) | nonsense | G | G\|G | 0 pathogenic alleles | * |
| NM_000492.3: c.1210 − 1G > C | 1342 − 1G->C | consensus splice | G | G\|G | 0 pathogenic alleles | * |
| NM_000492.3: c.1210-2A > C | 1342-2A->C | consensus splice | A | A\|A | 0 pathogenic alleles | * |
| NM_000492.3: c.1584 + 2T > C | 1716 + 2T->C | consensus splice | T | T\|T | 0 pathogenic alleles | * |
| NM_000492.3: c.1679 + 1G > C | 1811 + 1G->C | consensus splice | G | G\|G | 0 pathogenic alleles | * |
| NM_000492.3: c.1679 + 2T > C | | consensus splice | T | T\|T | 0 pathogenic alleles | * |
| NM_000492.3: c.1A > C | M1L | initiator | A | A\|A | 0 pathogenic alleles | * |
| NM_000492.3: c.2490 + 2T > C | 2622 + 2T > C | consensus splice | T | T\|T | 0 pathogenic alleles | * |
| NM_000492.3: c.2620 − 1G > C | 2752 − 1G->C | consensus splice | G | G\|G | 0 pathogenic alleles | * |
| NM_000492.3: c.2658 − 1G > C | 2790 − 1G->C | consensus splice | G | G\|G | 0 pathogenic alleles | * |
| NM_000492.3: c.274-2A > C | 406-2A->C | consensus splice | A | A\|A | 0 pathogenic alleles | * |
| NM_000492.3: c.2908 + 2T > C | 3040 + 2T->C | consensus splice | T | T\|T | 0 pathogenic alleles | * |
| NM_000492.3: c.2988 + 2T > C | | consensus splice | T | T\|T | 0 pathogenic alleles | * |
| NM_000492.3: c.3367 + 2T > C | 3499 + 2T->C | consensus splice | T | T\|T | 0 pathogenic alleles | * |
| NM_000492.3: c.3873 + 2T > C | 4005 + 2T->C | consensus splice | T | T\|T | 0 pathogenic alleles | * |
| NM_000492.3: c.3963 + 1G > C | 4095 + 1G->C | consensus splice | G | G\|G | 0 pathogenic alleles | * |
| NM_000492.3: c.4243 − 1G > C | 4375 − 1G->C | consensus splice | G | G\|G | 0 pathogenic alleles | * |
| NM_000492.3: c.4243-2A > C | 4375-2A->C | consensus splice | A | A\|A | 0 pathogenic alleles | * |
| NM_000492.3: c.489 + 2T > C | 621 + 2T->C | consensus splice | T | T\|T | 0 pathogenic alleles | * |
| NM_000492.3: c.490-2A > C | 622-2A->C | consensus splice | A | A\|A | 0 pathogenic alleles | * |
| NM_000492.3: c.1116 + 1G > C | 1248 + 1G->C | consensus splice | G | G\|G | 0 pathogenic alleles | * |
| NM_000492.3: c.164 + 1G > C | 296 + 1G->C | consensus splice | G | G\|G | 0 pathogenic alleles | * |
| NM_000492.3: c.164 + 2T > C | 296 + 2T->C | consensus splice | T | T\|T | 0 pathogenic alleles | * |
| NM_000492.3: c.1766 + 1G > C | 1898 + 1G->C | consensus splice | G | G\|G | 0 pathogenic alleles | * |
| NM_000492.3: c.274 − 1G > C | 406 − 1G->C | consensus splice | G | G\|G | 0 pathogenic alleles | * |
| NM_000492.3: c.2T > C | M1T | initiator | T | T\|T | 0 pathogenic alleles | * |
| NM_000492.3: c.743 + 1G > C | 875 + 1G->C | consensus splice | G | G\|G | 0 pathogenic alleles | * |
| NC_000007.13: g.117120140_117120162del23 | 124del23bp | initiator | ref | ref\|ref | 0 pathogenic alleles | * |
| NM_000492.3: c.1297_1313del | 1429del7bp | frameshift | ref | ref\|ref | 0 pathogenic alleles | * |
| NM_000492.3: c.1360_1387del | 1491-1500del | frameshift | ref | ref\|ref | 0 pathogenic alleles | * |
| NC_000007.13: g.117232144_117232152delCTCAAAATinsA | 2055del9->A | frameshift | ref | ref\|ref | 0 pathogenic alleles | * |
| NC_000007.13: g.117232194_117232206del13insAGAAA | 2105-2117del13insAGAAA | frameshift | ref | ref\|ref | 0 pathogenic alleles | * |
| NM_000492.3: c.3728_3758del | 3860ins31 | frameshift | ref | ref\|ref | 0 pathogenic alleles | * |
| NM_000492.3: c.4036_4042del | 4168delCTAAGCC | frameshift | ref | ref\|ref | 0 pathogenic alleles | * |
| NM_000492.3: c.1018delA | 1150delA | frameshift | ref | ref\|ref | 0 pathogenic alleles | * |
| NM_000492.3: c.1152delA | 1283delA | frameshift | ref | ref\|ref | 0 pathogenic alleles | * |
| NM_000492.3: c.1340delA | 1471delA | frameshift | ref | ref\|ref | 0 pathogenic alleles | * |
| NM_000492.3: c.156delA | 284delA | frameshift | ref | ref\|ref | 0 pathogenic alleles | * |
| NM_000492.3: c.1650delA | 1782delA | frameshift | ref | ref\|ref | 0 pathogenic alleles | * |

TABLE 3-continued

| | | | | | | |
|---|---|---|---|---|---|---|
| NM_000492.3: c.1656delA | 1787delA | frameshift | ref | ref|ref | 0 pathogenic alleles | * |
| NM_000492.3: c.1674delA | 1806delA | frameshift | ref | ref|ref | 0 pathogenic alleles | * |
| NM_000492.3: c.168delA | 300delA | frameshift | ref | ref|ref | 0 pathogenic alleles | * |
| NM_000492.3: c.1692delA | 1824delA | frameshift | ref | ref|ref | 0 pathogenic alleles | * |
| NM_000492.3: c.1976delA | 2108delA | frameshift | ref | ref|ref | 0 pathogenic alleles | * |
| NM_000492.3: c.1981delA | 2113delA | frameshift | ref | ref|ref | 0 pathogenic alleles | * |
| NM_000492.3: c.2052delA | 2184delA | frameshift | ref | ref|ref | 0 pathogenic alleles | * |
| NM_000492.3: c.2203delA | 2335delA | frameshift | ref | ref|ref | 0 pathogenic alleles | * |
| NM_000492.3: c.2896delA | 3028delA | frameshift | ref | ref|ref | 0 pathogenic alleles | * |
| NM_000492.3: c.2998delA | 3130delA | frameshift | ref | ref|ref | 0 pathogenic alleles | * |
| NM_000492.3: c.3106delA | 3238delA | frameshift | ref | ref|ref | 0 pathogenic alleles | * |
| NM_000492.3: c.310delA | 441delA | frameshift | ref | ref|ref | 0 pathogenic alleles | * |
| NM_000492.3: c.313delA | 444delA | frameshift | ref | ref|ref | 0 pathogenic alleles | * |
| NM_000492.3: c.3364delA | 3495delA | frameshift | ref | ref|ref | 0 pathogenic alleles | * |
| NM_000492.3: c.3540delA | 3670delA | frameshift | ref | ref|ref | 0 pathogenic alleles | * |
| NM_000492.3: c.3605delA | 3737delA | frameshift | ref | ref|ref | 0 pathogenic alleles | * |
| NM_000492.3: c.3744delA | 3876delA | frameshift | ref | ref|ref | 0 pathogenic alleles | * |
| NM_000492.3: c.3829delA | 3960-3961delA | nonsense | ref | ref|ref | 0 pathogenic alleles | * |
| NM_000492.3: c.3876delA | 4006delA | frameshift | ref | ref|ref | 0 pathogenic alleles | * |
| NM_000492.3: c.3883delA | 4015delA | frameshift | ref | ref|ref | 0 pathogenic alleles | * |
| NM_000492.3: c.4140delA | 4272delA | frameshift | ref | ref|ref | 0 pathogenic alleles | * |
| NM_000492.3: c.4170delA | 4301(4302?)delA | frameshift | ref | ref|ref | 0 pathogenic alleles | * |
| NM_000492.3: c.424delA | 556delA | frameshift | ref | ref|ref | 0 pathogenic alleles | * |
| NM_000492.3: c.4251delA | 4382delA | frameshift | ref | ref|ref | 0 pathogenic alleles | * |
| NM_000492.3: c.42delA | 174delA | frameshift | ref | ref|ref | 0 pathogenic alleles | * |
| NM_000492.3: c.526delA | 657delA | frameshift | ref | ref|ref | 0 pathogenic alleles | * |
| NM_000492.3: c.803delA | 935delA | frameshift | ref | ref|ref | 0 pathogenic alleles | * |
| NM_000492.3: c.987delA | 1119delA | frameshift | ref | ref|ref | 0 pathogenic alleles | * |
| NM_000492.3: c.3161delA | 3293delA | frameshift | ref | ref|ref | 0 pathogenic alleles | * |
| NM_000492.3: c.3530delA | 3662delA | frameshift | ref | ref|ref | 0 pathogenic alleles | * |
| NM_000492.3: c.3908delA | 4040delA | frameshift | ref | ref|ref | 0 pathogenic alleles | * |
| NM_000492.3: c.442delA | 574delA | frameshift | ref | ref|ref | 0 pathogenic alleles | * |
| NM_000492.3: c.2051_2052delAA | 2183delAA | frameshift | ref | ref|ref | 0 pathogenic alleles | * |
| NM_000492.3: c.881_882delAA | 1013delAA | frameshift | ref | ref|ref | 0 pathogenic alleles | * |
| NM_000492.3: c.1792_1798delAAACTA | 1924del7 | frameshift | ref | ref|ref | 0 pathogenic alleles | * |
| NM_000492.3: c.1986_1989delAACT | 2118del4 | frameshift | ref | ref|ref | 0 pathogenic alleles | * |
| NM_000492.3: c.859_863delAACTT | 991del5 | frameshift | ref | ref|ref | 0 pathogenic alleles | * |
| NM_000492.3: c.578_579 + 5delAAGTATG | 710_711 + 5del7 | splice site deletion | ref | ref|ref | 0 pathogenic alleles | * |
| NM_000492.3: c.2051_2052delAAinsG | 2183AA->G | frameshift | ref | ref|ref | 0 pathogenic alleles | * |
| NM_000492.3: c.2145_2146delAAinsGT | K716X | nonsense | ref | ref|ref | 0 pathogenic alleles | * |
| NM_000492.3: c.2997_3000delAATT | 3129del4 | nonsense | ref | ref|ref | 0 pathogenic alleles | * |
| NM_000492.3: c.1220_1239delAATTATTTGAGAAAGCAAAA | NP_000483.3: p. Glu407Alafs*4 | frameshift | ref | ref|ref | 0 pathogenic alleles | * |
| NM_000492.3: c.2589_2599delAATTTGGTGCT | 2721del11 | frameshift | ref | ref|ref | 0 pathogenic alleles | * |
| NM_000492.3: c.1610_1611delAC | 1742delAC | frameshift | ref | ref|ref | 0 pathogenic alleles | * |
| NM_000492.3: c.2324_2325delAC | 2456delAC | frameshift | ref | ref|ref | 0 pathogenic alleles | * |
| NM_000492.3: c.3041_3042delAC | 3173delAC | frameshift | ref | ref|ref | 0 pathogenic alleles | * |
| NM_000492.3: c.2859_2890delACATTCTGTTCTTCAAGCACCTATGTCAACCC | 2991del32 | frameshift | ref | ref|ref | 0 pathogenic alleles | * |
| NM_000492.3: c.3535_3538delACCA | 3667del4 | frameshift | ref | ref|ref | 0 pathogenic alleles | * |
| NM_000492.3: c.280_286delACCAAAG | 412del7->TA | frameshift | ref | ref|ref | 0 pathogenic alleles | * |
| NM_000492.3: c.1162_1168delACGACTA | 1294del7 | frameshift | ref | ref|ref | 0 pathogenic alleles | * |
| NM_000492.3: c.3400_3401delACinsGTA | 3532AC->GTA | frameshift | ref | ref|ref | 0 pathogenic alleles | * |
| NM_000492.3: c.1162_1163delACinsTA | T388X | nonsense | ref | ref|ref | 0 pathogenic alleles | * |
| NM_000492.3: c.1713_1714delAG | 1845delAG/1846delGA | frameshift | ref | ref|ref | 0 pathogenic alleles | * |
| NM_000492.3: c.3618_3619delAG | 3750delAG | frameshift | ref | ref|ref | 0 pathogenic alleles | * |
| NM_000492.3: c.720_741delAGGGAGAATGATGATGAAGTAC | 852del22 | frameshift | ref | ref|ref | 0 pathogenic alleles | * |
| NM_000492.3: c.111_112delAT | 241delAT | frameshift | ref | ref|ref | 0 pathogenic alleles | * |
| NM_000492.3: c.1330_1331delAT | 1460delAT | nonsense | ref | ref|ref | 0 pathogenic alleles | * |
| NM_000492.3: c.326_327delAT | 458delAT | nonsense | ref | ref|ref | 0 pathogenic alleles | * |
| NM_000492.3: c.805_806delAT | 936delTA | frameshift | ref | ref|ref | 0 pathogenic alleles | * |
| NM_000492.3: c.518_522delATAAA | 650delATAAA | frameshift | ref | ref|ref | 0 pathogenic alleles | * |
| NM_000492.3: c.3982_3984delATAinsTT | 4114ATA->TT | frameshift | ref | ref|ref | 0 pathogenic alleles | * |
| NM_000492.3: c.2816_2817delATinsC | 2948AT->C | frameshift | ref | ref|ref | 0 pathogenic alleles | * |
| NM_000492.3: c.2994_2997delATTA | 3126del4 | nonsense | ref | ref|ref | 0 pathogenic alleles | * |
| NM_000492.3: c.1029delC | 1161delC | nonsense | ref | ref|ref | 0 pathogenic alleles | * |
| NM_000492.3: c.1235delC | 1367delC | frameshift | ref | ref|ref | 0 pathogenic alleles | * |
| NM_000492.3: c.1670delC | 1802delC | frameshift | ref | ref|ref | 0 pathogenic alleles | * |

TABLE 3-continued

| | | | | | | |
|---|---|---|---|---|---|---|
| NM_000492.3: c.217delC | 347delC | frameshift | ref | ref|ref | 0 pathogenic alleles | * |
| NM_000492.3: c.2277delC | 2409delC | frameshift | ref | ref|ref | 0 pathogenic alleles | * |
| NM_000492.3: c.2615delC | 2747delC | frameshift | ref | ref|ref | 0 pathogenic alleles | * |
| NM_000492.3: c.3039delC | 3171delC | frameshift | ref | ref|ref | 0 pathogenic alleles | * |
| NM_000492.3: c.3264delC | 3396delC | frameshift | ref | ref|ref | 0 pathogenic alleles | * |
| NM_000492.3: c.3291delC | 3423delC | frameshift | ref | ref|ref | 0 pathogenic alleles | * |
| NM_000492.3: c.3528delC | 3659delC | frameshift | ref | ref|ref | 0 pathogenic alleles | * |
| NM_000492.3: c.357delC | 489delC | frameshift | ref | ref|ref | 0 pathogenic alleles | * |
| NM_000492.3: c.3659delC | 3791delC | frameshift | ref | ref|ref | 0 pathogenic alleles | * |
| NM_000492.3: c.4042delC | 4173delC | frameshift | ref | ref|ref | 0 pathogenic alleles | * |
| NM_000492.3: c.409delC | 541delC | frameshift | ref | ref|ref | 0 pathogenic alleles | * |
| NM_000492.3: c.4139delC | 4271delC | frameshift | ref | ref|ref | 0 pathogenic alleles | * |
| NM_000492.3: c.433delC | 565delC | frameshift | ref | ref|ref | 0 pathogenic alleles | * |
| NM_000492.3: c.43delC | 175delC | frameshift | ref | ref|ref | 0 pathogenic alleles | * |
| NM_000492.3: c.550delC | 681delC | frameshift | ref | ref|ref | 0 pathogenic alleles | * |
| NM_000492.3: c.927delC | 1058delC | frameshift | ref | ref|ref | 0 pathogenic alleles | * |
| NM_000492.3: c.1433_1434delCA | 1565delCA | nonsense | ref | ref|ref | 0 pathogenic alleles | * |
| NM_000492.3: c.1477_1478delCA | 1609delCA | frameshift | ref | ref|ref | 0 pathogenic alleles | * |
| NM_000492.3: c.1240_1244delCAAAA | 1367del5 | nonsense | ref | ref|ref | 0 pathogenic alleles | * |
| NM_000492.3: c.2276_2277delCC | 2406delCC | frameshift | ref | ref|ref | 0 pathogenic alleles | * |
| NM_000492.3: c.2240_2247delCGATACTG | 2372del8 | frameshift | ref | ref|ref | 0 pathogenic alleles | * |
| NM_000492.3: c.1093_1094delCT | 1221delCT | frameshift | ref | ref|ref | 0 pathogenic alleles | * |
| NM_000492.3: c.1642_1643delCT | 1774delCT | frameshift | ref | ref|ref | 0 pathogenic alleles | * |
| NM_000492.3: c.3229_3230delCT | 3359delCT | frameshift | ref | ref|ref | 0 pathogenic alleles | * |
| NM_000492.3: c.1984_1987delCTAA | 2116delCTAA | frameshift | ref | ref|ref | 0 pathogenic alleles | * |
| NM_000492.3: c.409_412delCTCC | 541del4 | frameshift | ref | ref|ref | 0 pathogenic alleles | * |
| NM_000492.3: c.1069delG | 1199delG | frameshift | ref | ref|ref | 0 pathogenic alleles | * |
| NM_000492.3: c.1083delG | 1215delG | frameshift | ref | ref|ref | 0 pathogenic alleles | * |
| NM_000492.3: c.1177delG | 1309delG | nonsense | ref | ref|ref | 0 pathogenic alleles | * |
| NM_000492.3: c.1234delG | 1366delG | frameshift | ref | ref|ref | 0 pathogenic alleles | * |
| NM_000492.3: c.1373delG | 1504delG | frameshift | ref | ref|ref | 0 pathogenic alleles | * |
| NM_000492.3: c.1418delG | 1548delG | frameshift | ref | ref|ref | 0 pathogenic alleles | * |
| NM_000492.3: c.1439delG | 1571delG | frameshift | ref | ref|ref | 0 pathogenic alleles | * |
| NM_000492.3: c.1528delG | 1660delG | frameshift | ref | ref|ref | 0 pathogenic alleles | * |
| NM_000492.3: c.1652delG | 1784delG | frameshift | ref | ref|ref | 0 pathogenic alleles | * |
| NM_000492.3: c.1738delG | 1870delG | frameshift | ref | ref|ref | 0 pathogenic alleles | * |
| NM_000492.3: c.1800delG | 1932delG | frameshift | ref | ref|ref | 0 pathogenic alleles | * |
| NM_000492.3: c.1911delG | 2043delG | frameshift | ref | ref|ref | 0 pathogenic alleles | * |
| NM_000492.3: c.2215delG | 2347delG | frameshift | ref | ref|ref | 0 pathogenic alleles | * |
| NM_000492.3: c.2291delG | 2423delG | frameshift | ref | ref|ref | 0 pathogenic alleles | * |
| NM_000492.3: c.2380delG | 2512delG | frameshift | ref | ref|ref | 0 pathogenic alleles | * |
| NM_000492.3: c.2602delG | 2734G->AT | nonsense | ref | ref|ref | 0 pathogenic alleles | * |
| NM_000492.3: c.2875delG | 3007delG | frameshift | ref | ref|ref | 0 pathogenic alleles | * |
| NM_000492.3: c.2909delG | 3041delG | frameshift | ref | ref|ref | 0 pathogenic alleles | * |
| NM_000492.3: c.3022delG | 3154delG | frameshift | ref | ref|ref | 0 pathogenic alleles | * |
| NM_000492.3: c.3294delG | 3425delG | frameshift | ref | ref|ref | 0 pathogenic alleles | * |
| NM_000492.3: c.3315delG | 3447delG | frameshift | ref | ref|ref | 0 pathogenic alleles | * |
| NM_000492.3: c.3592delG | 3724delG | nonsense | ref | ref|ref | 0 pathogenic alleles | * |
| NM_000492.3: c.3623delG | 3755delG | frameshift | ref | ref|ref | 0 pathogenic alleles | * |
| NM_000492.3: c.3747delG | 3878delG | frameshift | ref | ref|ref | 0 pathogenic alleles | * |
| NM_000492.3: c.601delG | 733delG | frameshift | ref | ref|ref | 0 pathogenic alleles | * |
| NM_000492.3: c.773delG | 905delG | frameshift | ref | ref|ref | 0 pathogenic alleles | * |
| NM_000492.3: c.328delG | 460delG | frameshift | ref | ref|ref | 0 pathogenic alleles | * |
| NM_000492.3: c.80delG | 211delG | frameshift | ref | ref|ref | 0 pathogenic alleles | * |
| NM_000492.3: c.2924_2925delGA | 3056delGA | frameshift | ref | ref|ref | 0 pathogenic alleles | * |
| NM_000492.3: c.3485_3486delGA | 3617delGA | frameshift | ref | ref|ref | 0 pathogenic alleles | * |
| NM_000492.3: c.3790_3799delGAAGGAGAAA | 3922del10->C | frameshift | ref | ref|ref | 0 pathogenic alleles | * |
| NM_000492.3: c.1786_1787delGC | 1918delGC | nonsense | ref | ref|ref | 0 pathogenic alleles | * |
| NM_000492.3: c.4040_4041delGC | 4172delGC | frameshift | ref | ref|ref | 0 pathogenic alleles | * |
| NM_000492.3: c.1871_1878delGCTATTTT | 2003del8 | frameshift | ref | ref|ref | 0 pathogenic alleles | * |
| NM_000492.3: c.319_326delGCTTCCTA | 451del8 | nonsense | ref | ref|ref | 0 pathogenic alleles | * |
| NM_000492.3: c.1365_1366delGG | 1497delGG | frameshift | ref | ref|ref | 0 pathogenic alleles | * |
| NM_000492.3: c.3139_3139 + 1delGG | 3271delGG | splice site deletion | ref | ref|ref | 0 pathogenic alleles | * |
| NM_000492.3: c.4242_4242 + 1delGinsTT | 4374_4374 + 1GG > TT | splice site deletion | ref | ref|ref | 0 pathogenic alleles | * |
| NM_000492.3: c.2634_2641delGGTTGTGC | 2766del8 | frameshift | ref | ref|ref | 0 pathogenic alleles | * |
| NM_000492.3: c.3816_3817delGT | 3944delGT | frameshift | ref | ref|ref | 0 pathogenic alleles | * |
| NM_000492.3: c.3199_3200delinsA | NP_000483.3: p. Ala1067Thrfs*16 | frameshift | ref | ref|ref | 0 pathogenic alleles | * |
| NM_000492.3: c.2157_2163delinsGT | 2289-2295 del7bpinsGT | nonsense | ref | ref|ref | 0 pathogenic alleles | * |
| NM_000492.3: c.1073_1079delinsTAAAAAAAT | Q359K/T360K; c. [1075C > A; 1079 C > A] | frameshift | ref | ref|ref | 0 pathogenic alleles | * |

TABLE 3-continued

| | | | | | | |
|---|---|---|---|---|---|---|
| NM_000492.3: c.775delinsTCTTCCTCAGATTCATTGTGATTACCTCA | NP_000483.3: p.Leu259Serfs*7 | frameshift | ref | ref\|ref | 0 pathogenic alleles | * |
| NM_000492.3: c.1703delT | 1833delT | frameshift | ref | ref\|ref | 0 pathogenic alleles | * |
| NM_000492.3: c.2012delT | 2143delT | nonsense | ref | ref\|ref | 0 pathogenic alleles | * |
| NM_000492.3: c.233delT | 360delT | frameshift | ref | ref\|ref | 0 pathogenic alleles | * |
| NM_000492.3: c.2453delT | 2585delT | frameshift | ref | ref\|ref | 0 pathogenic alleles | * |
| NM_000492.3: c.2472delT | 2603delT | frameshift | ref | ref\|ref | 0 pathogenic alleles | * |
| NM_000492.3: c.2502delT | 2634delT | frameshift | ref | ref\|ref | 0 pathogenic alleles | * |
| NM_000492.3: c.2508delT | 2640delT | frameshift | ref | ref\|ref | 0 pathogenic alleles | * |
| NM_000492.3: c.2562delT | 2694delT | frameshift | ref | ref\|ref | 0 pathogenic alleles | * |
| NM_000492.3: c.2583delT | 2711delT | frameshift | ref | ref\|ref | 0 pathogenic alleles | * |
| NM_000492.3: c.2777delT | 2909delT | frameshift | ref | ref\|ref | 0 pathogenic alleles | * |
| NM_000492.3: c.2825delT | 2957delT | frameshift | ref | ref\|ref | 0 pathogenic alleles | * |
| NM_000492.3: c.3021delT | 3152delT | frameshift | ref | ref\|ref | 0 pathogenic alleles | * |
| NM_000492.3: c.3287delT | 3419delT | frameshift | ref | ref\|ref | 0 pathogenic alleles | * |
| NM_000492.3: c.3445delT | 3577delT | frameshift | ref | ref\|ref | 0 pathogenic alleles | * |
| NM_000492.3: c.3497delT | 3629delT | frameshift | ref | ref\|ref | 0 pathogenic alleles | * |
| NM_000492.3: c.3691delT | 3821delT | frameshift | ref | ref\|ref | 0 pathogenic alleles | * |
| NM_000492.3: c.387delT | 519delT | frameshift | ref | ref\|ref | 0 pathogenic alleles | * |
| NM_000492.3: c.393delT | 525delT | frameshift | ref | ref\|ref | 0 pathogenic alleles | * |
| NM_000492.3: c.3976delT | 4108delT | frameshift | ref | ref\|ref | 0 pathogenic alleles | * |
| NM_000492.3: c.429delT | 557delT | frameshift | ref | ref\|ref | 0 pathogenic alleles | * |
| NM_000492.3: c.494delT | 624delT | nonsense | ref | ref\|ref | 0 pathogenic alleles | * |
| NM_000492.3: c.50delT | 182delT | frameshift | ref | ref\|ref | 0 pathogenic alleles | * |
| NM_000492.3: c.531delT | 663delT | frameshift | ref | ref\|ref | 0 pathogenic alleles | * |
| NM_000492.3: c.948delT | 1078delT | frameshift | ref | ref\|ref | 0 pathogenic alleles | * |
| NM_000492.3: c.980delT | 1112delT | frameshift | ref | ref\|ref | 0 pathogenic alleles | * |
| NM_000492.3: c.3021delT | 3153delT | frameshift | ref | ref\|ref | 0 pathogenic alleles | * |
| NM_000492.3: c.112_113delTA | 244delTA | frameshift | ref | ref\|ref | 0 pathogenic alleles | * |
| NM_000492.3: c.1545_1546delTA | 1677delTA | nonsense | ref | ref\|ref | 0 pathogenic alleles | * |
| NM_000492.3: c.174_177delTAGA | 306delTAGA | frameshift | ref | ref\|ref | 0 pathogenic alleles | * |
| NM_000492.3: c.4071_4073delTAGinsAA | 4203TAG->AA | frameshift | ref | ref\|ref | 0 pathogenic alleles | * |
| NM_000492.3: c.543_546delTAGT | 675del4 | frameshift | ref | ref\|ref | 0 pathogenic alleles | * |
| NM_000492.3: c.3068_3072delTAGTG | 3200_3204delTAGTG | frameshift | ref | ref\|ref | 0 pathogenic alleles | * |
| NM_000492.3: c.325_327delTATinsG | 457TAT->G | frameshift | ref | ref\|ref | 0 pathogenic alleles | * |
| NM_000492.3: c.3882_3885delTATT | 4010del4 | frameshift | ref | ref\|ref | 0 pathogenic alleles | * |
| NM_000492.3: c.1053_1054delTC | 1185delTC | frameshift | ref | ref\|ref | 0 pathogenic alleles | * |
| NM_000492.3: c.1469_1470delTC | 1601delTC | frameshift | ref | ref\|ref | 0 pathogenic alleles | * |
| NM_000492.3: c.4196_4197delTC | 4326delTC | nonsense | ref | ref\|ref | 0 pathogenic alleles | * |
| NM_000492.3: c.3002_3003delTG | 3132delTG | frameshift | ref | ref\|ref | 0 pathogenic alleles | * |
| NM_000492.3: c.4200_4201delTG | 4332delTG | nonsense | ref | ref\|ref | 0 pathogenic alleles | * |
| NM_000492.3: c.4127_4131delTGGAT | NP_000483.3: p.Leu1376Serfs*8 | frameshift | ref | ref\|ref | 0 pathogenic alleles | * |
| NM_000492.3: c.4077_4080delTGTTinsAA | 4209TGTT->AA | frameshift | ref | ref\|ref | 0 pathogenic alleles | * |
| NM_000492.3: c.1159_1160delTT | 1291delTT | frameshift | ref | ref\|ref | 0 pathogenic alleles | * |
| NM_000492.3: c.1482_1483delTT | 1612delTT | frameshift | ref | ref\|ref | 0 pathogenic alleles | * |
| NM_000492.3: c.1919_1920delTT | 2051delTT | nonsense | ref | ref\|ref | 0 pathogenic alleles | * |
| NM_000492.3: c.2591_2592delTT | 2723delTT | frameshift | ref | ref\|ref | 0 pathogenic alleles | * |
| NM_000492.3: c.262_263delTT | 394delTT | frameshift | ref | ref\|ref | 0 pathogenic alleles | * |
| NM_000492.3: c.2775_2776delTT | 2907delTT | frameshift | ref | ref\|ref | 0 pathogenic alleles | * |
| NM_000492.3: c.2947_2948delTT | 3079delTT | frameshift | ref | ref\|ref | 0 pathogenic alleles | * |
| NM_000492.3: c.3835_3836delTT | NP_000483.3: p.Leu1279Alafs*22 | frameshift | ref | ref\|ref | 0 pathogenic alleles | * |
| NM_000492.3: c.862_869 + 1delTTAAGACAG | 994del9 | splice site deletion | ref | ref\|ref | 0 pathogenic alleles | * |
| NM_000492.3: c.1301C > G | S434X | nonsense | C | C\|C | 0 pathogenic alleles | * |
| NM_000492.3: c.1393 − 2A > G | 1525 − 2A->G | consensus splice | A | A\|A | 0 pathogenic alleles | * |
| NM_000492.3: c.1585 − 2A > G | 1717 − 2A->G | consensus splice | A | A\|A | 0 pathogenic alleles | * |
| NM_000492.3: c.165 − 2A > G | 297 − 2A->G | consensus splice | A | A\|A | 0 pathogenic alleles | * |
| NM_000492.3: c.2195T > G | L732X | nonsense | T | T\|T | 0 pathogenic alleles | * |
| NM_000492.3: c.2327C > G | S776X | nonsense | C | C\|C | 0 pathogenic alleles | * |
| NM_000492.3: c.2491 − 2A > G | 2623 − 2A->G | consensus splice | A | A\|A | 0 pathogenic alleles | * |
| NM_000492.3: c.2556T > G | Y852X | nonsense | T | T\|T | 0 pathogenic alleles | * |
| NM_000492.3: c.2620 − 2A > G | 2752 − 2A->G | consensus splice | A | A\|A | 0 pathogenic alleles | * |
| NM_000492.3: c.2658 − 2A > G | 2790 − 2A->G | consensus splice | A | A\|A | 0 pathogenic alleles | * |
| NM_000492.3: c.2989 − 2A > G | 3121 − 2A->G | consensus splice | A | A\|A | 0 pathogenic alleles | * |
| NM_000492.3: c.3176T > G | L1059X | nonsense | T | T\|T | 0 pathogenic alleles | * |
| NM_000492.3: c.3368 − 2A > G | 3500 − 2A->G | consensus splice | A | A\|A | 0 pathogenic alleles | * |
| NM_000492.3: c.3469 − 2A > G | 3601 − 2A->G | consensus splice | A | A\|A | 0 pathogenic alleles | * |
| NM_000492.3: c.3546C > G | Y1182X | nonsense | C | C\|C | 0 pathogenic alleles | * |
| NM_000492.3: c.3587C > G | S1196X | nonsense | C | C\|C | 0 pathogenic alleles | * |
| NM_000492.3: c.3761T > G | L1254X | nonsense | T | T\|T | 0 pathogenic alleles | * |
| NM_000492.3: c.380T > G | L127X | nonsense | T | T\|T | 0 pathogenic alleles | * |
| NM_000492.3: c.4364C > G | S1455X | nonsense | C | C\|C | 0 pathogenic alleles | * |
| NM_000492.3: c.741C > G | Y247X | nonsense | C | C\|C | 0 pathogenic alleles | * |
| NM_000492.3: c.744 − 2A > G | | consensus splice | A | A\|A | 0 pathogenic alleles | * |
| NM_000492.3: c.870 − 2A > G | 1002 − 2A > G | consensus splice | A | A\|A | 0 pathogenic alleles | * |

TABLE 3-continued

| | | | | | | |
|---|---|---|---|---|---|---|
| NM_000492.3: c.912C > G | Y304X | nonsense | C | C\|C | 0 pathogenic alleles | * |
| NM_000492.3: c.1397C > G | S466X(TAG) | nonsense | C | C\|C | 0 pathogenic alleles | * |
| NM_000492.3: c.164 + 2T > G | 296 + 2T->G | consensus splice | T | T\|T | 0 pathogenic alleles | * |
| NM_000492.3: c.1A > G | M1V | initiator | A | A\|A | 0 pathogenic alleles | * |
| NM_000492.3: c.263T > G | L88X(T->G) | nonsense | T | T\|T | 0 pathogenic alleles | * |
| NM_000492.3: c.274 − 2A > G | 406 − 2A->G | consensus splice | A | A\|A | 0 pathogenic alleles | * |
| NM_000492.3: c.302T > G | L101X | nonsense | T | T\|T | 0 pathogenic alleles | * |
| NM_000492.3: c.3276C > G | Y1092X(C->G) | nonsense | C | C\|C | 0 pathogenic alleles | * |
| NM_000492.3: c.3617C > G | S1206X | nonsense | C | C\|C | 0 pathogenic alleles | * |
| NM_000492.3: c.489 + 2T > G | 621 + 2T->G | consensus splice | T | T\|T | 0 pathogenic alleles | * |
| NM_000492.3: c.490 − 2A > G | 622 − 2A->G | consensus splice | A | A\|A | 0 pathogenic alleles | * |
| NM_000492.3: c.105_106insA | 237insA | frameshift | ref | ref\|ref | 0 pathogenic alleles | * |
| NM_000492.3: c.1127_1128insA | 1259insA | frameshift | ref | ref\|ref | 0 pathogenic alleles | * |
| NM_000492.3: c.1191_1192insA | 1323insA | frameshift | ref | ref\|ref | 0 pathogenic alleles | * |
| NM_000492.3: c.174_175insA | 306insA | frameshift | ref | ref\|ref | 0 pathogenic alleles | * |
| NM_000492.3: c.2009_2010insA | 2141insA | frameshift | ref | ref\|ref | 0 pathogenic alleles | * |
| NM_000492.3: c.2052_2053insA | 2184insA | frameshift | ref | ref\|ref | 0 pathogenic alleles | * |
| NM_000492.3: c.2089_2090insA | 2221insA | frameshift | ref | ref\|ref | 0 pathogenic alleles | * |
| NM_000492.3: c.2175_2176insA | 2307insA | frameshift | ref | ref\|ref | 0 pathogenic alleles | * |
| NM_000492.3: c.2600_2601insA | 2732insA | frameshift | ref | ref\|ref | 0 pathogenic alleles | * |
| NM_000492.3: c.2968_2969insA | 3100insA | frameshift | ref | ref\|ref | 0 pathogenic alleles | * |
| NM_000492.3: c.303_304insA | 435insA | frameshift | ref | ref\|ref | 0 pathogenic alleles | * |
| NM_000492.3: c.3657_3658insA | 3789insA | frameshift | ref | ref\|ref | 0 pathogenic alleles | * |
| NM_000492.3: c.4039_4040insA | 4171insA | frameshift | ref | ref\|ref | 0 pathogenic alleles | * |
| NM_000492.3: c.4147_4148insA | 4279insA | frameshift | ref | ref\|ref | 0 pathogenic alleles | * |
| NM_000492.3: c.420_421insA | 552insA | frameshift | ref | ref\|ref | 0 pathogenic alleles | * |
| NM_000492.3: c.845_846insA | 977insA | frameshift | ref | ref\|ref | 0 pathogenic alleles | * |
| NM_000492.3: c.857_858insA | 989-992insA | frameshift | ref | ref\|ref | 0 pathogenic alleles | * |
| NC_000007.13: g.117180395_117180396ins6 | 1243ins6 | frameshift | ref | ref\|ref | 0 pathogenic alleles | * |
| NM_000492.3: c.2764_2765insAG | 2896insAG | frameshift | ref | ref\|ref | 0 pathogenic alleles | * |
| NM_000492.3: c.1329_1330insAGAT | 1461ins4 | frameshift | ref | ref\|ref | 0 pathogenic alleles | * |
| NM_000492.3: c.3957_3958insAGGG | 4089ins4 | frameshift | ref | ref\|ref | 0 pathogenic alleles | * |
| NM_000492.3: c.3424_3425insAGTA | 3556insAGTA | frameshift | ref | ref\|ref | 0 pathogenic alleles | * |
| NM_000492.3: c.1153_1154insAT | 1288insTA | frameshift | ref | ref\|ref | 0 pathogenic alleles | * |
| NM_000492.3: c.2424_2425insAT | 2556insAT | frameshift | ref | ref\|ref | 0 pathogenic alleles | * |
| NC_000007.13: g.117144416_117144417insATTGGAAA | 295ins8 | frameshift | ref | ref\|ref | 0 pathogenic alleles | * |
| NM_000492.3: c.1681_1682insC | 1813insC | frameshift | ref | ref\|ref | 0 pathogenic alleles | * |
| NM_000492.3: c.2044_2045insC | 2176insC | frameshift | ref | ref\|ref | 0 pathogenic alleles | * |
| NM_000492.3: c.2053_2054insC | 2185insC | frameshift | ref | ref\|ref | 0 pathogenic alleles | * |
| NM_000492.3: c.2390_2391insC | 2522insC | frameshift | ref | ref\|ref | 0 pathogenic alleles | * |
| NM_000492.3: c.3039_3040insC | 3171insC | frameshift | ref | ref\|ref | 0 pathogenic alleles | * |
| NM_000492.3: c.3766_3767insC | 3898insC | frameshift | ref | ref\|ref | 0 pathogenic alleles | * |
| NM_000492.3: c.3916_3917insCC | 4048insCC | frameshift | ref | ref\|ref | 0 pathogenic alleles | * |
| NM_000492.3: c.3188_3189insCTATG | 3320ins5 | frameshift | ref | ref\|ref | 0 pathogenic alleles | * |
| NM_000492.3: c.1029_1030insG | 1161insG | frameshift | ref | ref\|ref | 0 pathogenic alleles | * |
| NM_000492.3: c.2083_2084insG | 2215insG | frameshift | ref | ref\|ref | 0 pathogenic alleles | * |
| NM_000492.3: c.2737_2738insG | 2869insG | nonsense | ref | ref\|ref | 0 pathogenic alleles | * |
| NM_000492.3: c.3774_3775insG | 3906insG | frameshift | ref | ref\|ref | 0 pathogenic alleles | * |
| NM_000492.3: c.415_416insGA | 547insGA | frameshift | ref | ref\|ref | 0 pathogenic alleles | * |
| NM_000492.3: c.4296_4297insGA | 4428insGA | frameshift | ref | ref\|ref | 0 pathogenic alleles | * |
| NM_000492.3: c.1444_1445insT | 1576insT | nonsense | ref | ref\|ref | 0 pathogenic alleles | * |
| NM_000492.3: c.1739_1740insT | 1874insT | frameshift | ref | ref\|ref | 0 pathogenic alleles | * |
| NM_000492.3: c.227_228insT | 359insT | frameshift | ref | ref\|ref | 0 pathogenic alleles | * |
| NM_000492.3: c.228_229insT | 360-365insT | frameshift | ref | ref\|ref | 0 pathogenic alleles | * |
| NM_000492.3: c.233_234insT | 365-366 insT(W79fs) | frameshift | ref | ref\|ref | 0 pathogenic alleles | * |
| NM_000492.3: c.2434_2435insT | 2566insT | frameshift | ref | ref\|ref | 0 pathogenic alleles | * |
| NM_000492.3: c.247_248insT | 379-381insT | frameshift | ref | ref\|ref | 0 pathogenic alleles | * |
| NM_000492.3: c.2502_2503insT | 2634insT | nonsense | ref | ref\|ref | 0 pathogenic alleles | * |
| NM_000492.3: c.2810_2811insT | 2942insT | frameshift | ref | ref\|ref | 0 pathogenic alleles | * |
| NM_000492.3: c.3490_3491insT | 3622insT | nonsense | ref | ref\|ref | 0 pathogenic alleles | * |
| NM_000492.3: c.3773_3774insT | 3905insT | frameshift | ref | ref\|ref | 0 pathogenic alleles | * |
| NM_000492.3: c.3884_3885insT | 4016insT | frameshift | ref | ref\|ref | 0 pathogenic alleles | * |
| NM_000492.3: c.3890_3891insT | 4022insT | frameshift | ref | ref\|ref | 0 pathogenic alleles | * |
| NM_000492.3: c.4086_4087insT | 4218insT | nonsense | ref | ref\|ref | 0 pathogenic alleles | * |
| NM_000492.3: c.43_44insT | 175insT | frameshift | ref | ref\|ref | 0 pathogenic alleles | * |
| NM_000492.3: c.473_474insT | 605insT | frameshift | ref | ref\|ref | 0 pathogenic alleles | * |
| NM_000492.3: c.1157_1158insTA | 1289insTA | frameshift | ref | ref\|ref | 0 pathogenic alleles | * |
| NM_000492.3: c.1617_1618insTA | 1749insTA | nonsense | ref | ref\|ref | 0 pathogenic alleles | * |
| NM_000492.3: c.415_416insTA | 547insTA | frameshift | ref | ref\|ref | 0 pathogenic alleles | * |
| NM_000492.3: c.742_743insTACA | 874InsTACA | frameshift | ref | ref\|ref | 0 pathogenic alleles | * |
| NM_000492.3: c.1022_1023insTC | 1154insTC | frameshift | ref | ref\|ref | 0 pathogenic alleles | * |
| NM_000492.3: c.3535_3536insTCAA | 3667ins4 | frameshift | ref | ref\|ref | 0 pathogenic alleles | * |
| NM_000492.3: c.3664_3665insTCAA | NP_000483.3: p.Gly1222Valfs*44 | frameshift | ref | ref\|ref | 0 pathogenic alleles | * |
| NM_000492.3: c.2061_2062insTTTT | 2193ins4 | frameshift | ref | ref\|ref | 0 pathogenic alleles | * |
| NM_000492.3: c.1057C > T | Q353X | nonsense | C | C\|C | 0 pathogenic alleles | * |

TABLE 3-continued

| | | | | | | |
|---|---|---|---|---|---|---|
| NM_000492.3: c.115C > T | Q39X | nonsense | C | C\|C | 0 pathogenic alleles | * |
| NM_000492.3: c.1240C > T | Q414X | nonsense | C | C\|C | 0 pathogenic alleles | * |
| NM_000492.3: c.1435G > T | E479X | nonsense | G | G\|G | 0 pathogenic alleles | * |
| NM_000492.3: c.1456G > T | G486X | nonsense | G | G\|G | 0 pathogenic alleles | * |
| NM_000492.3: c.1477C > T | Q493X | nonsense | C | C\|C | 0 pathogenic alleles | * |
| NM_000492.3: c.1510G > T | E504X | nonsense | G | G\|G | 0 pathogenic alleles | * |
| NM_000492.3: c.1573C > T | Q525X | nonsense | C | C\|C | 0 pathogenic alleles | * |
| NM_000492.3: c.1606A > T | K536X | nonsense | A | A\|A | 0 pathogenic alleles | * |
| NM_000492.3: c.1624G > T | G542X | nonsense | G | G\|G | 0 pathogenic alleles | * |
| NM_000492.3: c.1726G > T | G576X | nonsense | G | G\|G | 0 pathogenic alleles | * |
| NM_000492.3: c.1753G > T | E585X | nonsense | G | G\|G | 0 pathogenic alleles | * |
| NM_000492.3: c.1792A > T | K598X | nonsense | A | A\|A | 0 pathogenic alleles | * |
| NM_000492.3: c.1900C > T | Q634X | nonsense | C | C\|C | 0 pathogenic alleles | * |
| NM_000492.3: c.1909C > T | Q637X | nonsense | C | C\|C | 0 pathogenic alleles | * |
| NM_000492.3: c.1966G > T | E656X | nonsense | G | G\|G | 0 pathogenic alleles | * |
| NM_000492.3: c.1990G > T | E664X | nonsense | G | G\|G | 0 pathogenic alleles | * |
| NM_000492.3: c.19G > T | E7X | nonsense | G | G\|G | 0 pathogenic alleles | * |
| NM_000492.3: c.2017G > T | G673X | nonsense | G | G\|G | 0 pathogenic alleles | * |
| NM_000492.3: c.2053C > T | Q685X | nonsense | C | C\|C | 0 pathogenic alleles | * |
| NM_000492.3: c.2062A > T | K688X | nonsense | A | A\|A | 0 pathogenic alleles | * |
| NM_000492.3: c.2065C > T | Q689X | nonsense | C | C\|C | 0 pathogenic alleles | * |
| NM_000492.3: c.2074G > T | E692X | nonsense | G | G\|G | 0 pathogenic alleles | * |
| NM_000492.3: c.2125C > T | R709X | nonsense | C | C\|C | 0 pathogenic alleles | * |
| NM_000492.3: c.2128A > T | K710X | nonsense | A | A\|A | 0 pathogenic alleles | * |
| NM_000492.3: c.2143C > T | Q715X | nonsense | C | C\|C | 0 pathogenic alleles | * |
| NM_000492.3: c.2158C > T | Q720X | nonsense | C | C\|C | 0 pathogenic alleles | * |
| NM_000492.3: c.2188G > T | E730X | nonsense | G | G\|G | 0 pathogenic alleles | * |
| NM_000492.3: c.2233G > T | G745X(Gly745X) | nonsense | G | G\|G | 0 pathogenic alleles | * |
| NM_000492.3: c.223C > T | R75X | nonsense | C | C\|C | 0 pathogenic alleles | * |
| NM_000492.3: c.2290C > T | R764X | nonsense | C | C\|C | 0 pathogenic alleles | * |
| NM_000492.3: c.2341C > T | Q781X | nonsense | C | C\|C | 0 pathogenic alleles | * |
| NM_000492.3: c.2353C > T | R785X | nonsense | C | C\|C | 0 pathogenic alleles | * |
| NM_000492.3: c.2440C > T | Q814X | nonsense | C | C\|C | 0 pathogenic alleles | * |
| NM_000492.3: c.2467G > T | E823X | nonsense | G | G\|G | 0 pathogenic alleles | * |
| NM_000492.3: c.2479G > T | E827X | nonsense | G | G\|G | 0 pathogenic alleles | * |
| NM_000492.3: c.2488A > T | K830X | nonsense | A | A\|A | 0 pathogenic alleles | * |
| NM_000492.3: c.2491G > T | E831X | nonsense | G | G\|G | 0 pathogenic alleles | * |
| NM_000492.3: c.2551C > T | R851X | nonsense | C | C\|C | 0 pathogenic alleles | * |
| NM_000492.3: c.2668C > T | Q890X | nonsense | C | C\|C | 0 pathogenic alleles | * |
| NM_000492.3: c.2836A > T | K946X | nonsense | A | A\|A | 0 pathogenic alleles | * |
| NM_000492.3: c.292C > T | Q98X | nonsense | C | C\|C | 0 pathogenic alleles | * |
| NM_000492.3: c.2932A > T | K978X | nonsense | A | A\|A | 0 pathogenic alleles | * |
| NM_000492.3: c.3007G > T | G1003X | nonsense | G | G\|G | 0 pathogenic alleles | * |
| NM_000492.3: c.307G > T | G103X | nonsense | G | G\|G | 0 pathogenic alleles | * |
| NM_000492.3: c.3103C > T | Q1035X | nonsense | C | C\|C | 0 pathogenic alleles | * |
| NM_000492.3: c.3124C > T | Q1042X | nonsense | C | C\|C | 0 pathogenic alleles | * |
| NM_000492.3: c.3211C > T | Q1071X | nonsense | C | C\|C | 0 pathogenic alleles | * |
| NM_000492.3: c.3304A > T | R1102X | nonsense | A | A\|A | 0 pathogenic alleles | * |
| NM_000492.3: c.3310G > T | E1104X | nonsense | G | G\|G | 0 pathogenic alleles | * |
| NM_000492.3: c.3382A > T | R1128X | nonsense | A | A\|A | 0 pathogenic alleles | * |
| NM_000492.3: c.340A > T | K114X | nonsense | A | A\|A | 0 pathogenic alleles | * |
| NM_000492.3: c.3430C > T | Q1144X | nonsense | C | C\|C | 0 pathogenic alleles | * |
| NM_000492.3: c.3472C > T | R1158X | nonsense | C | C\|C | 0 pathogenic alleles | * |
| NM_000492.3: c.3484C > T | R1162X | nonsense | C | C\|C | 0 pathogenic alleles | * |
| NM_000492.3: c.3529A > T | K1177X | nonsense | A | A\|A | 0 pathogenic alleles | * |
| NM_000492.3: c.3556C > T | Q1186X | nonsense | C | C\|C | 0 pathogenic alleles | * |
| NM_000492.3: c.3712C > T | Q1238X | nonsense | C | C\|C | 0 pathogenic alleles | * |
| NM_000492.3: c.3841C > T | Q1281X | nonsense | C | C\|C | 0 pathogenic alleles | * |
| NM_000492.3: c.3871C > T | Q1291X | nonsense | C | C\|C | 0 pathogenic alleles | * |
| NM_000492.3: c.3922G > T | E1308X | nonsense | G | G\|G | 0 pathogenic alleles | * |
| NM_000492.3: c.3925C > T | NP_000483.3: p. Gln1309* | nonsense | C | C\|C | 0 pathogenic alleles | * |
| NM_000492.3: c.40A > T | K14X | nonsense | A | A\|A | 0 pathogenic alleles | * |
| NM_000492.3: c.4111G > T | E1371X | nonsense | G | G\|G | 0 pathogenic alleles | * |
| NM_000492.3: c.4144C > T | Q1382X | nonsense | C | C\|C | 0 pathogenic alleles | * |
| NM_000492.3: c.4168C > T | Q1390X | nonsense | C | C\|C | 0 pathogenic alleles | * |
| NM_000492.3: c.4231C > T | Q1411X | nonsense | C | C\|C | 0 pathogenic alleles | * |
| NM_000492.3: c.4234C > T | Q1412X | nonsense | C | C\|C | 0 pathogenic alleles | * |
| NM_000492.3: c.4252G > T | E1418X | nonsense | G | G\|G | 0 pathogenic alleles | * |
| NM_000492.3: c.4417G > T | E1473X | nonsense | G | G\|G | 0 pathogenic alleles | * |
| NM_000492.3: c.4426C > T | Q1476X | nonsense | C | C\|C | 0 pathogenic alleles | * |
| NM_000492.3: c.489 + 1G > T | 621 + 1G->T | consensus splice | G | G\|G | 0 pathogenic alleles | * |
| NM_000492.3: c.4C > T | Q2X(togetherwith R3W) | nonsense | C | C\|C | 0 pathogenic alleles | * |
| NM_000492.3: c.53 + 1G > T | 185 + 1G->T | consensus splice | G | G\|G | 0 pathogenic alleles | * |
| NM_000492.3: c.579 + 1G > T | 711 + 1G->T | consensus splice | G | G\|G | 0 pathogenic alleles | * |
| NM_000492.3: c.580 − 1G > T | 712 − 1G->T | consensus splice | G | G\|G | 0 pathogenic alleles | * |
| NM_000492.3: c.619C > T | Q207X | nonsense | C | C\|C | 0 pathogenic alleles | * |
| NM_000492.3: c.658C > T | Q220X | nonsense | C | C\|C | 0 pathogenic alleles | * |
| NM_000492.3: c.868C > T | Q290X | nonsense | C | C\|C | 0 pathogenic alleles | * |

TABLE 3-continued

| | | | | | | |
|---|---|---|---|---|---|---|
| NM_000492.3: c.88C > T | Q30X | nonsense | C | C\|C | 0 pathogenic alleles | * |
| NM_000492.3: c.988G > T | G330X | nonsense | G | G\|G | 0 pathogenic alleles | * |
| NM_000492.3: c.1135G > T | E379X | nonsense | G | G\|G | 0 pathogenic alleles | * |
| NM_000492.3: c.1584 + 1G > T | 1716 + 1G->T | consensus splice | G | G\|G | 0 pathogenic alleles | * |
| NM_000492.3: c.164 + 1G > T | 296 + 1G->T | consensus splice | G | G\|G | 0 pathogenic alleles | * |
| NM_000492.3: c.1648G > T | G550X | nonsense | G | G\|G | 0 pathogenic alleles | * |
| NM_000492.3: c.1654C > T | Q552X | nonsense | C | C\|C | 0 pathogenic alleles | * |
| NM_000492.3: c.1657C > T | R553X | nonsense | C | C\|C | 0 pathogenic alleles | * |
| NM_000492.3: c.1766 + 1G > T | 1898 + 1G->T | consensus splice | G | G\|G | 0 pathogenic alleles | * |
| NM_000492.3: c.178G > T | E60X | nonsense | G | G\|G | 0 pathogenic alleles | * |
| NM_000492.3: c.2374C > T | R792X | nonsense | C | C\|C | 0 pathogenic alleles | * |
| NM_000492.3: c.2464G > T | E822X | nonsense | G | G\|G | 0 pathogenic alleles | * |
| NM_000492.3: c.2490 + 1G > T | 2622 + 1G->T | consensus splice | G | G\|G | 0 pathogenic alleles | * |
| NM_000492.3: c.2620 − 1G > T | 2752 − 1G->T | consensus splice | G | G\|G | 0 pathogenic alleles | * |
| NM_000492.3: c.2658 − 1G > T | 2790 − 1G->T | consensus splice | G | G\|G | 0 pathogenic alleles | * |
| NM_000492.3: c.274 − 1G > T | 406 − 1G->T | consensus splice | G | G\|G | 0 pathogenic alleles | * |
| NM_000492.3: c.274G > T | E92X | nonsense | G | G\|G | 0 pathogenic alleles | * |
| NM_000492.3: c.2989 − 2A > T | 3121 − 2A->T | consensus splice | A | A\|A | 0 pathogenic alleles | * |
| NM_000492.3: c.3139 + 1G > T | 3271 + 1G > T | consensus splice | G | G\|G | 0 pathogenic alleles | * |
| NM_000492.3: c.3937C > T | Q1313X | nonsense | C | C\|C | 0 pathogenic alleles | * |
| NM_000492.3: c.3963 + 1G > T | 4095 + 1G->T | consensus splice | G | G\|G | 0 pathogenic alleles | * |
| NM_000492.3: c.3G > T | M1I(ATT) | initiator | G | G\|G | 0 pathogenic alleles | * |
| NM_000492.3: c.4201G > T | E1401X | nonsense | G | G\|G | 0 pathogenic alleles | * |
| NM_000492.3: c.4242 + 1G > T | 4374 + 1G->T | consensus splice | G | G\|G | 0 pathogenic alleles | * |
| NM_000492.3: c.451C > T | Q151X | nonsense | C | C\|C | 0 pathogenic alleles | * |
| NM_000492.3: c.577G > T | E193X | nonsense | G | G\|G | 0 pathogenic alleles | * |
| NM_000492.3: c.79G > T | G27X | nonsense | G | G\|G | 0 pathogenic alleles | * |
| NM_000492.3: c.1068G > A | W356X | nonsense | G | G\|G | 0 pathogenic alleles | * |
| NM_000492.3: c.1040G > A | R347H | missense | G | G\|G | 0 pathogenic alleles | 11118444 |
| NM_000492.3: c.1055G > A | R352Q | missense | G | G\|G | 0 pathogenic alleles | 11927667 |
| NM_000492.3: c.1364C > A | A455E | missense | C | C\|C | 0 pathogenic alleles | 10764788 |
| NM_000492.3: c.1675G > A | A559T | missense | G | G\|G | 0 pathogenic alleles | 1712898 |
| NM_000492.3: c.1682G > A | A561E | missense | C | C\|C | 0 pathogenic alleles | 17098864 |
| NM_000492.3: c.1687T > A | Y563N | missense | T | T\|T | 0 pathogenic alleles | 10764788 |
| NM_000492.3: c.1714G > A | D572N | missense | G | G\|G | 0 pathogenic alleles | 1712898 |
| NM_000492.3: c.1721C > A | P574H | missense | C | C\|C | 0 pathogenic alleles | 10764788 |
| NM_000492.3: c.178G > A | E60K | missense | G | G\|G | 0 pathogenic alleles | 18306312 |
| NM_000492.3: c.1837G > A | A613T | missense | G | G\|G | 0 pathogenic alleles | 9736778 |
| NM_000492.3: c.1865G > A | G622D | missense | G | G\|G | 0 pathogenic alleles | 9736778 |
| NM_000492.3: c.2464G > A | E822K | missense | G | G\|G | 0 pathogenic alleles | 9736778 |
| NM_000492.3: c.2496C > A | NP_000483.3: p. Cys832* | nonsense | C | C\|C | 0 pathogenic alleles | 20607857 |
| NM_000492.3: c.254G > A | G85E | missense | G | G\|G | 0 pathogenic alleles | 18306312 |
| NM_000492.3: c.2657 + 5G > A | 2789 + 5G > A | non-consensus splice | G | G\|G | 0 pathogenic alleles | 9101293 |
| NM_000492.3: c.274G > A | E92K | missense | G | G\|G | 0 pathogenic alleles | 18306312 |
| NM_000492.3: c.3199G > A | A1067T | missense | G | G\|G | 0 pathogenic alleles | 11242048 |
| NM_000492.3: c.3302T > A | M1101K | missense | T | T\|T | 0 pathogenic alleles | 17949678 |
| NM_000492.3: c.3731G > A | G1244E | missense | G | G\|G | 0 pathogenic alleles | 11242048 |
| NM_000492.3: c.4201G > A | E1401K | missense | G | G\|G | 0 pathogenic alleles | 18769034 |
| NM_000492.3: c.532G > A | G178R | missense | G | G\|G | 0 pathogenic alleles | 11242048 |
| NM_000492.3: c.577G > A | E193K | missense | G | G\|G | 0 pathogenic alleles | 11242048 |
| NM_000492.3: c.890G > A | R297Q | missense | G | G\|G | 0 pathogenic alleles | 11242048 |
| NM_000492.3: c.941G > A | G314E | missense | G | G\|G | 0 pathogenic alleles | 17949678 |
| NM_000492.3: c.1652G > A | G551D | missense | G | G\|G | 0 pathogenic alleles | 1712898 |
| NM_000492.3: c.148T > C | S50P | missense | T | T\|T | 0 pathogenic alleles | 18306312 |
| NM_000492.3: c.1645A > C | S549R(A->C) | missense | A | A\|A | 0 pathogenic alleles | 1712898 |
| NM_000492.3: c.1853T > C | I618T | missense | T | T\|T | 0 pathogenic alleles | 9736778 |
| NM_000492.3: c.1856T > C | L619S | missense | T | T\|T | 0 pathogenic alleles | 9736778 |
| NM_000492.3: c.1859A > C | H620P | missense | A | A\|A | 0 pathogenic alleles | 9736778 |
| NM_000492.3: c.1898T > C | L633P | missense | T | T\|T | 0 pathogenic alleles | 9736778 |
| NM_000492.3: c.2991G > C | L997F | missense | G | G\|G | 0 pathogenic alleles | 17949679 |
| NM_000492.3: c.3278T > C | L1093P | missense | T | T\|T | 0 pathogenic alleles | 10649505 |
| NM_000492.3: c.3454G > C | D1152H | missense | G | G\|G | 0 pathogenic alleles | 9804160 |
| NM_000492.3: c.3763T > C | S1255P | missense | T | T\|T | 0 pathogenic alleles | 11242048 |
| NM_000492.3: c.673T > C | C225R | missense | T | T\|T | 0 pathogenic alleles | 9374552 |
| NM_000492.3: c.1040G > C | R347P | missense | G | G\|G | 0 pathogenic alleles | 7680769 |
| NM_000492.3: c.1679G > C | R560T | missense | G | G\|G | 0 pathogenic alleles | 17098864 |
| NM_000492.3: c.1882G > C | G628R(G->C) | missense | G | G\|G | 0 pathogenic alleles | 9736778 |
| NM_000492.3: c.2908G > C | G970R | missense | G | G\|G | 0 pathogenic alleles | 11242048 |
| NM_000492.3: c.3209G > C | R1070P | missense | G | G\|G | 0 pathogenic alleles | 18951463 |
| NM_000492.3: c.2989_3139del | NP_000483.3: p. Leu997Alafs*13 | frameshift | ref | ref\|ref | 0 pathogenic alleles | 20607857 |
| NM_000492.3: c.3067_3072delATAGTG | 3199del6 | inframe deletion | ref | ref\|ref | 0 pathogenic alleles | 15371907 |
| NM_000492.3: c.1519_1521delATC | [delta]I507 | inframe deletion | ref | ref\|ref | 0 pathogenic alleles | 1712898 |
| NM_000492.3: c.3418_3420delATG | [delta]M1140 | inframe deletion | ref | ref\|ref | 0 pathogenic alleles | 9804160 |
| NM_000492.3: c.1521_1523delCTT | [delta]F508 | inframe deletion | ref | ref\|ref | 0 pathogenic alleles | 1712898 |
| NM_000492.3: c.1012A > G | T338A | missense | A | A\|A | 0 pathogenic alleles | 11927667 |
| NM_000492.3: c.1647T > G | S549R(T->G) | missense | T | T\|T | 0 pathogenic alleles | 1712898 |

TABLE 3-continued

| Variant Name | Alias or Protein Change | Effect | Reference Allele | Patient Genotype | Findings | Reference (URL or PMID) |
|---|---|---|---|---|---|---|
| NM_000492.3: c.1841A > G | D614G | missense | A | A\|A | 0 pathogenic alleles | 9736778 |
| NM_000492.3: c.1860T > G | H620Q | missense | T | T\|T | 0 pathogenic alleles | 9736778 |
| NM_000492.3: c.2374C > G | R792G | missense | C | C\|C | 0 pathogenic alleles | 9736778 |
| NM_000492.3: c.2399C > G | A800G | missense | C | C\|C | 0 pathogenic alleles | 9736778 |
| NM_000492.3: c.266A > G | Y89C | missense | A | A\|A | 0 pathogenic alleles | 18306312 |
| NM_000492.3: c.3140 − 26A > G | 3272 − 26A->G | non-consensus splice | A | A\|A | 0 pathogenic alleles | 10425036 |
| NM_000492.3: c.3409A > G | M1137V | missense | A | A\|A | 0 pathogenic alleles | 9804160 |
| NM_000492.3: c.3415A > G | I1139V | missense | A | A\|A | 0 pathogenic alleles | 9804160 |
| NM_000492.3: c.3909C > G | N1303K | missense | C | C\|C | 0 pathogenic alleles | 1712898 |
| NM_000492.3: c.617T > G | L206W | missense | T | T\|T | 0 pathogenic alleles | 15776432 |
| NM_000492.3: c.3410T > G | M1137R | missense | T | T\|T | 0 pathogenic alleles | 9804160 |
| NM_000492.3: c.−226G > T | −94G->T | promoter | G | G\|G | 0 pathogenic alleles | 17678620 |
| NM_000492.3: c.1000C > T | R334W | missense | C | C\|C | 0 pathogenic alleles | 7680769 |
| NM_000492.3: c.1039C > T | R347C | missense | C | C\|C | 0 pathogenic alleles | 7694154 |
| NM_000492.3: c.1315C > T | P439S | missense | C | C\|C | 0 pathogenic alleles | 18769034 |
| NM_000492.3: c.14C > T | P5L | missense | C | C\|C | 0 pathogenic alleles | 18306312 |
| NM_000492.3: c.1801A > T | I601F | missense | A | A\|A | 0 pathogenic alleles | 9736778 |
| NM_000492.3: c.2845C > T | H949Y | missense | C | C\|C | 0 pathogenic alleles | 11242048 |
| NM_000492.3: c.296C > T | P99L | missense | C | C\|C | 0 pathogenic alleles | 8663008 |
| NM_000492.3: c.3717 + 12191C > T | 3849 + 10kbC->T | non-consensus splice | C | C\|C | 0 pathogenic alleles | 7521937 |
| NM_000492.3: c.613C > T | P205S | missense | C | C\|C | 0 pathogenic alleles | 15776432 |
| NM_000492.3: c.1040G > T | R347L | missense | G | G\|G | 0 pathogenic alleles | 7694154 |
| NM_000492.3: c.1438G > T | G480C | missense | G | G\|G | 0 pathogenic alleles | 7757078 |
| NM_000492.3: c.1646G > T | S549I | missense | G | G\|G | 0 pathogenic alleles | 1712898 |
| NM_000492.3: c.254G > T | G85V | missense | G | G\|G | 0 pathogenic alleles | 18306312 |
| NM_000492.3: c.3196C > T | R1066C | missense | C | C\|C | 0 pathogenic alleles | 9374552 |
| NM_000492.3: c.3293G > T | W1098L | missense | G | G\|G | 0 pathogenic alleles | 17949679 |
| NM_000492.3: c.3868C > T | P1290S | missense | C | C\|C | 0 pathogenic alleles | 18769034 |

\* URL and Access Date: www.genet.sickkids.on.ca/Home.html 20101209
Congenital bilateral absence of the vas deferens
Known Pathogenic Variants - Negative Results

| Variant Name | Alias or Protein Change | Effect | Reference Allele | Patient Genotype | Findings | Reference (URL or PMID) |
|---|---|---|---|---|---|---|
| NM_000492.3: c.1477C > T | Q493X | nonsense | C | C\|C | 0 pathogenic alleles | * |
| NM_000492.3: c.1606A > T | K536X | nonsense | A | A\|A | 0 pathogenic alleles | * |
| NM_000492.3: c.1624G > T | G542X | nonsense | G | G\|G | 0 pathogenic alleles | * |
| NM_000492.3: c.2128A > T | K710X | nonsense | A | A\|A | 0 pathogenic alleles | * |
| NM_000492.3: c.2290C > T | R764X | nonsense | C | C\|C | 0 pathogenic alleles | * |
| NM_000492.3: c.3211C > T | Q1071X | nonsense | C | C\|C | 0 pathogenic alleles | * |
| NM_000492.3: c.3484C > T | R1162X | nonsense | C | C\|C | 0 pathogenic alleles | * |
| NM_000492.3: c.4231C > T | Q1411X | nonsense | C | C\|C | 0 pathogenic alleles | * |
| NM_000492.3: c.4417G > T | E1473X | nonsense | G | G\|G | 0 pathogenic alleles | * |
| NM_000492.3: c.4426C > T | Q1476X | nonsense | C | C\|C | 0 pathogenic alleles | * |
| NM_000492.3: c.579 + 1G > T | 711 + 1G->T | consensus splice | G | G\|G | 0 pathogenic alleles | * |
| NM_000492.3: c.580 − 1G > T | 712 − 1G->T | consensus splice | G | G\|G | 0 pathogenic alleles | * |
| NM_000492.3: c.1657C > T | R553X | nonsense | C | C\|C | 0 pathogenic alleles | * |
| NM_000492.3: c.1315C > T | P439S | missense | C | C\|C | 0 pathogenic alleles | 18769034 |
| NM_000492.3: c.1801A > T | I601F | missense | A | A\|A | 0 pathogenic alleles | 9736778 |
| NM_000492.3: c.3208C > T | R1070W | missense | C | C\|C | 0 pathogenic alleles | 18951463 |
| NM_000492.3: c.613C > T | P205S | missense | C | C\|C | 0 pathogenic alleles | 15776432 |
| NM_000492.3: c.3196C > T | R1066C | missense | C | C\|C | 0 pathogenic alleles | 9374552 |
| NM_000492.3: c.3868C > T | P1290S | missense | C | C\|C | 0 pathogenic alleles | 18769034 |
| NM_000492.3: c.233_234insT | 365-366 insT(W79fs) | frameshift | ref | ref\|ref | 0 pathogenic alleles | * |
| NM_000492.3: c.2502_2503insT | 2634insT | nonsense | ref | ref\|ref | 0 pathogenic alleles | * |
| NM_000492.3: c.3890_3891insT | 4022insT | frameshift | ref | ref\|ref | 0 pathogenic alleles | * |
| NM_000492.3: c.2764_2765insAG | 2896insAG | frameshift | ref | ref\|ref | 0 pathogenic alleles | * |
| NM_000492.3: c.2089_2090insA | 2221insA | frameshift | ref | ref\|ref | 0 pathogenic alleles | * |
| NM_000492.3: c.4147_4148insA | 4279insA | frameshift | ref | ref\|ref | 0 pathogenic alleles | * |
| NM_000492.3: c.1680 − 2A > G | | consensus splice | A | A\|A | 0 pathogenic alleles | * |
| NM_000492.3: c.1A > G | M1V | initiator | A | A\|A | 0 pathogenic alleles | * |
| NM_000492.3: c.1012A > G | T338A | missense | A | A\|A | 0 pathogenic alleles | 11927667 |
| NM_000492.3: c.2374C > G | R792G | missense | C | C\|C | 0 pathogenic alleles | 9736778 |
| NM_000492.3: c.2399C > G | A800G | missense | C | C\|C | 0 pathogenic alleles | 9736778 |
| NM_000492.3: c.3140 − 26A > G | 3272 − 26A->G | non-consensus splice | A | A\|A | 0 pathogenic alleles | 10425036 |
| NM_000492.3: c.3461A > G | D1154G | missense | A | A\|A | 0 pathogenic alleles | 9804160 |
| NM_000492.3: c.3909C > G | N1303K | missense | C | C\|C | 0 pathogenic alleles | 1712898 |
| NM_000492.3: c.617T > G | L206W | missense | T | T\|T | 0 pathogenic alleles | 15776432 |
| NM_000492.3: c.4200_4201delTG | 4332delTG | nonsense | ref | ref\|ref | 0 pathogenic alleles | * |
| NM_000492.3: c.1545_1546delTA | 1677delTA | nonsense | ref | ref\|ref | 0 pathogenic alleles | * |
| NM_000492.3: c.233delT | 360delT | frameshift | ref | ref\|ref | 0 pathogenic alleles | * |
| NM_000492.3: c.3445delT | 3577delT | frameshift | ref | ref\|ref | 0 pathogenic alleles | * |

TABLE 3-continued

| | | | | | | |
|---|---|---|---|---|---|---|
| NM_000492.3: c.4242_4242 + 1delGinsTT | 4374_4374 + 1G G > TT | splice site deletion | ref | ref\|ref | 0 pathogenic alleles | * |
| NM_000492.3: c.1521_1523delCTT | [delta]F508 | inframe deletion | ref | ref\|ref | 0 pathogenic alleles | 1712898 |
| NM_000492.3: c.4042delC | 4173delC | frameshift | ref | ref\|ref | 0 pathogenic alleles | * |
| NM_000492.3: c.43delC | 175delC | frameshift | ref | ref\|ref | 0 pathogenic alleles | * |
| NM_000492.3: c.650_659delAGTTGTTACA | NP_000483.3 p.Glu217Glyfs*11 | frameshift | ref | ref\|ref | 0 pathogenic alleles | * |
| NM_000492.3: c.2051_2052delAAinsG | 2183AA->G | frameshift | ref | ref\|ref | 0 pathogenic alleles | 20607857 |
| NM_000492.3: c.3605delA | 3737delA | frameshift | ref | ref\|ref | 0 pathogenic alleles | * |
| NM_000492.3: c.42delA | 174delA | frameshift | ref | ref\|ref | 0 pathogenic alleles | * |
| NM_000492.3: c.2490 + 2T > C | 2622 + 2T > C | consensus splice | T | T\|T | 0 pathogenic alleles | * |
| NM_000492.3: c.148T > C | S50P | missense | T | T\|T | 0 pathogenic alleles | 18306312 |
| NM_000492.3: c.2936A > C | D979A | missense | A | A\|A | 0 pathogenic alleles | 11118444 |
| NM_000492.3: c.2991G > C | L997F | missense | G | G\|G | 0 pathogenic alleles | 17949679 |
| NM_000492.3: c.1116 + 1G > A | 1248 + 1G->A | consensus splice | G | G\|G | 0 pathogenic alleles | * |
| NM_000492.3: c.1466C > A | S489X | nonsense | C | C\|C | 0 pathogenic alleles | * |
| NM_000492.3: c.1585 − 1G > A | 1717 − 1G->A | consensus splice | G | G\|G | 0 pathogenic alleles | * |
| NM_000492.3: c.2988 + 1G > A | 3120 + 1G->A | consensus splice | G | G\|G | 0 pathogenic alleles | * |
| NM_000492.3: c.3276C > A | Y1092X(C->A) | nonsense | C | C\|C | 0 pathogenic alleles | * |
| NM_000492.3: c.366T > A | Y122X | nonsense | T | T\|T | 0 pathogenic alleles | * |
| NM_000492.3: c.3846G > A | W1282X | nonsense | G | G\|G | 0 pathogenic alleles | * |
| NM_000492.3: c.3G > A | M1I(ATA) | initiator | G | G\|G | 0 pathogenic alleles | * |
| NM_000492.3: c.647G > A | W216X | nonsense | G | G\|G | 0 pathogenic alleles | * |
| NC_000007.13: g.117119984G > A | −33G->A | promoter | G | G\|G | 0 pathogenic alleles | 20972246 |
| NM_000492.3: c.1040G > A | R347H | missense | G | G\|G | 0 pathogenic alleles | 11118444 |
| NM_000492.3: c.2657 + 5G > A | 2789 + 5G > A | non-consensus | G | G\|G | 0 pathogenic alleles | 9101293 |
| NM_000492.3: c.274G > A | E92K | missense | G | G\|G | 0 pathogenic alleles | 18306312 |
| NM_000492.3: c.3731G > A | G1244E | missense | G | G\|G | 0 pathogenic alleles | 11242048 |
| NM_000492.3: c.4201G > A | E1401K | missense | G | G\|G | 0 pathogenic alleles | 18769034 |
| NM_000492.3: c.695T > A | V232D | missense | T | T\|T | 0 pathogenic alleles | 17949679 |

* URL and Access Date: www.genet.sickkids.on.ca/Home.html 20101209

Appendix

Test Names:

Physicians can order a test by GeneName or ConditionName. However we will report on conditions. This is because a gene can be involved in one or more conditions and it is possible that we have not curated variants for the other condition.

Definitions:

Ethnicity

Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.

Pathogenic (Known)—ACMG Category 1

We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.

Pathogenic (Novel)—ACMG Category 2

Novel pathogenic mutations for qualitative reports are those that have not been described in an affected individual and result in a deleterious mutation (such as nonsense, truncation, disruption of consensus splice site, or disruption of the initiator codon).

Ref Allele

Refers to the allele present at that coordinate in GRCh37. In some cases the reference allele might be the risk allele.

Sequence

The consensus base call and coverage is provided for each base sequenced. In addition a variant file for the individual is produced which contains information about positions that differ from the reference genome.

Variant of Unknown Significance (VUS)—ACMG Categories 3-6

A variant of unknown significance may have been observed in affected individuals but does not meet the criteria of pathogenicity or may be a novel variant with unclear functional effect. We provide frequency information and computational prediction for the functional effect of these variants.

General Disclaimer:

DNA studies do not constitute a definitive test for the selected condition(s) in all individuals. It should be realized that there are many possible sources of diagnostic error. Genotyping errors can result from trace contamination of PCR reactions and from rare genetic variants that interfere with analysis. This test is used for clinical purposes. It should not be regarded as investigational or for research. The laboratory is regulated under CLIA of 1988.

EXAMPLE 2

Hereditary Non Polyposis Colon Cancer with Background Screen

In this example, a requisition is submitted for HNPCC. The requisition originates from any of a clinician, company, partner, or individual. The requisition is submitted electronically, on paper, via web service, from an EMR/PHR, or other means. The sample [blood, saliva, or cells, etc.] is de-identified and an encrypted ID is assigned. DNA from the sample associated with the requisition is purified and quality assessed for downstream processing. The sample is prepared for sequencing with respect to the regions of interest as defined by the Curation Database. All sequence relevant to any curated loci of interest and/or genes relevant for conditions of interest is targeted for downstream sequencing by a combination of targeting methodologies, in this case by targeted hybridization and 'pull down' of selected regions in addition to targeted amplification of selected regions. The sequencing is performed with one or more sequencing/analysis platforms and quality monitored for per base, per locus, coordinate, and condition quality statistics, ultimately enabling sensitivity, specificity and accuracy statistics to be resolved on a per base, locus, coordinate or condition basis. The Requisition Engine performs the secondary analysis on the regions of interest as indicated by the client in the sample requisition, in this case variants that are known, novel and variants of unknown significance in the EPCAM, MLH1, MSH2, MSH6 and PMS2 genes which allows reporting on HNPCC as determined by the Locus Database as well as a background screen with pre-determined client thresholds on all other conditions in the Locus Database. The client/patient ID informs the regions for the Analysis Engine to interpret and per-condition results are determined. The data for the results are made available to be delivered as [a PDF, API for integration into electronic records, fax, etc.] as per client's instruction. In this case, the client's preferences are to receive results for known pathogenic variants, as well as novel variants and variants of unknown significance. The data may be used by the client directly, or reformatted into a clinical report summarizing the key information for a patient.

TABLE 4

Requisition

CONFIDENTIAL
[UPC Code]

| PATIENT | | SPECIMEN | | PHYSICIAN |
|---|---|---|---|---|
| Name: | Patient 0 | Lab #: | LocDev000001 | Dr. Feelgood |
| DOB: | Sept. 30, 1973 | Specimen type: | DNA | 123 University Dr. |
| MRN: | JK69503 | Sample received: | 02/03/2012 | Room 301 |
| Gender: | Female | Report date: | 02/04/2012 | Los Angeles, CA 90025 |
| Race: | Asian | | | |

Order Details

| Ordered Condition | Reported Conditions | Genes | Qualitative Report (Select all that apply for each ordered condition) | Quantitative Report (Threshold for reporting summary findings) |
|---|---|---|---|---|
| ☒ Hereditary non-polyposis colorectal cancer | Hereditary non-polyposis colorectal cancer | EPCAM MLH1 MSH2 MSH6 PMS2 | ☒ Pathogenic variants (known) ☒ Pathogenic variants (novel) ☒ Variants of unknown significance ☐ Sequence data | Not applicable |
| ☒ Comprehensive-Screen | All conditions | Various | ☒ Pathogenic variants (known) ☐ Pathogenic variants (novel) ☐ Variants of unknown significance ☐ Sequence data | ☐ >95% populations percentile ☐ >70% absolute risk ☒ >40% residual lifetime risk ☐ >3X relative risk ☐ Odds Ratios >2.0 or <0.5 ☐ [x] [value] |

TABLE 5

Summary Results

Summary Results

AT RISK: 2 pathogenic variants
(Risk Model: Autosomal Dominant)

| | Hereditary non-polyposis colorectal cancer | | | | |
|---|---|---|---|---|---|
| Variant Name | Alias | Known (PMID) or Novel | Ref Allele | Patient Genotype | Findings |
| NM_000251.1: c.989T > C; NP_000242.1: p.Leu330Pro | MSH2_00278 | Known (18383312) | T | T\|C | 1 pathogenic allele |

TABLE 5-continued

| | | | | |
|---|---|---|---|---|
| NM_000251.1: c.60delG; NP_000242.1: p.Arg21Alafs*43 | Novel | G | G\|del | 1 pathogenic allele |
| Comprehensive-Screen | NOT AT RISK Negative for pathogenic variants Negative for >40% residual lifetime risk | | | |

TABLE 6

Detailed Findings

Detailed Findings
Assay Methodology

PCR amplicons were designed to all coding exons +2bp intron/exon boundary and any previously observed pathogenic locus. Amplicons were amplified in patient DNA using PCR and sequenced using the 454 Jr. Sequencer and copy number variants relative to the reference genome GRCh37 (alias HG19) were determined using GATK.

Assay Performance

Figure 12:
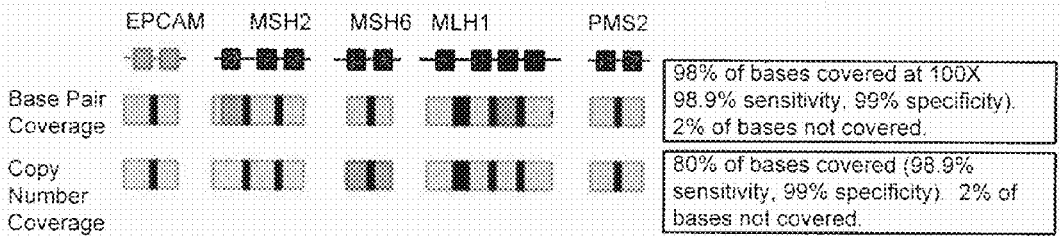
FIG. 12 is a diagram depicting assay performance with respect to genes EPCAM, MSHW, MSH6, MLH1 and PMS2 in Example 2.

FIG. 12 depicts the assay performance for EPCAM, MSH2, MSH6, MLH1 and PMS2 genes.

| | GCh37 Bases Covered (Green) | GRCh37 Bases Not Covered (Red) |
|---|---|---|
| Sequence Coverage | 2:400__440, 2:800__803, 2:810__900, 2:1000__1200 3:100__140, 3:160__210, 3:220__240 7:150__300, 7:325__500 | 2:804__809 3:210__220 |
| Copy Number Coverage | 2:400__440, 2:800__803, 2:810__900 3:100__140, 3:160__210, 3:220__240 7:150__300, 7:325__500 | 2:1000__1200 |

Sequence Results
Hereditary non-polyposis colorectal cancer
Known Pathogenic Variants - Positive or No Data

| Variant Name | Alias or Protein Change | Effect | Reference Allele | Patient Genotype | Findings | Reference (URL or PMID) |
|---|---|---|---|---|---|---|
| NM_000251.1: c.989T > C | MSH2_00278 | missense | T | T\|C | 1 pathogenic allele | 18383312 |
| NM_000179.2: c.2731C > T | MSH6_00071 | nonsense | C | NO DATA | Unknown | * |

* URL and Access Date: www.insight-group.org 20110321

Novel Pathogenic Variants

| Variant Name | Effect | Reference Allele | Patient Genotype | Findings |
|---|---|---|---|---|
| NM_000251.1: c.60delA | Truncation | A | A\|del | 1 pathogenic allele |

Variants of Unknown Significance

| Variant Name | Effect | Ref Allele | Patient Genotype | Number of Non-Reference Alleles | Observed in Affected Individuals (PMID) | Frequency of Patient Genotype in 1000 Genomes | Evolutionary Conservation Score | Splice Prediction Score |
|---|---|---|---|---|---|---|---|---|
| NM_000251.1: c.58A > G | Missense | A | G\|G | 2 | Unknown | 0.01% | Probably damaging | Detrimental |
| NM_000249.3: c.1625C > G | Silent | C | C\|G | 1 | Unknown | 10% | Benign | No effect |

Known Pathogenic Variants - Negative Results

| Variant Name | Alias or Protein Change | Effect | Reference Allele | Patient Genotype | Findings | Reference (URL or PMID) |
|---|---|---|---|---|---|---|
| NM_000179.2: c.2194C > T | MSH6_00067 | nonsense | C | C\|C | 0 pathogenic alleles | * |
| NM_000179.2: c.2719_2720delGT | MSH6_00180 | frameshift | ref | ref\|ref | 0 pathogenic alleles | * |
| NM_000179.2: c.3173 − 1__3173delGA | MSH6_00722 | consensus splice | ref | ref\|ref | 0 pathogenic alleles | * |
| NM_000179.2: c.3514_3515insA | MSH6_00220 | frameshift | ref | ref\|ref | 0 pathogenic alleles | * |
| NM_000249.3: c.104T > G | MLH1_00021 | missense | T | T\|T | 0 pathogenic alleles | 18383312 |
| NM_000249.3: c.1072delG | MLH1_00927 | frameshift | ref | ref\|ref | 0 pathogenic alleles | * |

TABLE 6-continued

| | | | | | | |
|---|---|---|---|---|---|---|
| NM_000249.3: c.1145_1146insA | MLH1_00928 | frameshift | ref | ref\|ref | 0 pathogenic alleles | * |
| NM_000249.3: c.1151T > A | NP_000240.1: p.Val384Asp | missense | T | T\|T | 0 pathogenic alleles | 18383312 |
| NM_000249.3: c.122A > G | MLH1_00067 | missense | A | A\|A | 0 pathogenic alleles | 18383312 |
| NM_000249.3: c.131C > T | MLH1_00071 | missense | C | C\|C | 0 pathogenic alleles | 18383312 |
| NM_000249.3: c.1489_1490insC | MLH1_00513 | frameshift | ref | ref\|ref | 0 pathogenic alleles | * |
| NM_000249.3: c.150_151insT | MLH1_00075 | frameshift | ref | ref\|ref | 0 pathogenic alleles | * |
| NM_000249.3: c.1517T > C | MLH1_00533 | missense | T | T\|T | 0 pathogenic alleles | 18383312 |
| NM_000249.3: c.161_164delGAGG | MLH1_01495 | frameshift | ref | ref\|ref | 0 pathogenic alleles | * |
| NM_000249.3: c.1625A > T | MLH1_00557 | missense | A | A\|A | 0 pathogenic alleles | 18383312 |
| NM_000249.3: c.1646T > C | MLH1_00569 | missense | T | T\|T | 0 pathogenic alleles | 18383312 |
| NM_000249.3: c.1652A > C | MLH1_00555 | missense | A | A\|A | 0 pathogenic alleles | 18383312 |
| NM_000249.3: c.1676T > G | MLH1_00595 | missense | T | T\|T | 0 pathogenic alleles | 18383312 |
| NM_000249.3: c.1721T > C | MLH1_00596 | missense | T | T\|T | 0 pathogenic alleles | 18383312 |
| NM_000249.3: c.1731G > A | MLH1_00601 | frameshift | G | G\|G | 0 pathogenic alleles | * |
| NM_000249.3: c.1733A > G | MLH1_00091 | missense | A | A\|A | 0 pathogenic alleles | 18383312 |
| NM_000249.3: c.1744C > T | MLH1_00635 | missense | C | C\|C | 0 pathogenic alleles | 18383312 |
| NM_000249.3: c.1756G > C | MLH1_00622 | missense | G | G\|G | 0 pathogenic alleles | 18383312 |
| NM_000249.3: c.18_34del17 | MLH1_00029 | frameshift | ref | ref\|ref | 0 pathogenic alleles | * |
| NM_000249.3: c.1853A > C | MLH1_00655 | missense | A | A\|A | 0 pathogenic alleles | 18383312 |
| NM_000249.3: c.1865T > A | MLH1_00643 | missense | T | T\|T | 0 pathogenic alleles | 18383312 |
| NM_000249.3: c.1893delT | MLH1_01478 | frameshift | ref | ref\|ref | 0 pathogenic alleles | * |
| NM_000249.3: c.191A > G | MLH1_00104 | missense | A | A\|A | 0 pathogenic alleles | 18383312 |
| NM_000249.3: c.194G > A | MLH1_00106 | missense | G | G\|G | 0 pathogenic alleles | 18383312 |
| NM_000249.3: c.1976G > T | MLH1_00685 | missense | G | G\|G | 0 pathogenic alleles | 18383312 |
| NM_000249.3: c.1989 + 1G > A | MLH1_00727 | consensus splice | G | G\|G | 0 pathogenic alleles | * |
| NM_000249.3: c.199G > T | MLH1_00109 | missense | G | G\|G | 0 pathogenic alleles | 18383312 |
| NM_000249.3: c.199G > A | MLH1_00108 | missense | G | G\|G | 0 pathogenic alleles | 18383312 |
| NM_000249.3: c.1990 − 1G > A | MLH1_00733 | consensus splice | G | G\|G | 0 pathogenic alleles | * |
| NM_000249.3: c.200G > A | MLH1_00110 | missense | G | G\|G | 0 pathogenic alleles | 18383312 |
| NM_000249.3: c.203T > A | MLH1_00112 | missense | T | T\|T | 0 pathogenic alleles | 18383312 |
| NM_000249.3: c.2067_2073del7 | MLH1_00748 | frameshift | ref | ref\|ref | 0 pathogenic alleles | * |
| NM_000249.3: c.2157_2158insT | NP_000240.1: p.Val720Cysfs*3 | frameshift | ref | ref\|ref | 0 pathogenic alleles | * |
| NM_000249.3: c.2210A > T | MLH1_00776 | missense | A | A\|A | 0 pathogenic alleles | 18383312 |
| NM_000249.3: c.2252_2253delAA | MLH1_00794 | frameshift | ref | ref\|ref | 0 pathogenic alleles | * |
| NM_000249.3: c.2265G > C | MLH1_00774 | missense | G | G\|G | 0 pathogenic alleles | 18383312 |
| NM_000249.3: c.230G > A | MLH1_00128 | missense | G | G\|G | 0 pathogenic alleles | 18383312 |
| NM_000249.3: c.238T > G | MLH1_00150 | missense | T | T\|T | 0 pathogenic alleles | 18383312 |
| NM_000249.3: c.250A > G | MLH1_00153 | missense | A | A\|A | 0 pathogenic alleles | 18383312 |
| NM_000249.3: c.304G > A | MLH1_00168 | missense | G | G\|G | 0 pathogenic alleles | 18383312 |
| NM_000249.3: c.320T > G | MLH1_00196 | missense | T | T\|T | 0 pathogenic alleles | 18383312 |
| NM_000249.3: c.332C > T | MLH1_00198 | missense | C | C\|C | 0 pathogenic alleles | 18383312 |
| NM_000249.3: c.350C > T | MLH1_00204 | missense | C | C\|C | 0 pathogenic alleles | 18383312 |
| NM_000249.3: c.350C > G | MLH1_00203 | missense | C | C\|C | 0 pathogenic alleles | 18383312 |
| NM_000249.3: c.382G > C | MLH1_00219 | missense | G | G\|G | 0 pathogenic alleles | 18383312 |
| NM_000249.3: c.394G > C | MLH1_00220 | missense | G | G\|G | 0 pathogenic alleles | 18383312 |
| NM_000249.3: c.544A > G | MLH1_00229 | missense | A | A\|A | 0 pathogenic alleles | 18383312 |
| NM_000249.3: c.546 − 1G > A | MLH1_00934 | consensus splice | G | G\|G | 0 pathogenic alleles | * |
| NM_000249.3: c.546 − 2A > G | MLH1_00256 | consensus splice | A | A\|A | 0 pathogenic alleles | * |
| NM_000249.3: c.554T > G | MLH1_00268 | missense | T | T\|T | 0 pathogenic alleles | 18383312 |
| NM_000249.3: c.577T > C | MLH1_00264 | missense | T | T\|T | 0 pathogenic alleles | 18383312 |
| NM_000249.3: c.676C > T | MLH1_00285 | nonsense | C | C\|C | 0 pathogenic alleles | * |
| NM_000249.3: c.677G > T | MLH1_00284 | missense | G | G\|G | 0 pathogenic alleles | 18383312 |
| NM_000249.3: c.677 + 3A > G | MLH1_00304 | non-consensus splice | A | A\|A | 0 pathogenic alleles | * |
| NM_000249.3: c.70delG | NP_000240.1: p.Val24Leufs*12 | missense | ref | ref\|ref | 0 pathogenic alleles | 18383312 |
| NM_000249.3: c.731G > A | MLH1_00324 | missense | G | G\|G | 0 pathogenic alleles | 18383312 |
| NM_000249.3: c.74T > C | MLH1_00050 | missense | T | T\|T | 0 pathogenic alleles | 18383312 |
| NM_000249.3: c.793C > T | MLH1_00363 | missense | C | C\|C | 0 pathogenic alleles | 18383312 |
| NM_000249.3: c.83C > T | MLH1_00053 | missense | C | C\|C | 0 pathogenic alleles | 18383312 |
| NM_000249.3: c.911A > T | MLH1_00406 | missense | A | A\|A | 0 pathogenic alleles | 18383312 |
| NM_000249.3: c.977T > C | MLH1_00433 | missense | T | T\|T | 0 pathogenic alleles | 18383312 |
| NM_000249.3: c.986A > C | MLH1_00417 | missense | A | A\|A | 0 pathogenic alleles | 18383312 |
| NM_000251.1: c.1007delC | MSH2_00834 | frameshift | ref | ref\|ref | 0 pathogenic alleles | * |
| NM_000251.1: c.1018_1019insA | MSH2_00835 | frameshift | ref | ref\|ref | 0 pathogenic alleles | * |
| NM_000251.1: c.1077 − 1G > C | MSH2_00300 | consensus splice | G | G\|G | 0 pathogenic alleles | * |
| NM_000251.1: c.1216C > T | MSH2_00312 | nonsense | C | C\|C | 0 pathogenic alleles | * |
| NM_000251.1: c.1226_1227delAG | MSH2_00323 | frameshift | ref | ref\|ref | 0 pathogenic alleles | * |
| NM_000251.1: c.1249_1253delGTTAT | MSH2_01354 | frameshift | ref | ref\|ref | 0 pathogenic alleles | * |
| NM_000251.1: c.1285C > T | MSH2_00366 | nonsense | C | C\|C | 0 pathogenic alleles | * |
| NM_000251.1: c.1373T > G | MSH2_00377 | nonsense | T | T\|T | 0 pathogenic alleles | * |
| NM_000251.1: c.1386 + 1G > A | MSH2_00390 | frameshift | G | G\|G | 0 pathogenic alleles | * |
| NM_000251.1: c.1511 − 2A > G | MSH2_00424 | consensus splice | A | A\|A | 0 pathogenic alleles | * |
| NM_000251.1: c.1654A > C | MSH2_00448 | missense | A | A\|A | 0 pathogenic alleles | 18383312 |
| NM_000251.1: c.166G > T | MSH2_01361 | nonsense | G | G\|G | 0 pathogenic alleles | * |
| NM_000251.1: c.1702_1703insA | MSH2_01355 | frameshift | ref | ref\|ref | 0 pathogenic alleles | * |
| NM_000251.1: c.1705_1706delGA | MSH2_00476 | frameshift | ref | ref\|ref | 0 pathogenic alleles | * |

TABLE 6-continued

| | | | | | | |
|---|---|---|---|---|---|---|
| NM_000251.1: c.187delG | MSH2_00061 | nonsense | ref | ref\|ref | 0 pathogenic alleles | * |
| NM_000251.1: c.1906G > C | MSH2_00508 | missense | G | G\|G | 0 pathogenic alleles | 18383312 |
| NM_000251.1: c.1924_1925delGT | MSH2_00473 | nonsense | ref | ref\|ref | 0 pathogenic alleles | * |
| NM_000251.1: c.2031_2032delAT | MSH2_01091 | frameshift | ref | ref\|ref | 0 pathogenic alleles | * |
| NM_000251.1: c.2038C > T | MSH2_00580 | nonsense | C | C\|C | 0 pathogenic alleles | * |
| NM_000251.1: c.2064G > A | MSH2_00606 | missense | G | G\|G | 0 pathogenic alleles | 18383312 |
| NM_000251.1: c.2245G > A | MSH2_00631 | missense | G | G\|G | 0 pathogenic alleles | 18383312 |
| NM_000251.1: c.226C > T | MSH2_00843 | nonsense | C | C\|C | 0 pathogenic alleles | * |
| NM_000251.1: c.2361_2362insT | MSH2_00832 | frameshift | ref | ref\|ref | 0 pathogenic alleles | * |
| NM_000251.1: c.2432T > G | MSH2_00643 | nonsense | T | T\|T | 0 pathogenic alleles | * |
| NM_000251.1: c.269_290AAGATCT TCTTCTGGTTCGTCA > AAGATCTT CTTCTGGTTCGTCAAAGATCTTC TTCTGGTTCGTCA | MSH2_00082 | nonsense | AAGATCT TCTTCTG GTTCGTCA | AAGATCTT CTTCTGG TTCGTCA\| AAGATCTT CTTCTGG TTCGTCA | 0 pathogenic alleles | * |
| NM_000251.1: c.277C > T | MSH2_00091 | missense | C | C\|C | 0 pathogenic alleles | 18383312 |
| NM_000251.1: c.488T > A | MSH2_00182 | missense | T | T\|T | 0 pathogenic alleles | 18383312 |
| NM_000251.1: c.490G > A | MSH2_00153 | missense | G | G\|G | 0 pathogenic alleles | 18383312 |
| NM_000251.1: c.508C > T | MSH2_00139 | nonsense | C | C\|C | 0 pathogenic alleles | * |
| NM_000251.1: c.560T > C | MSH2_00169 | missense | T | T\|T | 0 pathogenic alleles | 18383312 |
| NM_000251.1: c.638_639delTG | MSH2_00172 | frameshift | ref | ref\|ref | 0 pathogenic alleles | * |
| NM_000251.1: c.643C > T | MSH2_00143 | nonsense | C | C\|C | 0 pathogenic alleles | * |
| NM_000251.1: c.645 + 1G > A | MSH2_01251 | consensus splice | G | G\|G | 0 pathogenic alleles | * |
| NM_000251.1: c.696_697delTT | MSH2_00219 | frameshift | ref | ref\|ref | 0 pathogenic alleles | * |
| NM_000251.1: c.704_705delAA | MSH2_00210 | frameshift | ref | ref\|ref | 0 pathogenic alleles | * |
| NM_000251.1: c.711_714delTTAT | MSH2_00206 | frameshift | ref | ref\|ref | 0 pathogenic alleles | * |
| NM_000251.1: c.788_789delAT | MSH2_00193 | frameshift | ref | ref\|ref | 0 pathogenic alleles | * |
| NM_000251.1: c.943 − 2A > G | MSH2_00761 | consensus splice | A | A\|A | 0 pathogenic alleles | * |
| NM_000535.5: c.1261G > A | PMS2_00181 | nonsense | G | G\|G | 0 pathogenic alleles | * |
| 47609586-47618259 | | deletion | ref | ref\|ref | 0 pathogenic alleles | 19177550 |
| 47611609-47617666 | | deletion | ref | ref\|ref | 0 pathogenic alleles | 19177550 |
| 47609781-47624514 | | deletion | ref | ref\|ref | 0 pathogenic alleles | 19177550 |
| 47604618-47614972 | | deletion | ref | ref\|ref | 0 pathogenic alleles | 19177550 |
| 47612145-47614192 | | deletion | ref | ref\|ref | 0 pathogenic alleles | 21309036 |

This report was reviewed and approved by:
Rungood E-signature <Date>
Dr. Rungood, Laboratory Director
Appendix
Test Names:

Physicians can order a test by GeneName or ConditionName. However we will report on conditions. This is because a gene can be involved in one or more conditions and it is possible that we have not curated variants for the other condition.

Definitions:
Ethnicity

Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.

Pathogenic (Known)—ACMG Category 1

We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.

Pathogenic (Novel)—ACMG Category 2

Novel pathogenic mutations for qualitative reports are those that have not been described in an affected individual and result in a deleterious mutation (such as nonsense, truncation, disruption of consensus splice site, or disruption of the initiator codon).

Ref Allele

Refers to the allele present at that coordinate in GRCh37. In some cases the reference allele might be the risk allele.

Sequence

The consensus base call and coverage is provided for each base sequenced. In addition a variant file for the individual is produced which contains information about positions that differ from the reference genome.

Variant of Unknown Significance (VUS)—ACMG Categories 3-6

A variant of unknown significance may have been observed in affected individuals but does not meet the criteria of pathogenicity or may be a novel variant with unclear functional effect. We provide frequency information and computational prediction for the functional effect of these variants.

General Disclaimer:

DNA studies do not constitute a definitive test for the selected condition(s) in all individuals. It should be realized that there are many possible sources of diagnostic error. Genotyping errors can result from trace contamination of PCR reactions and from rare genetic variants that interfere with analysis. This test is used for clinical purposes. It should not be regarded as investigational or for research. The laboratory is regulated under CLIA of 1988.

EXAMPLE 3

Colorectal Cancer with Background Screen

In this example, a requisition is submitted for Colorectal Cancer and a background screen for other conditions with pre-determined client thresholds. The requisition originates from any of a clinician, company, partner, or individual. The requisition is submitted electronically, on paper, via web service, from an EMR/PHR, or other means. The sample [blood, saliva, or cells, etc.] is de-identified and an encrypted ID is assigned. DNA from the sample associated with the requisition is purified and quality assessed for downstream processing. The sample is prepared for sequencing with respect to the regions of interest as defined by the Curation Database. All sequence relevant to any curated loci of interest and/or genes relevant for conditions of interest is targeted for downstream sequencing by a combination of targeting methodologies, in this case by targeted hybridization and 'pull down' of selected regions in addition to targeted amplification of selected regions. The sequencing is performed with one or more sequencing/analysis platforms and quality monitored for per base, per locus, coordinate, and condition quality statistics, ultimately enabling sensitivity, specificity and accuracy statistics to be resolved on a per base, locus, coordinate or condition basis. The Requisition Engine performs the secondary analysis on the regions of interest as indicated by the client in the sample requisition, in this case variants that are known for Colorectal Cancer as well as analysis of all other conditions in the Locus Database that are pathogenic above a pre-determined client threshold. The client/patient ID informs the regions for the Analysis Engine to interpret and per-condition results are determined. The data for the results are made available to be delivered as [a PDF, API for integration into electronic records, fax, etc.] as per client's instruction. In this case, the client's preferences are to receive results for known pathogenic variants, as well as the results of the threshold screen of all other conditions in the Locus Database. The data may be used by the client directly, or reformatted into a clinical report summarizing the key information for a patient.

TABLE 7

Requisition

CONFIDENTIAL
[UPC Code]

| PATIENT | | SPECIMEN | | PHYSICIAN |
|---|---|---|---|---|
| Name: | Patient 0 | Lab #: | LocDev000001 | Dr. Feelgood |
| DOB: | Sept. 30, 1973 | Specimen type: | DNA | 123 University Dr. |
| MRN: | JK69503 | Sample received: | 02/03/2012 | Room 301 |
| Gender: | Female | Report date: | 02/04/2012 | Los Angeles, CA 90025 |
| Race: | Asian AND White | | | |

Order Details

| Ordered Condition | Reported Conditions | Genes | Qualitative Report (Select all that apply for each ordered condition) | Quantitative Report (Threshold for reporting summary findings) |
|---|---|---|---|---|
| ☒ Colorectal cancer, sporadic | Colorectal cancer, sporadic | Various | Not applicable | ☐ >95% populations percentile<br>☐ >70% absolute risk<br>☒ >40% residual lifetime risk<br>☐ >3X relative risk<br>☐ Odds Ratios >2.0 or <0.5<br>☐ [x] [value] |
| ☒ Comprehensive-Screen | All conditions | Various | ☒ Pathogenic variants (known)<br>☐ Pathogenic variants (novel)<br>☐ Variants of unknown significance<br>☐ Sequence data | ☐ >95% populations percentile<br>☐ >70% absolute risk<br>☒ >40% residual lifetime risk<br>☐ >3X relative risk<br>☐ Odds Ratios >2.0 or <0.5<br>☐ [x] [value] |

TABLE 8

Summary Results

Summary Results

| Colorectal cancer, sporadic | | | | AT RISK: 43% Residual Lifetime Risk | |
|---|---|---|---|---|---|
| | | Known | | (Risk Model: Quantitative, Ancestry Asian) | |
| Variant Name | Alias | (PMID) or Novel | Ref Allele | Patient Genotype | Findings |
| Chr8: 128413304_128413304T > G | rs6983267 | Known (21242260) | T | T\|G | 1 risk allele (OR = 1.18, (x, y)) |
| Chr18: 46453462_46453462C > T | rs4939827 | Known (21242260) | C | T\|T | 2 risk alleles (OR = 1.25, (x, y)) |
| Chr10: 8701218_8701218G > A | rs10795668 | Known (21242260) | G | G\|G | 0 risk alleles (OR = 1.00) |

| Colorectal cancer, sporadic | | | | NOT AT RISK: 23% Residual Lifetime Risk | |
|---|---|---|---|---|---|
| | | Known | | (Risk Model: Quantitative, Ancestry: White) | |
| Variant Name | Alias | (PMID) or Novel | Ref Allele | Patient Genotype | Findings |
| Chr8: 128424791_128424791G > A | rs7014346 | Known (18372901) | G | A\|G | 1 risk allele (OR = 1.19, (x, y)) |
| Chr18: 46453462_46453462C > T | rs4939827 | Known (18372901) | C | T\|T | 2 risk alleles (OR = 1.20, (x, y)) |
| Chr8: 117630682_117630682A > C | rs16892766 | Known (18372905) | A | A\|A | 0 risk alleles (OR = 1.00) |
| Chr10: 8701218_8701218G > A | rs10795668 | Known (18372905) | G | G\|G | 0 risk alleles (OR = 1.00) |
| Chr11: 111171708_111171708A > C | rs3802842 | Known (18372901) | A | A\|A | 0 risk alleles (OR = 1.00) |
| Chr15: 32994755_32994755C > T | rs4779584 | Known (18084292) | C | C\|C | 0 risk alleles (OR = 1.00) |

| Comprehensive-Screen | NOT AT RISK |
|---|---|
| | Negative for pathogenic variants |
| | Negative for >40% residual lifetime risk |

TABLE 9

Detailed Findings

Detailed Findings
Assay Methodology

PCR amplicons were designed to all coding exons +2bp intron/exon boundary and any previously observed pathogenic locus. Amplicons were amplified in patient DNA using PCR and sequenced using the 454 Jr. Sequencer and copy number variants relative to the reference genome GRCh37 (alias HG19) were determined using GATK.

Assay Performance

| Chromosomal Location | |
|---|---|
| Chr8: 128413304_128413304<br>Chr8: 128424791_128424791<br>Chr8: 117630682_117630682<br>Chr10: 8701218_8701218<br>Chr11: 111171708_111171708<br>Chr15: 32994755_32994755<br>Chr18: 46453462_46453462 | 100% of bases covered at 100X (98.9% sensitivity, 99% specificity). 0% of bases not covered. |

Sequence Results
Colorectal cancer, sporadic
Known Variants, Ancestry: Asian

| Variant Name | Alias or Protein Change | Frequency of Patient Genotype in Population | Reference Allele | Patient Genotype | Findings | Reference (URL or PMID) |
|---|---|---|---|---|---|---|
| Chr8: 128413304_128413304T > G | rs6983267 | 2% | T | T\|G | 1 risk allele (OR = 1.18, (x, y)) | 21242260 |

TABLE 9-continued

Figure 14:
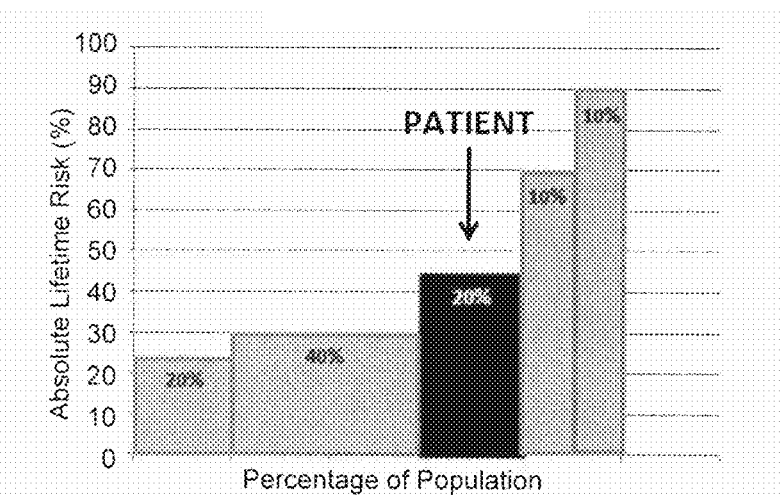
FIG. 14 is a chart of Percentage Absolute. Lifetime Risk against Percentage of Population depicting the Distribution of risk in Asian HapMap population relevant to colorectal cancer.

| Chr18: 46453462_46453462C > T | rs4939827 | 1% | C | T\|T | 2 risk alleles (OR = 1.25, (x, y)) | 21242260 |
| Chr10: 8701218:_8701218G > A | rs10795668 | 70% | G | G\|G | 0 risk alleles (OR = 1.00) | 21242260 |
| Distribution of risk in Asian HapMap population: | | | See FIG. 14 | | Residual lifetime risk: 43% Lifetime risk: 66% [pop avg = 10.2%] Relative risk = 6.4X Pop percentile = 95% | SEER* |

*SEER: http://seer.cancer.gov/csr/1975_2007/

Colorectal cancer, sporadic
Known Variants, Ancestry: White

Figure 15:
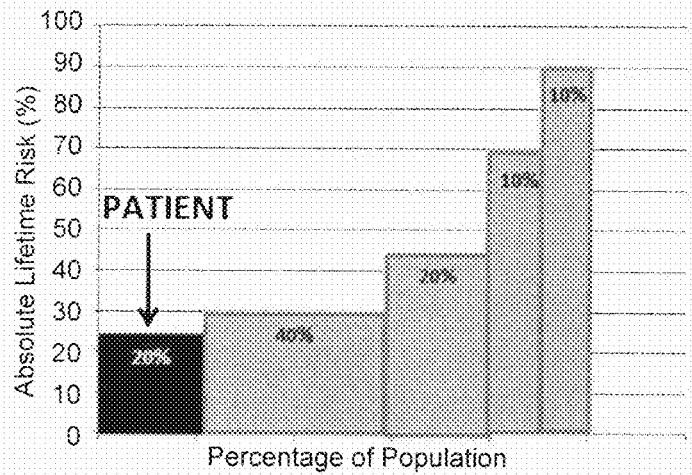
FIG. 15 is a chart of Percentage Absolute Lifetime Risk against Percentage of Population depicting the Distribution of risk in White HapMap population relevant to colorectal cancer.

| Variant Name | Alias or Protein Change | Frequency of Patient Genotype in Population | Reference Allele | Patient Genotype | Findings | Reference (URL or PMID) |
|---|---|---|---|---|---|---|
| Chr8: 128424791_128424791G > A | rs7014346 | 2% | G | A\|G | 1 risk allele (OR = 1.19, (x, y)) | rs7014346 |
| Chr18: 46453462_46453462C > T | rs4939827 | 1% | C | T\|T | 2 risk alleles (OR = 1.20, (x, y)) | rs4939827 |
| Chr8: 117630682_117630682A > C | rs16892766 | 70% | A | A\|A | 0 risk alleles (OR = 1.00) | rs16892766 |
| Chr10: 8701218_8701218G > A | rs10795668 | 65% | G | G\|G | 0 risk alleles (OR = 1.00) | rs10795668 |
| Chr11: 111171708_111171708A > C | rs3802842 | 60% | A | A\|A | 0 risk alleles (OR = 1.00) | rs3802842 |
| Chr15: 32994755_32994755C > T | rs4779584 | 55% | C | C\|C | 0 risk alleles (OR = 1.00) | rs4779584 |
| Distribution of risk in White HapMap population: | | | See FIG. 15 | | Residual lifetime risk: 23% Lifetime risk: 40% [pop avg = 8%] Relative risk = 5X Pop percentile = 90% | SEER* |

*SEER: http://seer.cancer.gov/csr/1975_2007/

This report was reviewed and approved by:
Rungood E-signature <Date>
Dr. Rungood, Laboratory Director
Appendix
Test Names:
Physicians can order a test by GeneName or ConditionName. However we will report on conditions. This is because a gene can be involved in one or more conditions and it is possible that we have not curated variants for the other condition.
Definitions:
Ethnicity
Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.
Pathogenic (Known)—ACMG Category 1
We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.
Pathogenic (Novel)—ACMG Category 2
Novel pathogenic mutations for qualitative reports are those that have not been described in an affected individual and result in a deleterious mutation (such as nonsense, truncation, disruption of consensus splice site, or disruption of the initiator codon).
Ref Allele
Refers to the allele present at that coordinate in GRCh37. In some cases the reference allele might be the risk allele.
Sequence
The consensus base call and coverage is provided for each base sequenced. In addition a variant file for the individual is produced which contains information about positions that differ from the reference genome.
Variant of Unknown Significance (VUS)—ACMG Categories 3-6
A variant of unknown significance may have been observed in affected individuals but does not meet the criteria of pathogenicity or may be a novel variant with unclear functional effect. We provide frequency information and computational prediction for the functional effect of these variants.
General Disclaimer:
DNA studies do not constitute a definitive test for the selected condition(s) in all individuals. It should be realized that there are many possible sources of diagnostic error.

Genotyping errors can result from trace contamination of PCR reactions and from rare genetic variants that interfere with analysis. This test is used for clinical purposes. It should not be regarded as investigational or for research. The laboratory is regulated under CLIA of 1988.

EXAMPLE 4

Fragile X with Background Screen Starting with Client-generated Sequence

In this example, a requisition is submitted for Fragile-X and background screen with pre-determined client thresholds defined by any of a clinician, company, partner, or individual. The requisition is submitted electronically, on paper, via web service, from an EMR/PHR, or other means including the sequence to be analyzed by Locus Development. Per base, per locus, coordinate, and condition quality statistics for the requisitioned sequence are determined by the Locus Analysis ultimately enabling sensitivity, specificity and accuracy statistics to be resolved on a per base, locus, coordinate or condition basis. The Requisition Engine performs the secondary analysis on the regions of interest as indicated by the client in the sample requisition, in this case variants that are known in the FMR1 which allows reporting on Fragile X, Fragile X expansion, Fragile X associate tremor and ataxia and FMR-1 related primary ovarian insufficiency as well as a background threshold screen for the other conditions in the Locus Database. The client/patient ID informs the regions for the Analysis Engine to interpret and per-condition results are determined. The data for the results are made available to be delivered as [a PDF, API for integration into electronic records, fax, etc.] as per client's instruction. In this case, the client's preferences are to receive results for known pathogenic variants, as well as novel variants and variants of unknown significance. The data may be used by the client directly, or reformatted into a clinical report summarizing the key information for a patient.

TABLE 10

| Requisition | | | | |
|---|---|---|---|---|
| | | | | CONFIDENTIAL [UPC Code] |
| PATIENT | | SPECIMEN | | PHYSICIAN |
| Name: | Patient 0 | Lab #: | LocDev000001 | Dr. Feelgood |
| DOB: | Sept. 30, 1973 | Specimen type: | DNA | 123 University Dr. |
| MRN: | JK69503 | Sample received: | 02/03/2012 | Room 301 |
| Gender: | Female | Report date: | 02/04/2012 | Los Angeles, CA 90025 |
| Race: | Asian | | | |

| Order Details | | | | |
|---|---|---|---|---|
| Ordered Condition | Reported Conditions | Genes | Qualitative Report (Select all that apply for each ordered condition) | Quantitative Report (Threshold for reporting summary findings) |
| ☒ Fragile X syndrome | Fragile X syndrome expansion Fragile X syndrome Fragile X-associated tremor and ataxia syndrome FMR1-related primary ovarian insufficiency | FMR1 | ☒ Pathogenic variants (known) ☐ Pathogenic variants (novel) ☐ Variants of unknown significance ☐ Sequence data | Not applicable |
| ☒ Comprehensive-Screen | All conditions | Various | ☒ Pathogenic variants (known) ☐ Pathogenic variants (novel) ☐ Variants of unknown significance ☐ Sequence data | ☐ >95% populations percentile ☐ >70% absolute risk ☒ >40% residual lifetime risk ☐ >3X relative risk ☐ Odds Ratios >2.0 or <0.5 ☐ [x] [value] |

TABLE 11

Summary Findings

Summary Results

| Fragile X syndrome expansion | | AT RISK: 1 mutable variant | | |
|---|---|---|---|---|
| | Known (PMID) or Novel | (Risk Model: X-linked, Recessive) | | |
| Variant Name | | Ref Allele | Patient Genotype | Findings |
| NM_002024.5: r.101_103CGG (5_3000) | Known (20301558) | (5_44) | 58|10 | 1 mutable allele |

| Fragile X syndrome | | | | |
|---|---|---|---|---|
| | Known (PMID) or Novel | NOT AT RISK: 0 pathogenic variant | | |
| Variant Name | | Ref Allele | Patient Genotype | Findings |
| NM_002024.5: r.101_103CGG (5_3000) | Known (20301558) | (5_44) | 58|10 | 0 pathogenic alleles |

| FMR1-related primary ovarian insufficiency | | AT RISK: 1 pathogenic variant | | |
|---|---|---|---|---|
| | Known (PMID) or Novel | (Risk Model: X-linked, Recessive) | | |
| Variant Name | | Ref Allele | Patient Genotype | Findings |
| NM_002024.5: r.101_103CGG (5_3000) | Known (20301558) | (5_44) | 58|10 | 1 pathogenic allele |

| Fragile X-associated tremor and ataxia syndrome | | AT RISK: 1 pathogenic variant | | |
|---|---|---|---|---|
| | Known (PMID) or Novel | (Risk Model: X-linked, Recessive) | | |
| Variant Name | | Ref Allele | Patient Genotype | BFindings |
| NM_002024.5: r.101_103CGG (5_3000) | Known (20301558) | (5_44) | 58|10 | 1 pathogenic allele |

| Comprehensive-Screen | NOT AT RISK<br>Negative for Pathogenic Variants<br>Negative for >40% residual lifetime risk |
|---|---|

TABLE 12

Detailed Findings

Detailed Findings
Assay Methodology

PCR amplicons were designed to all coding exons +2bp intron/exon boundary and any previously observed pathogenic locus. Amplicons were amplified in patient DNA using PCR and sequenced using the 454 Jr. Sequencer and copy number variants relative to the reference genome GRCh37 (alias HG19) were determined using GATK.

Assay Performance

Figure 13:
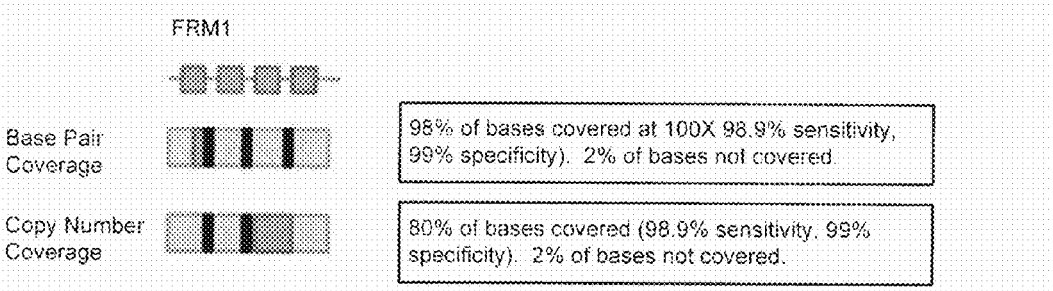
FIG. 13 is a diagram depicting assay performance with respect to genes FRM1 in Example 4.

FIG. 13 depicts the assay performance for FMR1 genes.

| | GRCh37 Bases Covered (Green) | GRCh37 Bases Not Covered (Red) |
|---|---|---|
| Sequence Coverage | X:400_440, X:800_803, X:810_900, X:1000_1200, X:1400-1800 | X:804_809 |
| Copy Number Coverage | X:400_440, X:800_803, X:810_900, X:1400-1800 | X:1000_1200 |

Sequence Results
Fragile X syndrome expansion
Known Pathogenic Variants

| Variant Name | Effect | Reference Allele | Patient Genotype | Finding | Reference (URL or PMID) |
|---|---|---|---|---|---|
| NM_002024.5: r.101_103CGG(5_3000) | UTR | (5_44) | 58|10 | 1 mutable allele, 1 not pathogenic allele | 20301558 |

TABLE 12-continued

Detailed Findings

| FMR1 Allele bins | 5_34 | | not pathogenic | 20301558 |
|---|---|---|---|---|
| | 35_44 | | not pathogenic | 20301558 |
| | 45_54 | | unknown | 20301558 |
| | 55_200 | | mutable | 20301558 |
| | >200 | | mutable | 20301558 |

Fragile X syndrome
Known Pathogenic Variants

| Variant Name | Effect | Reference Allele | Patient Genotype | Finding | Reference (URL or PMID) |
|---|---|---|---|---|---|
| NM_002024.5: r.101_103CGG(5_3000) | UTR | (5_44) | 58\|10 | 0 pathogenic alleles | 20301558 |
| FMR1 Allele bins | | 5_34 | | not pathogenic | 20301558 |
| | | 35_44 | | not pathogenic | 20301558 |
| | | 45_54 | | not pathogenic | 20301558 |
| | | 55_200 | | not pathogenic | 20301558 |
| | | >200 | | pathogenic | 20301558 |
| 146993469-147032647 | | ref | ref\|ref | 0 pathogenic alleles | 1302032 |
| 146991854-146993640 | | ref | ref\|ref | 0 pathogenic alleles | 8069307 |
| 147003450-147003451 | | GG | GG\|GG | 0 pathogenic alleles | 7670500 |
| NM_002024.5: c.990 + 14C > T | | T | T\|T | 0 pathogenic alleles | 9375856 |
| NM_002024.5: r.602delA | | C | C\|C | 0 pathogenic alleles | 7670500 |

FMR1-related primary ovarian insufficiency
Known Pathogenic Variants

| Variant Name | Effect | Reference Allele | Patient Genotype | Finding | Reference (URL or PMID) |
|---|---|---|---|---|---|
| NM_002024.5: r.101_103CGG(5_3000) | UTR | (5_44) | 58\|10 | 1 pathogenic allele | 20301558 |
| FMR1 Allele bins | | 5_34 | | not pathogenic | 20301558 |
| | | 35_44 | | not pathogenic | 20301558 |
| | | 45_54 | | not pathogenic | 20301558 |
| | | 55_200 | | pathogenic | 20301558 |
| | | >200 | | not pathogenic | 20301558 |

Fragile X-associated tremor and ataxia syndrome
Known Pathogenic Variants

| Variant Name | Effect | Reference Allele | Patient Genotype | Finding | Reference (URL or PMID) |
|---|---|---|---|---|---|
| NM_002024.5: r.101_103CGG(5_3000) | UTR | (5_44) | 58\|10 | 1 pathogenic allele | 20301558 |
| FMR1 Allele bins | | 5_34 | | not pathogenic | 20301558 |
| | | 35_44 | | not pathogenic | 20301558 |
| | | 45_54 | | not pathogenic | 20301558 |
| | | 55_200 | | pathogenic | 20301558 |
| | | >200 | | not pathogenic | 20301558 |

This report was reviewed and approved by:
Rungood E-Signature <Date>
Dr. Rungood, Laboratory Director
Appendix
Test Names:
  Physicians can order a test by GeneName or ConditionName. However we will report on conditions. This is because a gene can be involved in one or more conditions and it is possible that we have not curated variants for the other condition.
Definitions:
Ethnicity
  Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.
Pathogenic (Known)—ACMG Category 1
  We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.
Pathogenic (Novel)—ACMG Category 2
  Novel pathogenic mutations for qualitative reports are those that have not been described in an affected individual and result in a deleterious mutation (such as nonsense, truncation, disruption of consensus splice site, or disruption of the initiator codon).
Ref Allele
  Refers to the allele present at that coordinate in GRCh37. In some cases the reference allele might be the risk allele.

Sequence

The consensus base call and coverage is provided for each base sequenced. In addition a variant file for the individual is produced which contains information about positions that differ from the reference genome.

Variant of Unknown Significance (VUS)—ACMG Categories 3-6

A variant of unknown significance may have been observed in affected individuals but does not meet the criteria of pathogenicity or may be a novel variant with unclear functional effect. We provide frequency information and computational prediction for the functional effect of these variants.

General Disclaimer:

DNA studies do not constitute a definitive test for the selected condition(s) in all individuals. It should be realized that there are many possible sources of diagnostic error. Genotyping errors can result from trace contamination of PCR reactions and from rare genetic variants that interfere with analysis. This test is used for clinical purposes. It should not be regarded as investigational or for research. The laboratory is regulated under CLIA of 1988.

EXAMPLE 5

Test for All Conditions in the Locus Database

In one example, a requisition is submitted for all conditions in the Locus Database The requisition originates from any of a clinician, company, partner, or individual. The requisition is submitted electronically, on paper, via web service, from an EMR/PHR, or other means. The sample [blood, saliva, or cells, etc.] is de-identified and an encrypted ID is assigned. DNA from the sample associated with the requisition is purified and quality assessed for downstream processing. The sample is prepared for sequencing with respect to the regions of interest as defined by the Curation Database. All sequence relevant to any curated loci of interest and/or genes relevant for conditions of interest is targeted for downstream sequencing by a combination of targeting methodologies, in this case by targeted hybridization and 'pull down' of selected regions in addition to targeted amplification of selected regions. The sequencing is performed with one or more sequencing/analysis platforms and quality monitored for per base, per locus, coordinate, and condition quality statistics, ultimately enabling sensitivity, specificity and accuracy statistics to be resolved on a per base, locus, coordinate or condition basis. The Requisition Engine performs the secondary analysis on the regions of interest as indicated by the client in the sample requisition, in this case for all conditions in the Locus Database. The client/patient ID informs the regions for the Analysis Engine to interpret and per-condition results are determined. The data for the results are made available to be delivered as [a PDF, API for integration into electronic records, fax, etc.]

TABLE 13

| Requisition | | | | |
|---|---|---|---|---|
| | | | | CONFIDENTIAL [UPC Code] |
| PATIENT | | SPECIMEN | | PHYSICIAN |
| Name: | Patient 0 | Lab #: | NA18506 | Dr. Feelgood |
| DOB: | Sept. 30, 1973 | Specimen type: | DNA | 123 University Dr. |
| MRN: | JK69503 | Sample received: | 02/03/2012 | Room 301 |
| Gender: | Male | Report date: | 02/04/2012 | Los Angeles, CA 90025 |
| Race: | Black/African-American | | | |
| Order | | | | |
| Ordered Condition | Reported Conditions | Genes | Qualitative Report (Select all that apply for each ordered condition) | Quantitative Report (Threshold for reporting summary findings) |
| ☒ Geneticus-Screen | All conditions* | Various | ☒ Pathogenic variants (known) | ☐ >95% population percentile |
| | | | ☐ Pathogenic variants (novel) | ☐ >70% absolute risk |
| | | | ☐ Variants of unknown significance | ☐ >40% residual lifetime risk |
| | | | | ☐ >3X relative risk |
| | | | ☐ Sequence data | ☐ Odds Ratios >2.0 or <0.5 |
| | | | | ☒ [>90%] [percentile] |

TABLE 14

| Summary results: | |
|---|---|
| Summary Results | |
| Succinylcholine sensitivity | NOT AT RISK: 0 risk haplotypes (Risk model: Autosomal recessive) |

Drug metabolism BCHE 1 decreased activity allele
(Risk model: Codominant)

| Variant Name | Known (PMID/URL) or Novel | Patient Diplotype | Findings |
|---|---|---|---|
| Typical | Known (15025799) | Typical\|K variant | 1 risk haplotype, 1 non-risk haplotype |
| K variant | Known (15025799) | | |

| | |
|---|---|
| Congenital bilateral absence of the vas deferens | NOT AT RISK: 0 pathogenic variants |
| Cystic fibrosis | NOT AT RISK: 0 pathogenic variants |

Cystic fibrosis, modifier MBL2

Not at risk of reduced survival

| Variant Name | Known (PMID/URL) or Novel | Patient Diplotype | Findings |
|---|---|---|---|
| HapA | Known (17158822) | HapA\|HapA | 2 non-risk haplotypes |

Cystic fibrosis, modifier TGFB1

Lower lung function

| Variant Name | Known (PMID/URL) or Novel | Patient Diplotype | Findings |
|---|---|---|---|
| Hap4 | Known (16896927) | Hap4\|Hap4 | 2 risk haplotypes |

Modifier of CFTR related conditions*

| Variant Name | Alias or Protein Change | Known (PMID) or Novel | Ref Allele | Patient Genotype | Findings |
|---|---|---|---|---|---|
| NM_000492.3: c.1210-12T(5_9) | polyT tract | Known (7739684) | T(7) | T(5)\|T(7) | 1 non-ref allele |
| NM_000492.3: c.1210-34_33TG(8_13) | polyTG tract | Known (16020494) | TG(11) | TG(11)\|TG(11) | 0 non-ref alleles |
| NM_000492.3: c.350G > A | R117H | Known (15371902) | A | A\|A | 0 non-ref alleles |

*Consider submitting parental samples so that phase may be determined.

| Plavix (Clopidogrel Bisulfate) response | Intermediate effectiveness: 1 risk haplotype |
|---|---|
| Known (PMID/URL) | (Risk model: Plavix response) |

| Variant Name | or Novel | Patient Diplotype | Findings |
|---|---|---|---|
| CYP2C19*1 | Known (URL*) | CYP2C19*1\|CYP2C19*2 | 1 risk haplotype, 1 non-risk haplotype |
| CYP2C19*2 | Known (URL*) | | |

*URL and access date: http://www.cypalleles.ki.se/cyp2c19.htm_091310

| Drug metabolism CYP2C19 | Intermediate metabolizer: 1 risk haplotype |
|---|---|
| Known (PMID/URL) | (Risk model: CYP2C19 matrix) |

| Variant Name | or Novel | Patient Diplotype | Findings |
|---|---|---|---|
| CYP2C19*1 | Known (URL*) | CYP2C19*1\|CYP2C19*2 | 1 risk haplotype, 1 non-risk haplotype |
| CYP2C19*2 | Known (URL*) | | |

*URL and access date: http://www.cypalleles.ki.se/cyp2c19.htm_091310

| | |
|---|---|
| Abacavir drug-induced hypersensitivity | NOT AT RISK: 0 pathogenic variants |
| Carbamazepine drug-induced cutaneous adverse events | NOT AT RISK: 0 pathogenic variants |
| Flucloxacillin drug-induced liver injury | NOT AT RISK: 0 pathogenic variants |

TABLE 14-continued

|  |  |  | significant efficacy [CHD event reduction with statin therapy]: 1 pathogenic variant | | |
|---|---|---|---|---|---|
| Statin response modifier | | | Patient | | |
| Variant Name | Alias | Known (PMID) or Novel | Ref Allele | Genotype | Findings |
| CVID0000119 |  | Known (20854963) | A | A\|G | 1 pathogenic allele |

| 46, XY DSD | | | | | |
|---|---|---|---|---|---|
|  |  | Known | Genotype Report | | |
| Variant Name | Alias | (PMID) or Novel | Ref Allele | Patient Genotype | Findings |
| CVID1001793 | NM_004959.4: c.437 | Known (14623279) | C | G\|G | 2 non-ref alleles |
| 54 variants - see LocusDevelopment | Various | Various | Various | Various | 0 non-ref alleles |

| | |
|---|---|
| Basal cell carcinoma, sporadic | unknown: no information for this ancestry |
| Colorectal cancer, sporadic | unknown: no information for this ancestry |
| Cutaneous melanoma, sporadic | unknown: no information for this ancestry |
| Ovarian cancer, sporadic | unknown: no information for this ancestry |
| Sporadic diffuse gastric cancer | unknown: no information for this ancestry |
| Thyroid cancer, sporadic | unknown: no information for this ancestry |
| Geneticus-Screen | NOT AT RISK: 0 pathogenic variants Negative for >90% percentile |

TABLE 15

Detailed findings

| Variant Name | Alias or Protein Change | Effect | Ref Allele | Patient Genotype | Findings | Reference (URL or PMID) |
|---|---|---|---|---|---|---|
| Detailed Findings Succinylcholine sensitivity Known pathogenic variants - haplotype details | | | | | | |
| Alleles | | | | | | |
| CVID0000120 | na |  | T | T\|T | 0 non-ref alleles | 15025799 |
| CVID0000146 | na |  | T | T\|T | 0 non-ref alleles | 15025799 |
| CVID0000121 | na |  | C | C\|T | 1 non-ref allele | 15025799 |
| Haplotypes | | | | | | |
| Typical |  | normal | TTC | TTC | 1 non-risk haplotype | 15025799 |
| J variant |  | decreased activity | TAT |  | 0 risk haplotypes | 15025799 |
| AK variant |  | decreased activity | CTT |  | 0 risk haplotypes | 15025799 |
| A variant |  | decreased activity | CTC |  | 0 risk haplotypes | 15025799 |
| K variant |  | decreased activity | TTT | TTT | 1 non-risk haplotype | 15025799 |
| Patient Diplotype |  | Typical\|K variant |  |  | Not at risk |  |

TABLE 15-continued

Detailed findings

Drug metabolism BCHE
Known pathogenic variants - haplotype details

Alleles

| | | | | | |
|---|---|---|---|---|---|
| CVID0000120 | na | T | T\|T | 0 non-ref alleles | 15025799 |
| CVID0000146 | na | T | T\|T | 0 non-ref alleles | 15025799 |
| CVID0000121 | na | C | C\|T | 1 non-ref allele | 15025799 |

Haplotypes

| | | | | | |
|---|---|---|---|---|---|
| Typical | normal | TTC | TTC | 1 non-risk haplotype | 15025799 |
| J variant | decreased activity | TAT | | 0 risk haplotypes | 15025799 |
| AK variant | decreased activity | CTT | | 0 risk haplotypes | 15025799 |
| A variant | decreased activity | CTC | | 0 risk haplotypes | 15025799 |
| K variant | decreased activity | TTT | TTT | 1 risk haplotype | 15025799 |
| Patient Diplotype | Typical\|K variant | | | 1 decreased activity haplotype | |

| Variant Name | Alias or Protein Change | Effect | Reference Allele | Patient Genotype | Findings | Reference (URL or PMID) |
|---|---|---|---|---|---|---|

Succinylcholine sensitivity
Known Pathogenic Variants - Negative Results

| | | | | | | |
|---|---|---|---|---|---|---|
| 49 variants - see Locus Development | Various | Various | Various | Various | 0 pathogenic alleles | Various |

Drug metabolism BCHE
Known Pathogenic Variants - Negative Results

| | | | | | | |
|---|---|---|---|---|---|---|
| 49 variants - see Locus Development | Various | Various | Various | Various | 0 pathogenic alleles | Various |

| Variant Name | Alias or Protein Change | Effect | Ref Allele | Patient Genotype | Findings | Reference (URL or PMID) |
|---|---|---|---|---|---|---|

Cystic fibrosis, modifier MBL2
Modifier condition - Known Pathogenic Variants

Alleles

| | | | | | | |
|---|---|---|---|---|---|---|
| NM_000242.2: c.154C > T | MBL2*D | na | G | G\|A | 1 non-ref allele | 17158822 |
| NM_000242.2: c.161G > A | MBL2*B | na | C | C\|T | 1 non-ref allele | 17158822 |
| NM_000242.2: c.170G > A | MBL2*C | na | C | C\|C | 0 non-ref alleles | 17158822 |

Haplotypes

| | | | | | | |
|---|---|---|---|---|---|---|
| MBL2 Haplotype O_a | | Low MBL2 protein level | ACC | | 0 risk haplotype | 17158822 |
| MBL2 Haplotype O_b | | Low MBL2 protein level | GTC | | 0 risk haplotype | 17158822 |
| MBL2 Haplotype O_c | | Low MBL2 protein level | GCT | | 0 risk haplotypes | 17158822 |
| MBL2 Haplotype A | | Normal activity | GCC | GCC\|GCC | 2 non-risk haplotypes | 17158822 |
| Patient Diplotype | | HapA\|HapA | | | Not at risk of reduced survival | |

TABLE 15-continued

Detailed findings

Cystic fibrosis, modifier TGFB1
Modifier condition - Known Pathogenic Variants Alleles

| | | | | | | |
|---|---|---|---|---|---|---|
| CVID1001284 | TGFB1-509 promoter | na | G | G\|A | 1 non-ref allele | 16896927 |
| CVID1001285 | TGFB1-codon10 | na | A | A\|G | 1 non-ref allele | 16896927 |
| CVID1001395 | TGFB1-intron5 | na | G | G\|G | 0 non-ref alleles | 16896927 |

Haplotypes

| | | | | | |
|---|---|---|---|---|---|
| TGFB1 Haplotype Hap1 | Normal TGFB1 levels | GGG | | 0 unk* haplotypes | 16896927 |
| TGFB1 Haplotype Hap2 | Normal TGFB1 levels | GAG | | 0 risk haplotypes | 16896927 |
| TGFB1 Haplotype Hap3 | Normal TGFB1 levels | GAA | | 0 unk* haplotypes | 16896927 |
| TGFB1 Haplotype Hap4 | Increased plasma TGFB1 levels | AGG | AGG\|AGG | 2 risk haplotypes | 16896927 |
| TGFB1 Haplotype Hap5 | Increased plasma TGFB1 levels | AGA | | 0 unk* haplotypes | 16896927 |
| Patient Diplotype | Hap4\|Hap4 | | | Lower lung function | |

| Variant Name | Alias or Protein Change | Effect | Reference Allele | Patient Genotype | Findings | Reference (URL or PMID) |
|---|---|---|---|---|---|---|

Congenital bilateral absence of the vas deferens
Known Pathogenic Variants - Negative Results

| | | | | | | |
|---|---|---|---|---|---|---|
| 66 variants - see Locus Development | Various | Various | Various | Various | 0 pathogenic alleles | Various |

Cystic fibrosis
Known Pathogenic Variants - Negative Results

| | | | | | | |
|---|---|---|---|---|---|---|
| 584 variants - see Locus Development | Various | Various | Various | Various | 0 pathogenic alleles | Various |

| Variant Name | Alias or Protein Change | Effect | Ref Allele | Patient Genotype | Findings | Reference (URL or PMID) |
|---|---|---|---|---|---|---|

Plavix (Clopidogrel Bisulfate) response
Known pathogenic variants - haplotype details Alleles

| | | | | | | |
|---|---|---|---|---|---|---|
| CVID0000018 | | na | G | G\|A | 1 non-ref allele | URL* |
| CVID0000019 | | na | G | G\|G | 0 non-ref alleles | URL* |
| CVID0000020 | | na | A | A\|G | 0 non-ref alleles | URL* |
| CVID0000021 | | na | C | C\|C | 0 non-ref alleles | URL* |
| CVID0000022 | | na | G | G\|G | 0 non-ref alleles | URL* |
| CVID0000023 | | na | T | T\|T | 0 non-ref alleles | URL* |
| CVID0000024 | | na | T | T\|T | 0 non-ref alleles | URL* |
| CVID0000025 | | na | G | G\|G | 0 non-ref alleles | URL* |

Haplotypes

| | | | | | | |
|---|---|---|---|---|---|---|
| default | CYP2C19*1 | normal | XXXXXXX | XXXXXXX | 1 non-risk haplotype | URL* |
| CYP2C19*2 | | decreased activity | AGACGTTG | AGACGTTG | 1 risk haplotype | URL* |
| CYP2C19*3 | | decreased activity | GAACGTTG | | 0 risk haplotypes | URL* |
| CYP2C19*4 | | decreased activity | GGGCGTTG | | 0 unk^ haplotypes | URL* |
| CYP2C19*5 | | decreased activity | GGATGTTG | | 0 unk haplotypes | URL* |

TABLE 15-continued

Detailed findings

| | | | | | |
|---|---|---|---|---|---|
| CYP2C19*6 | decreased activity | GGACATTG | | 0 unk haplotypes | URL* |
| CYP2C19*7 | decreased activity | GGACGATG | | 0 unk haplotypes | URL* |
| CYP2C19*8 | decreased activity | GGACGTCG | | 0 unk haplotypes | URL* |
| CYP2C19*17 | increased activity | GGACGTTA | | 0 risk haplotypes | URL* |
| Patient Diplotype | CYP2C19*1\|CYP2C19*2 | | | Intermediate effectiveness | |

Drug metabolism CYP2C19
Known pathogenic variants - haplotype details

Alleles

| | | | | | |
|---|---|---|---|---|---|
| CVID0000018 | na | G | G\|A | 1 non-ref allele | URL* |
| CVID0000019 | na | G | G\|G | 0 non-ref alleles | URL* |
| CVID0000020 | na | A | A\|G | 0 non-ref alleles | URL* |
| CVID0000021 | na | C | C\|C | 0 non-ref alleles | URL* |
| CVID0000022 | na | G | G\|G | 0 non-ref alleles | URL* |
| CVID0000023 | na | T | T\|T | 0 non-ref alleles | URL* |
| CVID0000024 | na | T | T\|T | 0 non-ref alleles | URL* |
| CVID0000025 | na | G | G\|G | 0 non-ref alleles | URL* |

Haplotypes

| | | | | | | |
|---|---|---|---|---|---|---|
| default | CYP2C19*1 | normal | XXXXXXXX | XXXXXXXX | 1 non risk haplotype | URL* |
| CYP2C19*2 | | decreased activity | AGACGTTG | AGACGTTG | 1 risk haplotype | URL* |
| CYP2C19*3 | | decreased activity | GAACGTTG | | 0 risk haplotypes | URL* |
| CYP2C19*4 | | decreased activity | GGGCGTTG | | 0 unk^ haplotypes | URL* |
| CYP2C19*5 | | decreased activity | GGATGTTG | | 0 unk haplotypes | URL* |
| CYP2C19*6 | | decreased activity | GGACATTG | | 0 unk haplotypes | URL* |
| CYP2C19*7 | | decreased activity | GGACGATG | | 0 unk haplotypes | URL* |
| CYP2C19*8 | | decreased activity | GGACGTCG | | 0 unk haplotypes | URL* |
| CYP2C19*17 | | increased activity | GGACGTTA | | 0 risk haplotypes | URL* |
| Patient Diplotype | | CYP2C19*1\|CYP2C19*2 | | | Intermediate metabolizer | |

Abacavir drug-induced hypersensitivity
Known pathogenic variants - haplotype details

Alleles

| | | | | | |
|---|---|---|---|---|---|
| CVID0000174 | na | A | A\|A | 0 non-ref alleles | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| CVID0000181 | na | T | T\|T | 0 non-ref alleles | dbMHC |
| CVID0000182 | na | G | A\|G | 1 non-ref allele | dbMHC |
| CVID0000183 | na | C | C\|G | 1 non-ref allele | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|C | 0 non-ref alleles | dbMHC |
| CVID0000192 | na | C | C\|C | 0 non-ref alleles | dbMHC |
| CVID0000193 | na | C | C\|G | 1 non-ref allele | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

TABLE 15-continued

Detailed findings

Haplotypes

| | | | | | |
|---|---|---|---|---|---|
| HLAB*1502 | HLAB*1502 | CCTGTCCTGGCG GACTACCCGCA (SEQ ID NO: 2) | | 0 non-risk haplotypes | dbMHC |
| HLAB*5701 | HLAB*5701 | CCCACTCAGGGGT CTACCCGCA (SEQ ID NO: 1) | | 0 risk haplotypes | dbMHC |
| default | not HLAB*1502, not HLAB*5701 | XXXXXXXXXXXX XXXXXXXXXX | XXXXXXXXX XXXXXXXXX XXX | 2 non-risk haplotypes | dbMHC |
| Patient Diplotype | default\|default | | | Not at risk | |

Carbamazepine drug-induced cutaneous adverse events
Known pathogenic variants - haplotype details Alleles

| | | | | | |
|---|---|---|---|---|---|
| CVID0000174 | na | A | A\|A | 0 non-ref alleles | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| CVID0000181 | na | T | T\|T | 0 non-ref alleles | dbMHC |
| CVID0000182 | na | G | A\|G | 1 non-ref allele | dbMHC |
| CVID0000183 | na | C | C\|G | 1 non-ref allele | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|C | 0 non-ref alleles | dbMHC |
| CVID0000192 | na | C | C\|C | 0 non-ref alleles | dbMHC |
| CVID0000193 | na | C | C\|G | 1 non-ref allele | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

Haplotypes

| | | | | | |
|---|---|---|---|---|---|
| HLAB*1502 | HLAB*1502 | CCTGTCCTGGCG GACTACCCGCA (SEQ ID NO: 2) | | 0 risk haplotypes | dbMHC |
| HLAB*5701 | HLAB*5701 | CCCACTCAGGGGT CTACCCGCA (SEQ ID NO: 1) | | 0 non-risk haplotypes | dbMHC |
| default | not HLAB*1502, not HLAB*5701 | XXXXXXXXXXXX XXXXXXXXXX | XXXXXXXXX XXXXXXXXX XXX | 2 non-risk haplotypes | dbMHC |
| Patient Diplotype | | | default\|default | Not at risk | |

Flucloxacillin drug-induced liver injury
Known pathogenic variants - haplotype details Alleles

| | | | | | |
|---|---|---|---|---|---|
| CVID0000174 | na | A | A\|A | 0 non-ref alleles | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| CVID0000181 | na | T | T\|T | 0 non-ref alleles | dbMHC |
| CVID0000182 | na | G | A\|G | 1 non-ref allele | dbMHC |
| CVID0000183 | na | C | C\|G | 1 non-ref allele | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |

TABLE 15-continued

Detailed findings

| | | | | | |
|---|---|---|---|---|---|
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|C | 0 non-ref alleles | dbMHC |
| CVID0000192 | na | C | C\|C | 0 non-ref alleles | dbMHC |
| CVID0000193 | na | C | C\|G | 1 non-ref allele | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

Haplotypes

| | | | | | |
|---|---|---|---|---|---|
| HLAB*1502 | HLAB*1502 | CCTGTCCTGGCG GACTACCCGCA (SEQ ID NO: 2) | | 0 non-risk haplotypes | dbMHC |
| HLAB*5701 | HLAB*5701 | CCCACTCAGGGGT CTACCCGCA (SEQ ID NO: 1) | | 0 risk haplotypes | dbMHC |
| default | not HLAB*1502, not HLAB*5701 | XXXXXXXXXXXX XXXXXXXXXX | XXXXXXXXXX XXXXXXXXXX XXX | 2 non-risk haplotypes | dbMHC |
| Patient Diplotype | | | default\|default | Not at risk | |

| Variant Name | Alias or Protein Change | Effect | Reference Allele | Patient Genotype | Findings | Reference (URL or PMID) |
|---|---|---|---|---|---|---|

Statin response modifier
Known Pathogenic Variants - Detail Results

| Variant Name | Alias or Protein Change | Effect | Reference Allele | Patient Genotype | Findings | Reference (URL or PMID) |
|---|---|---|---|---|---|---|
| CVID0000119 | NP_659464.3: p.Trp719Arg | missense | A | A\|G | 1 pathogenic allele | 20854963 |

Geneticus-Screen
Known Pathogenic Variants - Negative Results

| Variant Name | Alias or Protein Change | Effect | Reference Allele | Patient Genotype | Findings | Reference (URL or PMID) |
|---|---|---|---|---|---|---|
| 4598 variants - see Locus Development | Various | Various | Various | Various | 0 pathogenic alleles | Various |

*Unk = no published information on genotype:phenotype relationship
*URL and access date: http://www.cypalleles.ki.se/cyp2c19.htm_091310
^unk = no published information on genotype:phenotype relationship This report was reviewed and approved by:
Rungood E-signature <Date>
Dr. Rungood, Laboratory Director
Appendix
Test Names:

Physicians can order a test by GeneName or ConditionName. However we will report on conditions. This is because a gene can be involved in one or more conditions and it is possible that we have not curated variants for the other condition.
Definitions:
Ethnicity Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.
Pathogenic (Known)—ACMG Category 1

We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.
Pathogenic (Novel)—ACMG Category 2

Novel pathogenic mutations for qualitative reports are those that have not been described in an affected individual and result in a deleterious mutation (such as nonsense, truncation, disruption of consensus splice site, or disruption of the initiator codon).
Ref Allele Refers to the allele present at that coordinate in GRCh37. In some cases the reference allele might be the risk allele.
Sequence The consensus base call and coverage is provided for each base sequenced. In addition a variant file for the individual is produced which contains information about positions that differ from the reference genome.

Variant of Unknown Significance (VUS)—ACMG Categories 3-6

A variant of unknown significance may have been observed in affected individuals but does not meet the criteria of pathogenicity or may be a novel variant with unclear functional effect. We provide frequency information and computational prediction for the functional effect of these variants.

General Disclaimer:

DNA studies do not constitute a definitive test for the selected condition(s) in all individuals. It should be realized that there are many possible sources of diagnostic error. Genotyping errors can result from trace contamination of PCR reactions and from rare genetic variants that interfere with analysis. This test is used for clinical purposes. It should not be regarded as investigational or for research. The laboratory is regulated under CLIA of 1988.

EXAMPLE 6

Test for All Conditions in the Locus Database with Client Generated Sequence

In this example, a requisition is submitted for all conditions-in the Locus Database. The requisition originates from any of a clinician, company, partner, or individual. The requisition is submitted electronically, on paper, via web service, from an EMR/PHR, or other means, including the sequence to be analyzed by Locus Development. Per base, per locus, coordinate, and condition quality statistics for the requisitioned sequence are determined by the Locus Analysis ultimately enabling sensitivity, specificity and accuracy statistics to be resolved on a per base, locus, coordinate or condition basis. The Requisition Engine performs the secondary analysis on the regions of interest as indicated by the client in the sample requisition, in this case variants for all conditions in the Locus Database. The client/patient ID informs the regions for the Analysis Engine to interpret and per-condition results are determined. The data for the results are made available to be delivered as [a PDF, API for integration into electronic records, fax, etc.] as per client's instruction. In this case, the client's preferences are to receive results for known pathogenic variants, as well as novel variants and variants of unknown significance. The data may be used by the client directly, or reformatted into a clinical report summarizing the key information for a patient.

TABLE 16

Requisition

CONFIDENTIAL
[UPC Code]

| PATIENT | | SPECIMEN | | PHYSICIAN |
|---|---|---|---|---|
| Name: | Patient 0 | Lab #: | NA18508 | Dr. Feelgood |
| DOB: | Sept. 30, 1973 | Specimen type: | DNA | 123 University Dr. |
| MRN: | JK69503 | Sample received: | 02/03/2012 | Room 301 |
| Gender: | Female | Report date: | 02/04/2012 | Los Angeles, CA 90025 |
| Race: | Black/African-American | | | |

Order Details

| Ordered Condition | Reported Conditions | Genes | Qualitative Report (Select all that apply for each ordered condition) | Quantitative Report (Threshold for reporting summary findings) |
|---|---|---|---|---|
| ☒ Geneticus-Screen | All conditions* | Various | ☒ Pathogenic variants (known)<br>☐ Pathogenic variants (novel)<br>☒ Variants of unknown significance<br>☐ Sequence data | ☐ >95% population percentile<br>☐ >70% absolute risk<br>☐ >40% residual lifetime risk<br>☐ >3X relative risk<br>☐ Odds Ratios >2.0 or <0.5<br>☒ [>90%] [percentile] |

TABLE 17

Summary Results

Summary Results
Succinylcholine sensitivity — NOT AT RISK: 0 risk haplotypes (Risk model: Autosomal recessive)

Drug metabolism BCHE — 1 decreased activity allele (Risk model: Codominant)

| Variant Name | Known (PMID/URL) or Novel | Patient Diplotype | Findings |
|---|---|---|---|
| Typical | Known (15025799) | Typical|K variant | 1 risk haplotype, 1 non-risk haplotype |
| K variant | Known (15025799) | | |

TABLE 17-continued

| | |
|---|---|
| Congenital bilateral absence of the vas deferens | NOT AT RISK: 0 pathogenic variants |
| Cystic fibrosis | NOT AT RISK: 0 pathogenic variants |

Cystic fibrosis, modifier MBL2

| | | Not at risk of reduced survival | |
|---|---|---|---|
| Variant Name | Known (PMID/URL) or Novel | Patient Diplotype | Findings |
| HapA | Known (17158822) | HapO_b|HapA | 1 non-risk haplotype |
| HapO_b | Known (17158822) | | 1 risk haplotype |

Modifier of CFTR related conditions*

| Variant Name | Alias or Protein Change | Known (PMID) or Novel | Ref Allele | Genotype Report Patient Genotype | Findings |
|---|---|---|---|---|---|
| NM_000492.3: c.1210-12T(5_9) | polyT tract | Known (7739684) | T(7) | T(7)|T(7) | 0 non-ref alleles |
| NM_000492.3: c.1210-34_33TG(8_13) | polyTG tract | Known (16020494) | TG(11) | TG(9)|TG(11) | 1 non-ref alleles |
| NM_000492.3: c.350G > A | R117H | Known (15371902) | A | A|A | 0 non-ref alleles |

*Consider submitting parental samples so that phase may be determined.

| Plavix (Clopidogrel Bisulfate) response | | Intermediate effectiveness: 1 risk haplotype | |
|---|---|---|---|
| Variant Name | Known (PMID/URL) or Novel | (Risk model: Plavix reponse) Patient Diplotype | Findings |
| CYP2C19*1 | Known (URL*) | CYP2C19*1|CYP2C19*2 | 1 risk haplotype, 1 non-risk haplotype |
| CYP2C19*2 | Known (URL*) | | |

*URL and access date: http://www.cypalleles.ki.se/cyp2c19.htm_091310

| Drug metabolism CYP2C19 | | Intermediate metabolizer: 1 risk haplotype | |
|---|---|---|---|
| | | (Risk model: CYP2C19 matrix) | |
| CYP2C19*1 | Known (URL*) | CYP2C19*1|CYP2C19*2 | 1 risk haplotype, 1 non-risk haplotype |
| CYP2C19*2 | Known (URL*) | | |

*URL and access date: http://www.cypalleles.ki.se/cyp2c19.htm_091310

| | |
|---|---|
| Abacavir drug-induced hypersensitivity | NOT AT RISK: 0 pathogenic variants |
| Carbamazepine drug-induced cutaneous adverse events | NOT AT RISK: 0 pathogenic variants |
| Flucloxacillin drug-induced liver injury | NOT AT RISK: 0 pathogenic variants |

| Statin response modifier | | | | insignificant efficacy [CHD event reduction with statin therapy]: 2 pathogenic variants | |
|---|---|---|---|---|---|
| Variant Name | Alias | Known (PMID) or Novel | Ref Allele | Patient Genotype | Findings |
| CVID0000119 | | Known (20854963) | A | G|G | 2 pathogenic alleles |

46, XY DSD

| Variant Name | Alias | Known (PMID) or Novel | Ref Allele | Genotype Report Patient Genotype | Findings |
|---|---|---|---|---|---|
| CVID1001793 | NM_004959.4: c.437 | Known (14623279) | C | G|G | 2 non-ref alleles |
| 54 variants - see LocusDevelopment | Various | Various | Various | Various | 0 non-ref alleles |

TABLE 17-continued

| | |
|---|---|
| Breast cancer, sporadic | NOT AT RISK<br>Negative for 90% percentile |

| Drug metabolism CYP2B6 | Intermediate metabolizer: 1 risk haplotype |
|---|---|
| Known (PMID/URL) | (Risk model: CYP2B6 matrix) |

| Variant Name | Known (PMID/URL) or Novel | Patient Diplotype | Findings |
|---|---|---|---|
| CYP2B6*1 | Known (19225447) | CYP2B6*1\|CYP2B6*6 | 1 risk haplotype, 1 non-risk haplotype |
| CYP2B6*6 | Known (19225447) | | |

| | |
|---|---|
| Basal cell carcinoma, sporadic | unknown: no information for this ancestry |
| Colorectal cancer, sporadic | unknown: no information for this ancestry |
| Cutaneous melanoma, sporadic | unknown: no information for this ancestry |
| Ovarian cancer, sporadic | unknown: no information for this ancestry |
| Sporadic diffuse gastric cancer | unknown: no information for this ancestry |
| Thyroid cancer, sporadic | unknown: no information for this ancestry |
| Geneticus-Screen | NOT AT RISK: 0 pathogenic variants<br>Negative for >90% percentile |

TABLE 18

Detailed Findings

| Variant Name | Alias or Protein Change | Effect | Ref Allele | Patient Genotype | Findings | Reference (URL or PMID) |
|---|---|---|---|---|---|---|
| | | | | | | |

Detailed Findings
Succinylcholine sensitivity
Known pathogenic variants - haplotype details

Alleles

| | | | | | | |
|---|---|---|---|---|---|---|
| CVID0000120 | na | | T | T\|T | 0 non-ref alleles | 15025799 |
| CVID0000146 | na | | T | T\|T | 0 non-ref alleles | 15025799 |
| CVID0000121 | na | | C | C\|T | 1 non-ref allele | 15025799 |

Haplotypes

| | | | | | | |
|---|---|---|---|---|---|---|
| Typical | | normal | TTC | TTC | 1 non-risk haplotype | 15025799 |
| J variant | | decreased activity | TAT | | 0 risk haplotypes | 15025799 |
| AK variant | | decreased activity | CTT | | 0 risk haplotypes | 15025799 |
| A variant | | decreased activity | CTC | | 0 risk haplotypes | 15025799 |
| K variant | | decreased activity | TTT | TTT | 1 non-risk haplotype | 15025799 |
| Patient Diplotype | | Typical\|K variant | | | Not at risk | |

Drug metabolism BCHE
Known pathogenic variants - haplotype details

Alleles

| | | | | | | |
|---|---|---|---|---|---|---|
| CVID0000120 | na | | T | T\|T | 0 non-ref alleles | 15025799 |
| CVID0000146 | na | | T | T\|T | 0 non-ref alleles | 15025799 |
| CVID0000121 | na | | C | C\|T | 1 non-ref allele | 15025799 |

Haplotypes

| | | | | | | |
|---|---|---|---|---|---|---|
| Typical | | normal | TTC | TTC | 1 non-risk haplotype | 15025799 |
| J variant | | decreased activity | TAT | | 0 risk haplotypes | 15025799 |

TABLE 18-continued

Detailed Findings

| | | | | | | |
|---|---|---|---|---|---|---|
| AK variant | | decreased activity | CTT | | 0 risk haplotypes | 15025799 |
| A variant | | decreased activity | CTC | | 0 risk haplotypes | 15025799 |
| K variant | | decreased activity | TTT | TTT | 1 risk haplotype | 15025799 |
| Patient Diplotype | | Typical\|K variant | | | 1 decreased activity haplotype | |

| Variant Name | Alias or Protein Change | Effect | Reference Allele | Patient Genotype | Findings | Reference (URL or PMID) |
|---|---|---|---|---|---|---|
| | | Succinylcholine sensitivity Known Pathogenic Variants - Negative Results | | | | |
| 49 variants - see Locus Development | Various | Various | Various | Various | 0 pathogenic alleles | Various |
| | | Drug metabolism BCHE Known Pathogenic Variants - Negative Results | | | | |
| 49 variants - see Locus Development | Various | Various | Various | Various | 0 pathogenic alleles | Various |

| Variant Name | Alias or Protein Change | Effect | Ref Allele | Patient Genotype | Findings | Reference (URL or PMID) |
|---|---|---|---|---|---|---|
| | | Cystic fibrosis, modifier MBL2 Modifier condition - Known Pathogenic Variants | | | | |
| Alleles | | | | | | |
| NM_000242.2: c.154C > T | MBL2*D | na | G | G\|G | 0 non-ref alleles | 17158822 |
| NM_000242.2: c.161G > A | MBL2*B | na | C | C\|T | 1 non-ref allele | 17158822 |
| NM_000242.2: c.170G > A | MBL2*C | na | C | C\|C | 0 non-ref alleles | 17158822 |
| Haplotypes | | | | | | |
| MBL2 Haplotype O_a | | Low MBL2 protein level | ACC | | 0 risk haplotype | 17158822 |
| MBL2 Haplotype O_b | | Low MBL2 protein level | GTC | GTC | 1 risk haplotype | 17158822 |
| MBL2 Haplotype O_c | | Low MBL2 protein level | GCT | | 0 risk haplotypes | 17158822 |
| MBL2 Haplotype A | | Normal activity | GCC | GCC | 1 non-risk haplotypes | 17158822 |
| Patient Diplotype | | HapO_b\|HapA | | | Not at risk of reduced survival | |
| | | Cystic fibrosis, modifier TGFB1 Modifier condition - Known Pathogenic Variants | | | | |
| Alleles | | | | | | |
| CVID1001284 | TGFB1-509 promoter | na | G | G\|A | 1 non-ref allele | 16896927 |
| CVID1001285 | TGF1-codon10 | na | A | A\|A | 0 non-ref alleles | 16896927 |
| CVID1001395 | TGFB1-intron5 | na | G | G\|G | 0 non-ref alleles | 16896927 |
| Haplotypes | | | | | | |
| TGFB1 Haplotype Hap1 | | Normal TGFB1 levels | GGG | | 0 unk* haplotypes | 16896927 |
| TGFB1 Haplotype Hap2 | | Normal TGFB1 levels | GAG | GAG | 0 risk haplotypes | 16896927 |
| TGFB1 Haplotype Hap3 | | Normal TGFB1 levels | GAA | | 0 unk* haplotypes | 16896927 |

TABLE 18-continued

Detailed Findings

| | | | | | | |
|---|---|---|---|---|---|---|
| TGFB1 Haplotype Hap4 | Increased plasma TGFB1 levels | AGG | | | 2 risk haplotypes | 16896927 |
| TGFB1 Haplotype Hap5 | Increased plasma TGFB1 levels | AGA | | | 0 unk* haplotypes | 16896927 |
| novel | unknown | AAG | AAG | | Variant of unknown significance | |
| Patient Diplotype | Hap4\|AAG | | | | unknown | |

| Variant Name | Alias or Protein Change | Effect | Reference Allele | Patient Genotype | Findings | Reference (URL or PMID) |
|---|---|---|---|---|---|---|

Congenital bilateral absence of the vas deferens
Known Pathogenic Variants - Negative Results

| | | | | | | |
|---|---|---|---|---|---|---|
| 66 variants - see Locus Development | Various | Various | Various | Various | 0 pathogenic alleles | Various |

Cystic fibrosis
Known Pathogenic Variants - Negative Results

| | | | | | | |
|---|---|---|---|---|---|---|
| 584 variants - see Locus Development | Various | Various | Various | Various | 0 pathogenic alleles | Various |

| Variant Name | Alias or Protein Change | Effect | Ref Allele | Patient Genotype | Findings | Reference (URL or PMID) |
|---|---|---|---|---|---|---|

Plavix (Clopidogrel Bisulfate) response
Known pathogenic variants - haplotype details Alleles

| | | | | | | |
|---|---|---|---|---|---|---|
| CVID0000018 | | na | G | G\|A | 1 non-ref allele | URL* |
| CVID0000019 | | na | G | G\|G | 0 non-ref alleles | URL* |
| CVID0000020 | | na | A | A\|G | 0 non-ref alleles | URL* |
| CVID0000021 | | na | C | C\|C | 0 non-ref alleles | URL* |
| CVID0000022 | | na | G | G\|G | 0 non-ref alleles | URL* |
| CVID0000023 | | na | T | T\|T | 0 non-ref alleles | URL* |
| CVID0000024 | | na | T | T\|T | 0 non-ref alleles | URL* |
| CVID0000025 | | na | G | G\|G | 0 non-ref alleles | URL* |

Haplotypes

| | | | | | | |
|---|---|---|---|---|---|---|
| default | CYP2C19*1 | normal | XXXXXXX | XXXXXXX | 1 non-risk haplotype | URL* |
| CYP2C19*2 | | decreased activity | AGACGTTG | AGACGTTG | 1 risk haplotype | URL* |
| CYP2C19*3 | | decreased activity | GAACGTTG | | 0 risk haplotypes | URL* |
| CYP2C19*4 | | decreased activity | GGGCGTTG | | 0 unk^ haplotypes | URL* |
| CYP2C19*5 | | decreased activity | GGATGTTG | | 0 unk haplotypes | URL* |
| CYP2C19*6 | | decreased activity | GGACATTG | | 0 unk haplotypes | URL* |
| CYP2C19*7 | | decreased activity | GGACGATG | | 0 unk haplotypes | URL* |
| CYP2C19*8 | | decreased activity | GGACGTCG | | 0 unk haplotypes | URL* |
| CYP2C19*17 | | increased activity | GGACGTTA | | 0 risk haplotypes | URL* |
| Patient Diplotype | CYP2C19*1\|CYP2C19*2 | | | | Intermediate effectiveness | |

TABLE 18-continued

Detailed Findings

Drug metabolism CYP2C19
Known pathogenic variants - haplotype details

Alleles

| | | | | | |
|---|---|---|---|---|---|
| CVID0000018 | na | G | G\|A | 1 non-ref allele | URL* |
| CVID0000019 | na | G | G\|G | 0 non-ref alleles | URL* |
| CVID0000020 | na | A | A\|G | 0 non-ref alleles | URL* |
| CVID0000021 | na | C | C\|C | 0 non-ref alleles | URL* |
| CVID0000022 | na | G | G\|G | 0 non-ref alleles | URL* |
| CVID0000023 | na | T | T\|T | 0 non-ref alleles | URL* |
| CVID0000024 | na | T | T\|T | 0 non-ref alleles | URL* |
| CVID0000025 | na | G | G\|G | 0 non-ref alleles | URL* |

Haplotypes

| | | | | | | |
|---|---|---|---|---|---|---|
| default | CYP2C19*1 | normal | XXXXXXXX | XXXXXXXX | 1 non-risk haplotype | URL* |
| CYP2C19*2 | | decreased activity | AGACGTTG | AGACGTTG | 1 risk haplotype | URL* |
| CYP2C19*3 | | decreased activity | GAACGTTG | | 0 risk haplotypes | URL* |
| CYP2C19*4 | | decreased activity | GGGCGTTG | | 0 unk^ haplotypes | URL* |
| CYP2C19*5 | | decreased activity | GGATGTTG | | 0 unk haplotypes | URL* |
| CYP2C19*6 | | decreased activity | GGACATTG | | 0 unk haplotypes | URL* |
| CYP2C19*7 | | decreased activity | GGACGATG | | 0 unk haplotypes | URL* |
| CYP2C19*8 | | decreased activity | GGACGTCG | | 0 unk haplotypes | URL* |
| CYP2C19*17 | | increased activity | GGACGTTA | | 0 risk haplotypes | URL* |
| Patient Diplotype | | CYP2C19*1\|CYP2C19*2 | | | Intermediate metabolizer | |

Abacavir drug-induced hypersensitivity
Known pathogenic variants - haplotype details Alleles

| | | | | | |
|---|---|---|---|---|---|
| CVID0000174 | na | A | A\|C | 1 non-ref allele | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| VID0000181 | na | T | T\|T | 0 non-ref alleles | dbMHC |
| CVID0000182 | na | G | G\|G | 0 non-ref alleles | dbMHC |
| CVID0000183 | na | C | C\|C | 0 non-ref alleles | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|T | 1 non-ref alleles | dbMHC , |
| CVID0000192 | na | C | C\|C | 0 non-ref alleles | dbMHC |
| CVID0000193 | na | C | G\|G | 2 non-ref alleles | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

Haplotypes

| | | | | | |
|---|---|---|---|---|---|
| HLAB*1502 | HLAB*1502 | CCTGTCCTGGCG GACTACCCGCA (SEQ ID NO: 2) | | 0 non-risk haplotypes | dbMHC |
| HLAB*5701 | HLAB*5701 | CCCACTCAGGGGT CTACCCGCA (SEQ ID NO: 1) | | 0 risk haplotypes | dbMHC |
| default | | not HLAB*1502, not HLAB*5701 | XXXXXXXXXXXX XXXXXXXXX XXX | XXXXXXXXX XXXXXXXXX | 2 non-risk haplotypes | dbMHC |

TABLE 18-continued

Detailed Findings

| Patient Diplotype | default|default | | | Not at risk | |
|---|---|---|---|---|---|

Carbamazepine drug-induced cutaneous adverse events
Known pathogenic variants - haplotype details Alleles

| | | | | | |
|---|---|---|---|---|---|
| CVID0000174 | na | A | A\|C | 1 non-ref allele | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| CVID0000181 | na | T | T\|T | 0 non-ref alleles | dbMHC |
| CVID0000182 | na | G | G\|G | 0 non-ref alleles | dbMHC |
| CVID0000183 | na | C | C\|C | 0 non-ref alleles | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|T | 1 non-ref allele | dbMHC |
| CVID0000192 | na | C | C\|C | 0 non-ref alleles | dbMHC |
| CVID0000193 | na | C | G\|G | 2 non-ref alleles | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

Haplotypes

| | | | | | |
|---|---|---|---|---|---|
| HLAB*1502 | HLAB*1502 | CCTGTCCTGG CGGACTACCC GCA (SEQ ID NO: 2) | | 0 risk haplotypes | dbMHC |
| HLAB*5701 | HLAB*5701 | CCCACTCAGG GGTCTACCCG CA (SEQ ID NO: 1) | | 0 non-risk haplotypes | dbMHC |
| default | not HLAB*1502, not HLAB*5701 | XXXXXXXXXX XXXXXXXXXX X | XXXXXXXXXX XXXXXXXXXX X | 2 non-risk haplotypes | dbMHC |

| Patient Diplotype | | default|default | | Not at risk | |
|---|---|---|---|---|---|

Flucloxacillin drug-induced liver injury
Known pathogenic variants - haplotype details Alleles

| | | | | | |
|---|---|---|---|---|---|
| CVID0000174 | na | A | A\|C | 1 non-ref allele | dbMHC |
| CVID0000175 | na | C | C\|C | 0 non-ref alleles | dbMHC |
| CVID0000176 | na | T | T\|T | 0 non-ref alleles | dbMHC |
| CVID0000177 | na | T | T\|T | 0 non-ref alleles | dbMHC |
| CVID0000178 | na | C | C\|C | 0 non-ref alleles | dbMHC |
| CVID0000179 | na | C | C\|C | 0 non-ref alleles | dbMHC |
| CVID0000180 | na | C | C\|C | 0 non-ref alleles | dbMHC |
| CVID0000181 | na | T | T\|T | 0 non-ref alleles | dbMHC |
| CVID0000182 | na | G | G\|G | 0 non-ref alleles | dbMHC |
| CVID0000183 | na | C | C\|C | 0 non-ref alleles | dbMHC |
| CVID0000184 | na | A | A\|C | 1 non-ref allele | dbMHC |
| CVID0000185 | na | G | G\|G | 0 non-ref alleles | dbMHC |
| CVID0000186 | na | T | T\|T | 0 non-ref alleles | dbMHC |
| CVID0000187 | na | A | A\|A | 0 non-ref alleles | dbMHC |
| CVID0000188 | na | C | C\|C | 0 non-ref alleles | dbMHC |
| CVID0000189 | na | T | T\|T | 0 non-ref alleles | dbMHC |
| CVID0000190 | na | G | G\|G | 0 non-ref alleles | dbMHC |
| CVID0000191 | na | C | C\|T | 1 non-ref allele | dbMHC |
| CVID0000192 | na | C | C\|C | 0 non-ref alleles | dbMHC |
| CVID0000193 | na | C | G\|G | 2 non-ref alleles | dbMHC |
| CVID0000194 | na | G | G\|G | 0 non-ref alleles | dbMHC |
| CVID0000195 | na | C | C\|C | 0 non-ref alleles | dbMHC |
| CVID0000196 | na | C | C\|C | 0 non-ref alleles | dbMHC |

TABLE 18-continued

Detailed Findings

Haplotypes

| | | | | |
|---|---|---|---|---|
| HLAB*1502 | HLAB*1502 | CCTGTCCTGG CGGACTACCC GCA (SEQ ID NO: 2) | 0 non-risk haplotypes | dbMHC |
| HLAB*5701 | HLAB*5701 | CCCACTCAGG GGTCTACCCG CA (SEQ ID NO: 1) | 0 risk haplotypes | dbMHC |
| default | not HLAB*1502, not HLAB*5701 | XXXXXXXXXX XXXXXXXXXX X | XXXXXXXXXX XXXXXXXXXX X 2 non-risk haplotypes | dbMHC |
| Patient Diplotype | | default\|default | Not at risk | |

| Variant Name | Alias or Protein Change | Effect | Reference Allele | Patient Genotype | Findings | Reference (URL or PMID) |
|---|---|---|---|---|---|---|

Statin response modifier
Known Pathogenic Variants - Detail Results

| | | | | | | |
|---|---|---|---|---|---|---|
| CVID0000119 | NP_659464.3:p.Trp719Arg | missense | A | G\|G | 2 pathogenic alleles | 20854963 |

| Variant name | Freq of patient genotype in Ref population* | Ref allele | Patient Genotype | Findings | PMID |
|---|---|---|---|---|---|

Breast cancer, sporadic
Known Pathogenic Variants in patient's ancestry group

Figure 16:
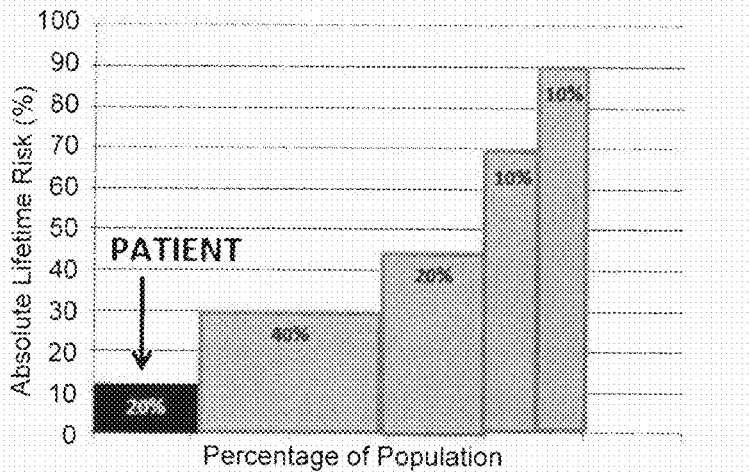
FIG. 16 is a chart of Percentage Absolute Lifetime Risk against Percentage of Population depicting the Distribution of risk in YRI HapMap population relevant to breast cancer.

| | | | | | |
|---|---|---|---|---|---|
| CVID4000006, rs16901937 | 14% | A | A\|G | 1 risk allele (OR 1.21 (1.05, 1.38)) | 20140701 |
| CVID4000007, rs9397435 | 87% | A | A\|A | 0 risk alleles (OR = 1.0) | 20661439 |
| CVID4000009, rs2981578 | 88% | C | C\|C | 1 risk allele (OR = 1.20 (1.03, 1.41)) | 19223389 |
| Distribution of risk in YRI HapMap population: | | See FIG. 16 | | Residual lifetime risk: [need age] Lifetime risk: 11% [pop avg = 10.2%] Relative risk = 1.03X Pop percentile = 66% | SEER^ |

| Variant Name | Alias | Effect | Ref Allele | Patient Genotype | Findings | Reference (URL or PMID) |
|---|---|---|---|---|---|---|

Drug metabolism CYP2B6
Known pathogenic variants - haplotype details

Alleles

| | | | | | |
|---|---|---|---|---|---|
| CVID1001401 | | na | T | T\|T | 0 non-ref alleles |
| CVID1001402 | | na | A | A\|A | 0 non-ref alleles |
| CVID1001403 | | na | C | C\|C | 0 non-ref alleles |
| CVID1001404 | | na | A | A\|A | 0 non-ref alleles |
| CVID1001405 | | na | A | A\|A | 0 non-ref alleles |
| CVID1001406 | | na | G | G\|G | 0 non-ref alleles |
| CVID1001407 | | na | A | A\|A | 0 non-ref alleles |
| CVID1001408 | | na | G | G\|G | 0 non-ref alleles |
| CVID1001409 | | na | C | C\|C | 0 non-ref alleles |
| CVID1001410 | | na | C | C\|C | 0 non-ref alleles |
| CVID1001411 | | na | G | G\|T | 1 non-ref allele |
| CVID1001412 | | na | T | T\|T | 0 non-ref alleles |
| CVID1001413 | | na | C | C\|C | 0 non-ref alleles |
| CVID1001414 | | na | A | A\|G | 1 non-ref allele |
| CVID1001415 | | na | C | C\|C | 0 non-ref alleles |
| CVID1001416 | | na | T | T\|T | 0 non-ref alleles |
| CVID1001417 | | na | C | C\|C | 0 non-ref alleles |
| CVID1001418 | | na | T | T\|T | 0 non-ref alleles |

TABLE 18-continued

Detailed Findings

| | | | | | |
|---|---|---|---|---|---|
| CVID1001419 | na | C | C\|C | 0 non-ref alleles | |
| CVID1001420 | na | A | A\|A | 0 non-ref alleles | |
| CVID1001421 | na | G | G\|G | 0 non-ref alleles | |
| CVID1001422 | na | A | A\|A | 0 non-ref alleles | |
| CVID1001423 | na | C | C\|C | 0 non-ref alleles | |
| Haplotypes | | | | | |
| CYP2B6*1 | normal activity | [string] | [string] | 1 non-risk haplotype | 19225447 |
| CYP2B6*11 | very low activity | [string] | | 0 risk haplotypes | 19225447 |
| CYP2B6*15 | very low activity | [string] | | 0 risk haplotypes | 19225447 |
| CYP2B6*16 | dec expression | [string] | | 0 risk haplotypes | 16495778 |
| CYP2B6*17 | normal activity | [string] | | 0 non-risk haplotypes | 19225447 |
| CYP2B6*18 | dec expression & activity | [string] | | 0 risk haplotypes | 19225447 |
| CYP2B6*2 | normal activity | [string] | | 0 non-risk haplotypes | 19225447 |
| CYP2B6*22 | increased activity | [string] | | 0 risk haplotypes | 17235330 |
| CYP2B6*26 | decreased activity | [string] | | 0 risk haplotypes | 17918089 |
| CYP2B6*27 | decreased activity | [string] | | 0 risk haplotypes | 19225447 |
| CYP2B6*28 | no activity | [string] | | 0 risk haplotypes | 19225447 |
| CYP2B6*3 | normal activity | [string] | | 0 non-risk haplotypes | 19225447 |
| CYP2B6*4 | unknown | [string] | | 0 risk haplotypes | na |
| CYP2B6*5 | normal activity | [string] | | 0 non-risk haplotypes | 19225447 |
| CYP2B6*6 | dec expression & activity | [string] | [string] | 0 risk haplotypes | 19225447 |
| Patient Diplotype | CYP2B6*1\|CYP2B6*18 | | | Intermediate metabolizer | |

| Variant Name | Alias or Protein Change | Effect | Reference Allele | Patient Genotype | Findings | Reference (URL or PMID) |
|---|---|---|---|---|---|---|
| | | Geneticus-Screen Known Pathogenic Variants - Negative Results | | | | |
| 4598 variants - see Locus Development | Various | Various | Various | Various | 0 pathogenic alleles | Various |

*Unk = no published information on genotype:phenotype relationship
*URL and access date: httb://www.cypalleles.ki.se/cyp2c19.htm_091310
^unk = no published information on genotype:phenotype relationship
*YRI-HapMap, ^SEER: http://seer.cancer.gov/csr/1975_2007/

This report was reviewed and approved by:
Rungood E-signature <Date>
Dr. Rungood, Laboratory Director
Appendix
Test Names:
   Physicians can order a test by GeneName or ConditionName. However we will report on conditions. This is because a gene can be involved in one or more conditions and it is possible that we have not curated variants for the other condition.
Definitions:
Ethnicity
   Used for reporting certain conditions with quantitative risk models. Physicians can select one or more of the choices. We can produce three scores: one for Asian, one for AA/Black, and one for White. If the physician requests OTHER (or hand writes a non-Locus ethnic group) we will provide three scores. If the physician requests Asian and White we will provide two scores.

Pathogenic (Known)—ACMG Category 1
   We will look for and report on pathogenic variants that have been previously observed in affected individuals. Variants included in qualitative reports are considered pathogenic if they have been observed in an affected individual and result in a deleterious mutation (such as nonsense, truncation, disruption of consensus splice site, or disruption of the initiator codon). Other types of mutations (such as missense, inframe substitutions or deletions) are considered pathogenic if there is experimental evidence to support pathogenicity. Variants included in quantitative conditions are considered pathogenic if there are at least two independent association studies in the same ethnic group showing statistically significant association (after correction for multiple testing). If that same variant is also significantly associated in an additional ethnic group it is considered pathogenic.
Pathogenic (Novel)—ACMG Category 2
   Novel pathogenic mutations for qualitative reports are those that have not been described in an affected individual and result in a deleterious mutation (such as nonsense, truncation, disruption of consensus splice site, or disruption of the initiator codon).

Ref Allele

Refers to the allele present at that coordinate in GRCh37. In some cases the reference allele might be the risk allele.

Sequence

The consensus base call and coverage is provided for each base sequenced. In addition a variant file for the individual is produced which contains information about positions that differ from the reference genome.

Variant of Unknown Significance (VUS)—ACMG Categories 3-6

A variant of unknown significance may have been observed in affected individuals but does not meet the criteria of pathogenicity or may be a novel variant with unclear functional effect. We provide frequency information and computational prediction for the functional effect of these variants.

General Disclaimer:

DNA studies do not constitute a definitive test for the selected condition(s) in all individuals. It should be realized that there are many possible sources of diagnostic error. Genotyping errors can result from trace contamination of PCR reactions and from rare genetic variants that interfere with analysis. This test is used for clinical purposes. It should not be regarded as investigational or for research. The laboratory is regulated under CLIA of 1988.

tests with the generation of the response excluding analysis of the second set of markers with respect to tests other than the one or more tests;

assigning an identifier to the sequence data, the identifier identifying the sample, the requisition and information related to the analysis;

storing the sequence data in a repository of data, the repository comprising one or more databases for baseline, diagnostic and statistical data for analyzing the sequence data and wherein the one ore more databases comprises at least one internal database in which the sequence data from the sample is stored;

after generating the response, generating a notification of health information based upon an analysis of sequence data based on (1) a change to a prediction in the response to the first requisition, (2) one or more tests which were not available for requisition at the time of the first requisition, or (3) at least a portion of the second set of markers, wherein the health information which is the subject of the notification comprises health information which is different from the health information in the response;

and generating such health information after consent for its generation is received.

---

---

What is claimed is:

1. A method for analyzing diagnostic information, comprising:

extracting genomic DNA from a sample from a subject, obtaining sequence data for a plurality of markers, the plurality of markers including a first set of markers which are associated with one or more tests identified in a first requisition corresponding to the sample, the first requisition being solicited by a healthcare requestor, and a second set of markers comprising any portion of all currently available marker not directly associated with the first requisition, wherein the first requisition includes a request to receive future notifications of health information associated with the sequence data;

generating a response to the first requisition, the response being based upon an analysis of sequence data corresponding to the first set of markers and the one or more 2. The method of claim 1 wherein the health information which is the subject of the notification concerns a change to a prediction in the response where such change arises due to a change in the content of the repository.

3. The method of claim 1 wherein the health information which is the subject of the notification concerns one or more tests which were not available for requisition at the time of the first requisition.

4. The method of claim 3 wherein the health information which is the subject of the notification is generated with reference to sequence data corresponding to at least one marker of the second set of markers.

5. The method of claim 1 wherein the consent for generating the notification of health information is provided with the first requisition.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
cccactcagg ggtctacccg ca                                              22

<210> SEQ ID NO 2
<211> LENGTH: 23
<212> TYPE: DNA
<213> ORGANISM: Homo sapiens

<400> SEQUENCE: 2
cctgtcctgg cggactaccc gca                                             23